United States Patent
Lebel et al.

(10) Patent No.: US 6,740,075 B2
(45) Date of Patent: May 25, 2004

(54) AMBULATORY MEDICAL APPARATUS WITH HAND HELD COMMUNICATION DEVICE

(75) Inventors: Ronald J. Lebel, Sherman Oaks, CA (US); Varaz Shahmirian, Northridge, CA (US); Timothy J. Starkweather, Simi Valley, CA (US); Daniel H. Villegas, Grananda Hills, CA (US); David Y. Choy, San Gabriel, CA (US); Philip T. Weiss, Pasadena, CA (US); Colin A. Chong, Glendale, CA (US); Peter C. Lord, Santa Clarita, CA (US); Wayne A. Morgan, Northridge, CA (US); Paul M. Meadows, La Canada Flintridge, CA (US)

(73) Assignee: Medtronic Minimed, Inc., Northridge, CA (US)

( * ) Notice: Subject to any disclaimer, the term of this patent is extended or adjusted under 35 U.S.C. 154(b) by 177 days.

(21) Appl. No.: 09/768,204

(22) Filed: Jan. 22, 2001

(65) Prior Publication Data

US 2003/0065370 A1 Apr. 3, 2003

Related U.S. Application Data

(60) Provisional application No. 60/177,414, filed on Jan. 21, 2000.

(51) Int. Cl.$^7$ .................................................. A61K 9/22
(52) U.S. Cl. ..................................... 604/891.1; 604/151
(58) Field of Search ................................ 607/27, 30–43, 607/48, 52, 54, 57–61, 103, 113, 115–122, 148–156; 604/891, 151–153, 891.2; 600/300–301, 322–327, 372–381, 418, 423, 430–435, 466–527, 544, 584–586

(56) References Cited

U.S. PATENT DOCUMENTS

| | | | | |
|---|---|---|---|---|
| 4,258,711 A | * | 3/1981 | Tucker et al. | 128/207.19 |
| 4,373,527 A | * | 2/1983 | Fischell | 604/891 |
| 4,487,603 A | * | 12/1984 | Harris | 604/152 |
| 4,494,950 A | | 1/1985 | Fischell | |

(List continued on next page.)

FOREIGN PATENT DOCUMENTS

| | | |
|---|---|---|
| EP | 0 346 783 | 6/1989 |
| WO | WO 95/02426 | 1/1995 |
| WO | WO 96/03168 | 2/1996 |
| WO | WO 97/18639 | 5/1997 |

OTHER PUBLICATIONS

PCT International Search Report as issued in International Application No. PCT/US01/23003, Mailing Date Jul. 3, 2002.

(List continued on next page.)

*Primary Examiner*—Mark Bockelman
(74) *Attorney, Agent, or Firm*—Foley & Lardner LLP

(57) ABSTRACT

A communication device (CD) exchanges messages with an implantable infusion pump via telemetry such that commands are supplied thereto and operational information is obtained therefrom. The CD is controlled, at least in part, by a processor IC according to a software program operating therein and provides feedback to a user via a visual display, an audio alarm, and a vibrational alarm, and allows input from the user via a touch sensitive keypad. Certain input functions are restricted by password. The visual display includes an icon and fixed element display region and a bitmap display region. The fixed element display region includes time and date displays, battery and drug level displays that decrement, and a moving delivery state display. Various screens allow operational or log information to be displayed and/or user entry of commands. Program features when disabled are removed from a series of screen options that can be scrolled through.

26 Claims, 16 Drawing Sheets

U.S. PATENT DOCUMENTS

| | | | |
|---|---|---|---|
| 5,127,404 A | 7/1992 | Wyborny et al. | |
| 5,191,326 A | 3/1993 | Montgomery | |
| 5,368,562 A | 11/1994 | Blomquist et al. | 604/65 |
| 5,416,695 A | 5/1995 | Stutman et al. | |
| 5,438,621 A | 8/1995 | Hornak et al. | |
| 5,456,692 A | 10/1995 | Smith et al. | 607/31 |
| 5,620,474 A * | 4/1997 | Koopman | 607/29 |
| 5,630,710 A | 5/1997 | Tune et al. | 417/326 |
| 5,647,854 A | 7/1997 | Olsen et al. | 604/174 |
| 5,658,133 A | 8/1997 | Anderson et al. | 417/63 |
| 5,658,250 A | 8/1997 | Blomquist et al. | 604/65 |
| 5,659,299 A | 8/1997 | Williamson et al. | |
| 5,669,877 A | 9/1997 | Blomquist | 604/67 |
| 5,695,473 A | 12/1997 | Olsen | 604/153 |
| 5,718,234 A | 2/1998 | Warden et al. | |
| 5,720,770 A * | 2/1998 | Nappholz et al. | 607/30 |
| 5,724,985 A * | 3/1998 | Snell et al. | 607/30 |
| 5,733,313 A * | 3/1998 | Barreras, Sr. et al. | 607/33 |
| 5,749,907 A * | 5/1998 | Mann | 607/27 |
| 5,788,669 A | 8/1998 | Peterson | 604/65 |
| 5,800,472 A * | 9/1998 | Mann | 607/29 |
| 5,810,771 A | 9/1998 | Blomquist | 604/65 |
| 5,876,370 A | 3/1999 | Blomquist | 604/65 |
| 5,935,099 A | 8/1999 | Peterson et al. | 604/65 |
| 5,935,106 A | 8/1999 | Olsen | 604/153 |
| 6,024,539 A | 2/2000 | Blomquist | 417/63 |
| 6,026,124 A | 2/2000 | Lee et al. | |
| 6,057,758 A * | 5/2000 | Dempsey et al. | 607/32 |
| 6,088,618 A * | 7/2000 | Kerver | 607/30 |
| 6,123,686 A | 9/2000 | Olsen et al. | 604/151 |
| 6,155,267 A * | 12/2000 | Nelson | 600/509 |
| 6,409,674 B1 * | 6/2002 | Brockway et al. | 600/486 |
| 6,418,346 B1 * | 7/2002 | Nelson et al. | 607/59 |

OTHER PUBLICATIONS

PCT International Search Report as issued in International Application No. PCT/US01/22926, Mailing Date Jul. 8, 2002.

PCT International Search Report as isued in International Application No. PCT/US01/23003, Mailing Date Jul. 3, 2002.

PCT International Search Report as issued in International Application No. PCT/US01/22926, Mailing Date Jul. 8, 2002.

\* cited by examiner

MAIN MENU

SETUP MENUS

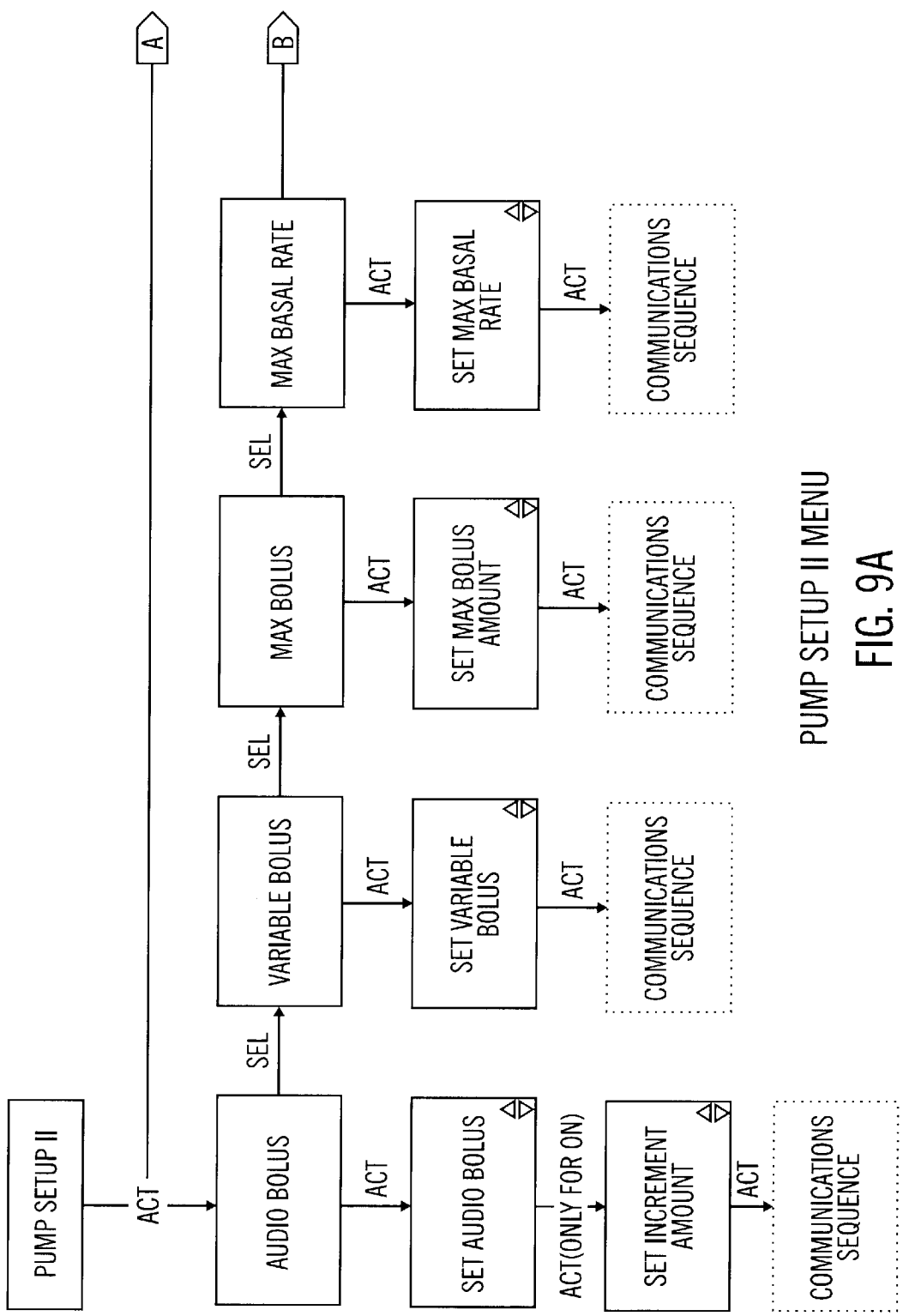

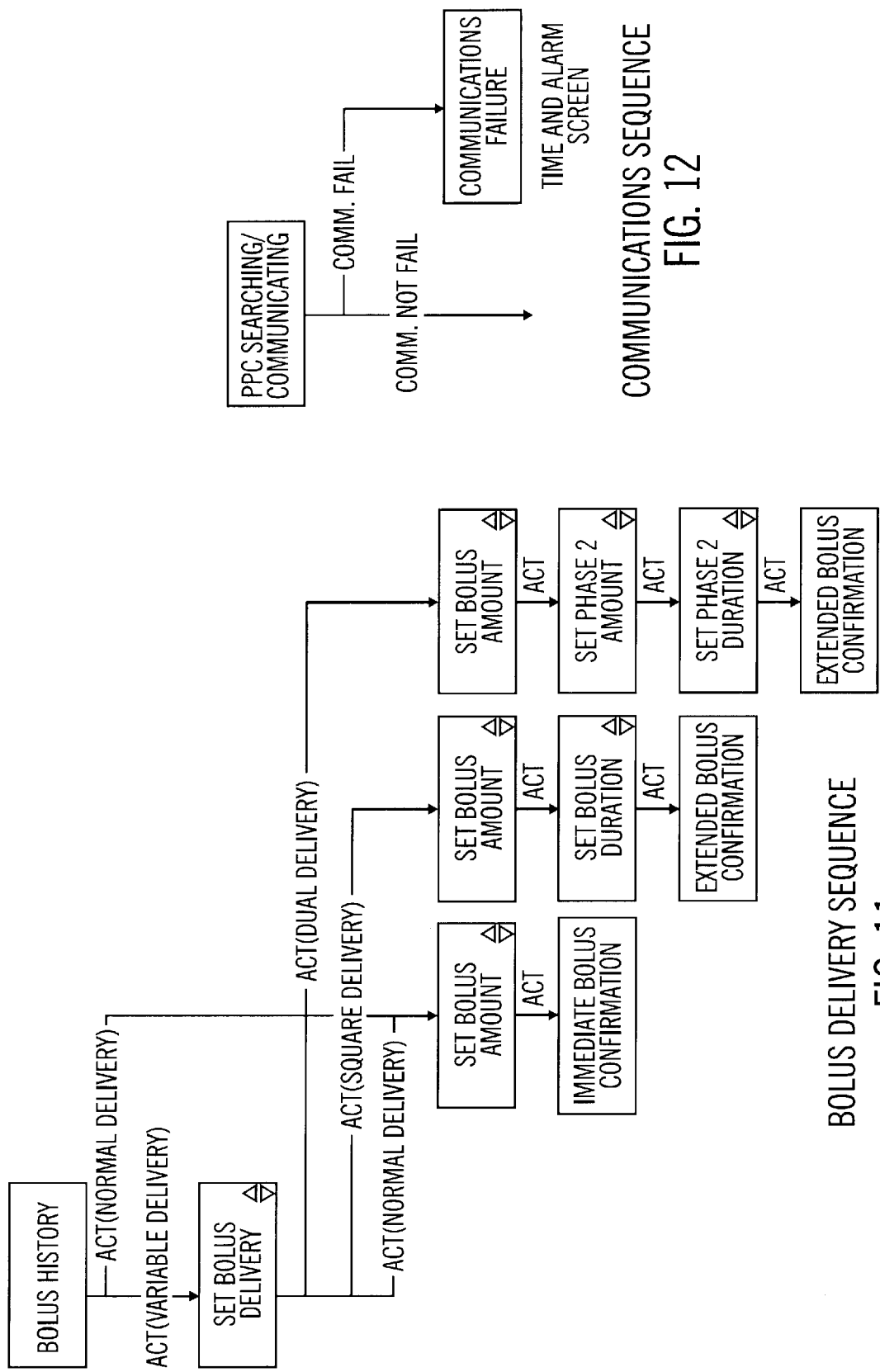

AMBULATORY MEDICAL APPARATUS WITH HAND HELD COMMUNICATION DEVICE

RELATED APPLICATIONS

This application claims the benefit of prior filed U.S. Provisional Patent Application No. 60/177,414; filed Jan. 21, 2000, by Ronald J. Lebel, et al., and entitled "Medical Apparatus and Method Including an Implantable Device and an External Communication Device". The entirety of this provisional application is hereby incorporated herein by this reference, including appendices filed therewith and any references incorporated therein by reference, as if set forth in full herein.

FIELD OF THE DISCLOSURE

This invention relates generally to electronically controlled ambulatory medical systems that include an ambulatory medical device and a hand held microprocessor controlled communication device with enhanced user friendliness including enhanced display/patient notification features, safety features, and/or medical device programming/communication features. Preferred embodiments relate to implantable infusion pumps and external devices for communicating therewith.

BACKGROUND

Implantable infusion pumps for dispensing controlled volumes of a drug (e.g. insulin) have been proposed and even attempts at implementation and commercialization made.

One such pump is the MMT2001 Implantable Pump System as sold by Minimed Inc. of Northridge, Calif. This device presented the user with the ability to perform basic infusion actions such as the delivery of a basal rate, delivery of a temporary basal rate, or the delivery of a meal bolus. The user was, however, not presented with the ability to perform more sophisticated delivery related operations that may be desirable for optimum control of blood glucose level. When using this system three delivery options exist: (1) delivery of a standard but programmable basal rate, (2) delivery of a standard basal rate and a meal bolus simultaneously, or (3) delivery of a temporary basal rate either immediately or at a programmable start time within a specifiable start time. In this system not only could a meal bolus and a temporary basal rate not occur at the same time, they could not be programmed into the system when the other was already programmed but delivery not yet completed even though no overlap in delivery between the two amounts might exist. As such the user could only program one variable rate into the system at a time, even in the event that several variable rates may be desired to follow one another. As such, this system is less than optimal with regard to user convenience in programming his/her insulin treatment.

The system also suffered from an external controller that was large, hard to carry and awkward to use. The controller dimensions are 6.0 inches by 3.5 inches by 1.3 inches with a display that is a small fraction of the size of the face of the controller. The controller included a cover plate that would close over the display area when not in use and would be opened during use. More particularly, during programming the cover plate is opened at a ninety-degree angle relative to the front of the display to allow viewing of the display and to allow positioning of the cover plate immediately over the site of the infusion pump so that successful telemetry communication may occur. As such the system does not supply delivery or system status related information to the user except at the times that the user elects to open and turn on his/her controller.

The system further suffers from the inability of the implantable device to send out unsolicited telemetry messages to the controller concerning operational conditions within the implantable device. As such, system conditions within the implantable device (other than communication related failures) are primarily conveyed to the user via an auditory alarm that is internal to the implantable device.

The system further suffers from the entire operational history of the pump being subject to loss as this historical data is only held in the controller.

The system further suffered from a relatively short life for the implantable device of approximately 2.5 years.

Based on the above noted shortcomings, and other shortcomings of systems in the field, a need exists for improved systems that offer enhanced programming capabilities, enhanced user interface capabilities, reduced controller size, enhanced operational performance, enhanced security of system/patient historical data, enhanced safety features, and/or enhanced implantable device life.

It is believed that related shortcoming may exist in other ambulatory medical devices as well, such as in externally carried infusion pumps, implantable pacemakers, implantable defibrillators, implantable neural stimulators, implantable physiological sensors, externally carried physiologic sensors, and the like.

SUMMARY OF THE INVENTION

It is a first object of certain aspects of the invention to enhance programming capabilities for ambulatory medical systems and in particular for implantable infusion pump systems.

It is a second object of certain aspects of the invention to enhance user interface capabilities in ambulatory medical systems and in particular for implantable infusion pump systems.

It is a third object of certain aspects of the invention to reduce system size for patient convenience in ambulatory medical systems and in particular for implantable infusion pump systems.

It is a fourth object of certain aspects of the invention to enhance operational performance of ambulatory medical systems and in particular for implantable infusion pump systems.

It is a fifth object of certain aspects of the invention to enhance security of system/patient historical data.

It is a sixth object of certain aspects of the invention to enhance the operational safety of ambulatory medical systems and in particular of implantable infusion pump systems.

It is a seventh object of certain aspects of the invention to enhance longevity of ambulatory medical systems and in particular of implantable infusion pump systems.

Other objects and advantages of various aspects of the invention will be apparent to those of skill in the art upon review of the teachings herein. The various aspects of the invention set forth below as well as other aspects of the invention not specifically set forth below but ascertained from the teachings found herein, may address the above noted objects or other objects ascertained from the teachings herein individually or in various combinations. As such, it is intended that each aspect of the invention address at least one of the above noted objects or address some other object that will be apparent to one of skill in the art from a review of the teachings herein. It is not intended that all, or even a portion of these objects, necessarily be addressed by any single aspect of the invention even though that may be the case with regard to some aspects.

A first aspect of the invention provides a medical system that includes (a) an ambulatory medical device (MD) that includes MD electronic control circuitry that further includes at least one MD telemetry system and at least one MD processor that controls, at least in part, operation of the MD telemetry system and operation of the medical device, wherein the medical device is configured to provide a treatment to a body of a patient or to monitor a selected state of the body; and (b) a communication device (CD) that includes CD electronic control circuitry that further includes at least one CD telemetry system and at least one CD processor that controls, at least in part, operation of the CD telemetry system and operation of the communication device, wherein the CD telemetry system sends messages to or receives messages from the MD telemetry system, wherein the communication device weighs no more than about 10 oz and includes a CD housing having a volumetric size smaller than 20 cubic inches.

A second aspect of the invention provides a medical system that includes (a) an ambulatory medical device (MD) that includes MD electronic control circuitry that further includes at least one MD telemetry system and at least one MD processor that controls, at least in part, operation of the MD telemetry system and operation of the medical device, wherein the medical device is configured to provide a treatment to a body of a patient or to monitor a selected state of the body; and (b) a communication device (CD) that includes CD electronic control circuitry that further includes at least one CD telemetry system and at least one CD processor that controls, at least in part, operation of the CD telemetry system and operation of the communication device, wherein the CD telemetry system sends messages to or receives messages from the MD telemetry system, wherein the communication device additionally includes a CD readable display which includes a bit map region for displaying selected information.

A third aspect of the invention provides a medical system that includes (a) an ambulatory medical device (MD) that includes MD electronic control circuitry that further includes at least one MD telemetry system and at least one MD processor that controls, at least in part, operation of the MD telemetry system and operation of the medical device, wherein the medical device is configured to provide a treatment to a body of a patient or to monitor a selected state of the body; and (b) a communication device (CD) that includes CD electronic control circuitry that further includes at least one CD telemetry system and at least one CD processor that controls, at least in part, operation of the CD telemetry system and operation of the communication device, wherein the CD telemetry system sends messages to or receives messages from the MD telemetry system wherein the communication device additionally includes a readable display which includes at least one icon.

A fourth aspect of the invention provides a medical system that includes (a) an ambulatory medical device (MD) that includes MD electronic control circuitry that further includes at least one MD telemetry system and at least one MD processor that controls, at least in part, operation of the MD telemetry system and operation of the medical device, wherein the medical device is configured to provide a treatment to a body of a patient or to monitor a selected state of the body; and (b) a communication device (CD) that includes CD electronic control circuitry that further includes at least one CD telemetry system and at least one CD processor that controls, at least in part, operation of the CD telemetry system and operation of the communication device, wherein the CD telemetry system sends messages to or receives messages from the MD telemetry system wherein the communication device additionally includes a readable CD display which further includes a backlight.

In a specific variation of the fourth aspect of the invention the communication device additionally includes a touch sensitive CD input device and wherein the backlight is automatically activated when one or more selected locations on the CD input device are touched.

In a specific variation of the fourth aspect of the invention the backlight is activated automatically when a light level falling on a sensor on the communication device is less than a predetermined amount and a touch sensitive region of the communication device is touched.

A fifth aspect of the invention provides a medical system that includes (a) an ambulatory medical device (MD) that includes MD electronic control circuitry that further includes at least one MD telemetry system and at least one MD processor that controls, at least in part, operation of the MD telemetry system and operation of the medical device, wherein the medical device is configured to provide a treatment to a body of a patient or to monitor a selected state of the body; and (b) a communication device (CD) that includes CD electronic control circuitry that further includes at least one CD telemetry system and at least one CD processor that controls, at least in part, operation of the CD telemetry system and operation of the communication device, wherein the CD telemetry system sends messages to or receives messages from the MD telemetry system, wherein the communication device further includes an automatically activated CD alarm that is capable of providing a signal to the patient of the existence of a particular condition in at least one of the medical device or the communication device, and wherein the CD alarm includes at least one of a CD vibration mechanism or a CD audio alarm mechanism.

In a specific variation of the fifth aspect of the invention the communication device is configured to enable a patient to select between the CD alarm using the audio and vibration mechanism.

In a specific variation of the fifth aspect of the invention an alarm condition in the medical device is transmitted to the communication device via an unsolicited telemetry message.

In a specific variation of the fifth aspect of the invention the communication device is configured to automatically switch from one of the audio alarm or the vibration alarm to the other of the vibration alarm or the audio alarm under selected circumstances associated with at least one error condition.

In a specific variation of the fifth aspect of the invention one of the medical device or the communication device includes an audio alarm that produces a plurality of tones emitted in a predetermined sequence.

A sixth aspect of the invention provides a medical system that includes (a) an ambulatory medical device (MD) that includes MD electronic control circuitry that further includes at least one MD telemetry system and at least one MD processor that controls, at least in part, operation of the MD telemetry system and operation of the medical device, wherein the medical device is configured to provide a treatment to a body of a patient or to monitor a selected state of the body; and (b) a communication device (CD) that includes CD electronic control circuitry that further includes at least one CD telemetry system and at least one CD processor that controls, at least in part, operation of the CD telemetry system and operation of the communication device, wherein the CD telemetry system sends messages to or receives messages from the MD telemetry system wherein the communication device additionally includes a CD touch sensitive input device, and wherein the communication device additionally includes a readable CD display which further includes a capability of displaying different colors.

In a specific variation of the sixth aspect of the invention the CD display is configured to display a single color at any one time.

In a specific variation of the sixth aspect of the invention the CD display is configured to display a plurality of colors at a single time.

A seventh aspect of the invention provides a medical system that includes (a) an ambulatory medical device (MD) that includes MD electronic control circuitry that further includes at least one MD telemetry system and at least one MD processor that controls, at least in part, operation of the MD telemetry system and operation of the medical device, wherein the medical device is configured to provide a treatment to a body of a patient or to monitor a selected state of the body; and (b) a communication device (CD) that includes CD electronic control circuitry that further includes at least one CD telemetry system and at least one CD processor that controls, at least in part, operation of the CD telemetry system and operation of the communication device, wherein the CD telemetry system sends messages to or receives messages from the MD telemetry system, wherein the communication device additionally includes a readable display that is also touch sensitive for allowing user inputs to be entered into the communication device.

A eighth aspect of the invention provides a medical system that includes (a) an ambulatory medical device (MD) that includes MD electronic control circuitry that further includes at least one MD telemetry system and at least one MD processor that controls, at least in part, operation of the MD telemetry system and operation of the medical device, wherein the medical device is configured to provide a treatment to a body of a patient or to monitor a selected state of the body; and (b) a communication device (CD) that includes CD electronic control circuitry that further includes at least one CD telemetry system and at least one CD processor that controls, at least in part, operation of the CD telemetry system and operation of the communication device, wherein the CD telemetry system sends messages to or receives messages from the MD telemetry system, wherein the communication device additionally includes a CD touch sensitive input device and a CD speaker that is controlled to supply speech based output to the patient.

A ninth aspect of the invention provides a medical system that includes (a) an ambulatory medical device (MD) that includes MD electronic control circuitry that further includes at least one MD telemetry system and at least one MD processor that controls, at least in part, operation of the MD telemetry system and operation of the medical device, wherein the medical device is configured to provide a treatment to a body of a patient or to monitor a selected state of the body; and (b) a communication device (CD) that includes CD electronic control circuitry that further includes at least one CD telemetry system and at least one CD processor that controls, at least in part, operation of the CD telemetry system and operation of the communication device, wherein the CD telemetry system sends messages to or receives messages from the MD telemetry system, wherein the communication device additionally includes a CD input device which further includes a CD microphone and a CD voice recognition system that are controlled to allow speech based input to the communication device.

A tenth aspect of the invention provides a medical system that includes (a) an ambulatory medical device (MD) that includes MD electronic control circuitry that further includes at least one MD telemetry system and at least one MD processor that controls, at least in part, operation of the MD telemetry system and operation of the medical device, wherein the medical device is configured to provide a treatment to a body of a patient or to monitor a selected state of the body; and (b) a communication device (CD) that includes CD electronic control circuitry that further includes at least one CD telemetry system and at least one CD processor that controls, at least in part, operation of the CD telemetry system and operation of the communication device, wherein the CD telemetry system sends messages to or receives messages from the MD telemetry system wherein the communication device additionally includes a CD touch sensitive input device, and wherein the communication device is configured to perform a plurality of functions, and wherein the performance of at least a first function requires that the communication device be placed in an operational state dictated by a first or a second password and the performance of at least a second function requires that the communication device be placed in an operational state dictated the second password.

In a specific variation of the tenth aspect of the invention the communication device can perform all functions with the second password that can be performed with the first password.

A eleventh aspect of the invention provides a medical system that includes (a) an ambulatory medical device (MD) that includes MD electronic control circuitry that further includes at least one MD telemetry system and at least one MD processor that controls, at least in part, operation of the MD telemetry system and operation of the medical device, wherein the medical device is configured to provide a treatment to a body of a patient or to monitor a selected state of the body; and (b) a communication device (CD) that includes CD electronic control circuitry that further includes at least one CD telemetry system and at least one CD processor that controls, at least in part, operation of the CD telemetry system and operation of the communication device, wherein the CD telemetry system sends messages to or receives messages from the MD telemetry system, wherein the communication device includes a touch sensitive CD input device, and wherein at least one of the communication device or the medical device may be reset, or placed in a state to allow reset to occur, by contacting a plurality of selected locations on the touch sensitive CD input device in a prescribed order.

In a specific variation of the eleventh aspect of the invention password must be entered into the communication device prior to touching the plurality of selected locations on the touch sensitive CD input device in order for reset to occur.

In a specific variation of the eleventh aspect of the invention a password must be entered into the communication device after touching the plurality of selected locations on the touch sensitive CD input device in order for reset to occur.

In a specific variation of the eleventh aspect of the invention the plurality of touch sensitive locations are touched sequentially in order for reset to occur.

In a specific variation of the eleventh aspect of the invention at least a portion of the plurality of touch sensitive locations must be touched simultaneously for reset to occur.

In a specific variation of the eleventh aspect of the invention at least a portion of the plurality of touch sensitive locations must be touched and then untouched in a particular order for reset to occur.

In a specific variation of the eleventh aspect of the invention resetting may occur to different extents depending on variations in the plurality of touch sensitive locations touched, variations in the sequence of touching, or variations in the sequence of untouching.

A twelfth aspect of the invention provides a medical system that includes (a) an ambulatory medical device (MD) that includes MD electronic control circuitry that further includes at least one MD telemetry system and at least one MD processor that controls, at least in part, operation of the MD telemetry system and operation of the medical device, wherein the medical device is configured to provide a treatment to a body of a patient or to monitor a selected state of the body; and (b) a communication device (CD) that includes CD electronic control circuitry that further includes at least one CD telemetry system and at least one CD processor that controls, at least in part, operation of the CD telemetry system and operation of the communication device, wherein the CD telemetry system sends messages to or receives messages from the MD telemetry system, wherein the communication device is configured to receive status information on an MD battery via telemetry from the medical device.

In a specific variation of the twelfth aspect of the invention the medical device provides a periodic indication of the MD battery voltage when the MD battery is experiencing a current load that is closer to the minimum load during normal operation of the medical device than a maximum load during normal operation.

In a specific variation of the twelfth aspect of the invention the medical device provides a periodic indication of the MD battery voltage when the MD battery is experiencing a current load which is closer to the maximum load during normal operation than a minimum load during normal operation.

In a specific variation of the twelfth aspect of the invention MD battery status is provided using both a lower current load and a higher current load at least once a week.

In a specific variation of the twelfth aspect of the invention the communication device provides an auditory, visual, or tactile warning when the MD battery is estimated to be capable of powering the medical device for less than a predetermined additional amount of time.

A thirteenth aspect of the invention provides a medical system that includes (a) an ambulatory medical device (MD) that includes MD electronic control circuitry that further includes at least one MD telemetry system and at least one MD processor that controls, at least in part, operation of the MD telemetry system and operation of the medical device, wherein the medical device is configured to provide a treatment to a body of a patient or to monitor a selected state of the body; and (b) a communication device (CD) that includes CD electronic control circuitry that further includes at least one CD telemetry system and at least one CD processor that controls, at least in part, operation of the CD telemetry system and operation of the communication device, wherein the CD telemetry system sends messages to or receives messages from the MD telemetry system, wherein the communication device additionally includes at least one battery and the medical device includes at least one battery, and wherein the communication device is configured to display log data of MD battery status information or CD battery status information.

In a specific variation of the thirteenth aspect of the invention the log information includes a plurality of voltage readings taken from a predefined battery when the predefined battery is powering a first load and when the predefined battery is powering a second load which is different from the first load.

In a specific variation of the thirteenth aspect of the invention the log data is accumulated at least once per week.

A fourteenth aspect of the invention provides a medical system that includes (a) an ambulatory medical device (MD) that includes MD electronic control circuitry that further includes at least one MD telemetry system and at least one MD processor that controls, at least in part, operation of the MD telemetry system and operation of the medical device, wherein the medical device is configured to provide a treatment to a body of a patient or to monitor a selected state of the body; and (b) a communication device (CD) that includes CD electronic control circuitry that further includes at least one CD telemetry system and at least one CD processor that controls, at least in part, operation of the CD telemetry system and operation of the communication device, wherein the CD telemetry system sends messages to or receives messages from the MD telemetry system, wherein the communication device additionally includes a socket for a removable memory module.

In a specific variation of the fourteenth aspect of the invention the communication device includes the removable memory module.

In a specific variation of the fourteenth aspect of the invention the removal memory module contains replacement software for the communication device, replacement software for the medical device, or calibration data for a sensor that forms part of the medical device.

A fifteenth aspect of the invention provides a medical system that includes (a) an ambulatory medical device (MD) that includes MD electronic control circuitry that further includes at least one MD telemetry system and at least one MD processor that controls, at least in part, operation of the MD telemetry system and operation of the medical device, wherein the medical device is configured to provide a treatment to a body of a patient or to monitor a selected state of the body; and (b) a communication device (CD) that includes CD electronic control circuitry that further includes at least one CD telemetry system and at least one CD processor that controls, at least in part, operation of the CD telemetry system and operation of the communication device, wherein the CD telemetry system sends messages to or receives messages from the MD telemetry system, wherein the medical device includes an implantable device, and wherein the communication device includes a memory for simultaneously storing a plurality of parameters that are each used during a different time period to, at least in part, control the treatment provided to the body or the monitoring of the body that is provided by the medical device.

In a specific variation of the fifteenth aspect of the invention the implantable device includes an infusion pump that is capable of dispensing a selected quantity of a drug according to a programmed parameter, and wherein each of the plurality of parameters includes a basal rate parameter that is programmed for use in controlling the dispensing of the drug during a selected time period during the day. In a further variation the plurality of parameters comprise a plurality of sets of parameters, wherein each set includes a plurality of parameters, wherein the medical device is capable of storing only one set at a time, and wherein the communication device transmits a selected on of the sets to the communication device when it is desired for the parameters of the transmitted set to control, at least in part, the dispensing of the drug.

A sixteenth aspect of the invention provides a medical system that includes (a) an ambulatory medical device (MD) that includes MD electronic control circuitry that further includes at least one MD telemetry system and at least one MD processor that controls, at least in part, operation of the MD telemetry system and operation of the medical device, wherein the medical device is configured to provide a treatment to a body of a patient or to monitor a selected state of the body; and (b) a communication device (CD) that includes CD electronic control circuitry that further includes at least one CD telemetry system and at least one CD processor that controls, at least in part, operation of the CD telemetry system and operation of the communication device, wherein the CD telemetry system sends messages to or receives messages from the MD telemetry system, wherein the medical system additionally includes a second device (SD) that includes an SD communication system, wherein the communication device further includes a second CD communication system, and wherein the communication device is programmable so as to echo all CD telemetry system messages, sent or received from the medical device, through the second CD communication system to the SD communication system.

A seventeenth aspect of the invention provides a medical system that includes (a) an ambulatory medical device (MD) that includes MD electronic control circuitry that further includes at least one MD telemetry system and at least one MD processor that controls, at least in part, operation of the MD telemetry system and operation of the medical device, wherein the medical device is configured to provide a treatment to a body of a patient or to monitor a selected state of the body; and (b) a communication device (CD) that includes CD electronic control circuitry that further includes at least one CD telemetry system and at least one CD processor that controls, at least in part, operation of the CD telemetry system and operation of the communication device, wherein the CD telemetry system sends messages to or receives messages from the MD telemetry system, wherein the medical system additionally includes a second device (SD) that includes an SD communication system, wherein the communication device further includes a second CD communication system, and wherein the communication device is programmable to pass messages received from the second device on to the medical device via transfer from the SD communication system to the second CD communication system to the CD telemetry system and on to MD telemetry system of the medical device, and/or to pass messages received from the medical device to the second device via transfer from MD telemetry system to the CD telemetry system to the second CD communication system and then onto the SD telemetry system of the second device, and wherein the content of the messages is passed without modification.

A eighteenth aspect of the invention provides a medical system that includes (a) an ambulatory medical device (MD) that includes MD electronic control circuitry that further includes at least one MD telemetry system and at least one MD processor that controls, at least in part, operation of the MD telemetry system and operation of the medical device, wherein the medical device is configured to provide a treatment to a body of a patient or to monitor a selected state of the body; and (b) a communication device (CD) that includes CD electronic control circuitry that further includes at least one CD telemetry system and at least one CD processor that controls, at least in part, operation of the CD telemetry system and operation of the communication device, wherein the CD telemetry system sends messages to or receives messages from the MD telemetry system, wherein the medical system additionally includes a second device (SD) that includes an SD communication system, wherein the communication device further includes a second CD communication system that is capable of sending messages to or receiving messages from the SD communication system, and wherein the communication device additionally includes a CD keypad, and wherein the communication device is capable of receiving messages from the second device that emulate keystrokes on the keypad.

A nineteenth aspect of the invention provides a medical system that includes (a) an ambulatory medical device (MD) that includes MD electronic control circuitry that further includes at least one MD telemetry system and at least one MD processor that controls, at least in part, operation of the MD telemetry system and operation of the medical device, wherein the medical device is configured to provide a treatment to a body of a patient or to monitor a selected state of the body; and (b) a communication device (CD) that includes CD electronic control circuitry that further includes at least one CD telemetry system and at least one CD processor that controls, at least in part, operation of the CD telemetry system and operation of the communication device, wherein the CD telemetry system sends messages to or receives messages from the MD telemetry system, wherein the communication device is programmed to accept input parameters that specify the delivery of a predefined quantity of treatment to the body of the patient over a prescribed time period wherein the average rate of delivery per minute of portions of the predefined quantity varies as a function of time according to a preprogrammed delivery profile.

In a specific variation of the nineteenth aspect of the invention the preprogrammed delivery profile results in a bell shaped curve of average delivery per minute versus time. In a further variation the communication device allows the patient to select a most suitable of a plurality of bell shaped delivery profiles. In a further variation at least one of the curves is symmetric. In still a further variation at least one of the curves is non-symmetric with a generally steeper upward slope than downward slope.

A twentieth aspect of the invention provides a medical system that includes (a) an ambulatory medical device (MD) that includes MD electronic control circuitry that further includes at least one MD telemetry system and at least one MD processor that controls, at least in part, operation of the MD telemetry system and operation of the medical device, wherein the medical device is configured to provide a treatment to a body of a patient or to monitor a selected state of the body; and (b) a communication device (CD) that includes CD electronic control circuitry that further includes at least one CD telemetry system and at least one CD processor that controls, at least in part, operation of the CD telemetry system and operation of the communication device, wherein the CD telemetry system sends messages to or receives messages from the MD telemetry system, wherein the communication device is powered by a replaceable battery and wherein sufficient power is stored in one or more capacitors within the communication device that a controlled power down can occur when the replaceable battery is removed such that upon replacement of the battery the communication device need not be reprogrammed to resume operation.

In a specific variation of the twentieth aspect of the invention the communication device monitors the voltage on the replaceable batter so as to detect a removal of the battery and initiate and complete a controlled shut down prior to the capacitors losing a required minimum voltage.

A twenty-first aspect of the invention provides a medical system that includes (a) an ambulatory medical device (MD) that includes MD electronic control circuitry that further includes at least one MD telemetry system and at least one MD processor that controls, at least in part, operation of the MD telemetry system and operation of the medical device, wherein the medical device is configured to provide a treatment to a body of a patient or to monitor a selected state of the body; and (b) a communication device (CD) that includes CD electronic control circuitry that further includes at least one CD telemetry system and at least one CD processor that controls, at least in part, operation of the CD telemetry system and operation of the communication device, wherein the CD telemetry system sends messages to or receives messages from the MD telemetry system, wherein the medical device is configured to provide a drug to the body of a patient in amounts that are integer multiples of a quantized amount, wherein the communication device is programmed to allow entry of delivery quantities that are not integral multiples of the quantized amount.

A twenty-second aspect of the invention provides a medical system that includes (a) an ambulatory medical device (MD) that includes MD electronic control circuitry that further includes at least one MD telemetry system and at least one MD processor that controls, at least in part, operation of the MD telemetry system and operation of the medical device, wherein the medical device is configured to provide a treatment to a body of a patient or to monitor a selected state of the body; and (b) a communication device (CD) that includes CD electronic control circuitry that further includes at least one CD telemetry system and at least one CD processor that controls, at least in part, operation of the CD telemetry system and operation of the communication device, wherein the CD telemetry system sends messages to or receives messages from the MD telemetry system, wherein the communication device additionally includes a CD display device for providing visual communication signals to the patient which further includes a zoomable display so that the size of displayed images may be adjusted to a desired size.

In a specific variation of the twenty-second aspect of the invention the CD display device includes a LCD bit map display.

A twenty-third aspect of the invention provides a medical system that includes (a) an ambulatory medical device (MD) that includes MD electronic control circuitry that further includes at least one MD telemetry system and at least one MD processor that controls, at least in part, operation of the MD telemetry system and operation of the medical device, wherein the medical device is configured to provide a treatment to a body of a patient or to monitor a selected state of the body; and (b) a communication device (CD) that includes CD electronic control circuitry that further includes at least one CD telemetry system and at least one CD processor that controls, at least in part, operation of the CD telemetry system and operation of the communication device, wherein the CD telemetry system sends messages to or receives messages from the MD telemetry system, wherein the medical device includes an infusion pump, and wherein the CD display device is controlled to show a plurality of infusion parameters simultaneously.

A twenty-fourth aspect of the invention provides a medical system that includes (a) an ambulatory medical device (MD) that includes MD electronic control circuitry that further includes at least one MD telemetry system and at least one MD processor that controls, at least in part, operation of the MD telemetry system and operation of the medical device, wherein the medical device is configured to provide a treatment to a body of a patient or to monitor a selected state of the body; and (b) a communication device (CD) that includes CD electronic control circuitry that further includes at least one CD telemetry system and at least one CD processor that controls, at least in part, operation of the CD telemetry system and operation of the communication device, wherein the CD telemetry system sends messages to or receives messages from the MD telemetry system, wherein the CD display device includes a moving image that graphically depicts a status of the system.

In a specific variation of the twenty-fourth aspect of the invention the medical device includes an infusion pump and the status being depicted includes an indication of a delivery status. In a further variation the moving image rotates. In a further variation the image includes a number of elements that may be active or inactive and differing numbers of active elements indicates different delivery states.

A twenty-fifth aspect of the invention provides a medical system that includes (a) an ambulatory medical device (MD) that includes MD electronic control circuitry that further includes at least one MD telemetry system and at least one MD processor that controls, at least in part, operation of the MD telemetry system and operation of the medical device, wherein the medical device is configured to provide a treatment to a body of a patient or to monitor a selected state of the body; and (b) a communication device (CD) that includes CD electronic control circuitry that further includes at least one CD telemetry system and at least one CD processor that controls, at least in part, operation of the CD telemetry system and operation of the communication device, wherein the CD telemetry system sends messages to or receives messages from the MD telemetry system, wherein the communication device includes a CD display controlled by the at least one CD processor for providing visual feedback to the patient, and wherein the feedback includes a display of the quantity of a consumable estimated to be remaining in the system.

In a specific variation of the twenty-fifth aspect of the invention the consumable is a quantity of a drug estimated to be remaining in a reservoir.

In a specific variation of the twenty-fifth aspect of the invention the consumable is either (1) battery power remaining in a replaceable CD battery in the communication device and a voltage level on the CD battery is graphically depicted with a desired resolution, or (2) battery power remaining in an MD battery in the medical device and a voltage level on the battery is graphically depicted with a desired resolution.

A twenty-sixth aspect of the invention provides a medical system that includes (a) an ambulatory medical device (MD) that includes MD electronic control circuitry that further includes at least one MD telemetry system and at least one MD processor that controls, at least in part, operation of the MD telemetry system and operation of the medical device, wherein the medical device is configured to provide a treatment to a body of a patient or to monitor a selected state of the body; and (b) a communication device (CD) that includes CD electronic control circuitry that further includes at least one CD telemetry system and at least one CD processor that controls, at least in part, operation of the CD telemetry system and operation of the communication device, wherein the CD telemetry system sends messages to or receives messages from the MD telemetry system, wherein the CD display is controlled to depict a plurality of patient programmable options and wherein at least one of the patient programmable options may be enabled or disabled such that when disabled the at least one patient programmable option is no longer displayed as an option.

A twenty-seventh aspect of the invention provides a medical system that includes (a) an ambulatory medical device (MD) that includes MD electronic control circuitry that further includes at least one MD telemetry system and at least one MD processor that controls, at least in part, operation of the MD telemetry system and operation of the medical device, wherein the medical device is configured to provide a treatment to a body of a patient or to monitor a selected state of the body; and (b) a communication device (CD) that includes CD electronic control circuitry that further includes at least one CD telemetry system and at least one CD processor that controls, at least in part, operation of the CD telemetry system and operation of the communication device, wherein the CD telemetry system sends messages to or receives messages from the MD telemetry system, wherein the medical device or the communication device monitors battery voltage and generates a voltage log, wherein the medical device monitors a CD voltage of a CD battery in the communication device and generates a CD voltage log.

In a specific variation of the twenty-seventh aspect of the invention the log includes a plurality of CD voltage values for each of a plurality of different current drain states.

A twenty-eighth aspect of the invention provides a medical system that includes (a) an ambulatory medical device (MD) that includes MD electronic control circuitry that further includes at least one MD telemetry system and at least one MD processor that controls, at least in part, operation of the MD telemetry system and operation of the medical device, wherein the medical device is configured to provide a treatment to a body of a patient or to monitor a selected state of the body; and (b) a communication device (CD) that includes CD electronic control circuitry that further includes at least one CD telemetry system and at least one CD processor that controls, at least in part, operation of the CD telemetry system and operation of the communication device, wherein the CD telemetry system sends messages to or receives messages from the MD telemetry system, wherein both the medical device and the communication device have memories for storing selected data about system operation, wherein at least a portion of the selected data is duplicated in the medical device and the communication device.

In a specific variation of the twenty-eighth aspect of the invention the communication device is programmed to periodically synchronize the duplicated data.

In a specific variation of the twenty-eighth aspect of the invention at least a portion of the selected data is synchronized automatically or is synchronized in response to a synchronization command.

A twenty-ninth aspect of the invention provides a medical system that includes (a) an ambulatory medical device (MD) that includes MD electronic control circuitry that further includes at least one MD telemetry system and at least one MD processor that controls, at least in part, operation of the MD telemetry system and operation of the medical device, wherein the medical device is configured to provide a treatment to a body of a patient or to monitor a selected state of the body; and (b) a communication device (CD) that includes CD electronic control circuitry that further includes at least one CD telemetry system and at least one CD processor that controls, at least in part, operation of the CD telemetry system and operation of the communication device, wherein the CD telemetry system sends messages to or receives messages from the MD telemetry system, wherein the communication device is programmed to allow a user to set a plurality of parameters to predefined default values by issuing a command that does require specification of any of the default values.

A thirtieth aspect of the invention provides a medical system that includes (a) an ambulatory medical device (MD) that includes MD electronic control circuitry that further includes at least one MD telemetry system and at least one MD processor that controls, at least in part, operation of the MD telemetry system and operation of the medical device, wherein the medical device is configured to provide a treatment to a body of a patient or to monitor a selected state of the body; and (b) a communication device (CD) that includes CD electronic control circuitry that further includes at least one CD telemetry system and at least one CD processor that controls, at least in part, operation of the CD telemetry system and operation of the communication device, wherein the CD telemetry system sends messages to or receives messages from the MD telemetry system, wherein the communication device is capable of performing a test of battery voltage with a load on the battery.

In a specific variation of the thirtieth aspect of the invention the test of battery voltage is performed automatically and periodically. In a further variation at least one of the following will occur, (1) the battery voltage is also automatically and periodically checked with the battery under a minimal load, (2) at least one selected electrical component is forced on to produce the load for testing, or (3) the test is made to occur at least in part when at least one selected electrical component is powered on in the performance of its normal operation, wherein the electrical component provides a load for the testing.

A thirty-first aspect of the invention provides a medical system that includes (a) an ambulatory medical device (MD) that includes MD electronic control circuitry that further includes at least one MD telemetry system and at least one MD processor that controls, at least in part, operation of the MD telemetry system and operation of the medical device, wherein the medical device is configured to provide a treatment to a body of a patient or to monitor a selected state of the body; and (b) a communication device (CD) that includes CD electronic control circuitry that further includes at least one CD telemetry system and at least one CD processor that controls, at least in part, operation of the CD telemetry system and operation of the communication device, wherein the CD telemetry system sends messages to or receives messages from the MD telemetry system, wherein at least one of the medical device or communication device has a memory for storing at least one calibration factor needed for proper operation of the system.

In a specific variation of the thirty-first aspect of the invention the medical device includes an infusion pump mechanism for dispensing a drug held in a reservoir within the medical device and the at least one calibration factor includes at least one of (1) information about the concentration of the drug, (2) delivery volume per discrete operation of an infusion pump mechanism, (3) the amount of drug placed in the reservoir when filled, (4) a voltage value necessary to cause the pump mechanism to operate properly, (5) a value to be used by a pulse stealer circuit, (6) a calibration factor to be used by an analog to digital converter, or (7) a specific telemetry ID of the device.

A thirty-second aspect of the invention provides a medical system that includes (a) an ambulatory medical device (MD) that includes MD electronic control circuitry that further includes at least one MD telemetry system and at least one MD processor that controls, at least in part, operation of the MD telemetry system and operation of the medical device, wherein the medical device is configured to provide a treatment to a body of a patient or to monitor a selected state of the body; and (b) a communication device (CD) that includes CD electronic control circuitry that further includes at least one CD telemetry system and at least one CD processor that controls, at least in part, operation of the CD telemetry system and operation of the communication device, wherein the CD telemetry system sends messages to or receives messages from the MD telemetry system, wherein at least one of the medical device or communication device includes a first component or module that may be powered directly by a battery when the battery's output voltage is above a predetermined level, and wherein the at least on of the medical device or communication device includes a voltage up converter that is used to supply electrical potential to the first component or module when the battery voltage is below the predetermined level.

A thirty-third aspect of the invention provides a medical system that includes (a) an ambulatory medical device (MD) that includes MD electronic control circuitry that further includes at least one MD telemetry system and at least one MD processor that controls, at least in part, operation of the MD telemetry system and operation of the medical device, wherein the medical device is configured to provide a treatment to a body of a patient or to monitor a selected state of the body; and (b) a communication device (CD) that includes CD electronic control circuitry that further includes at least one CD telemetry system and at least one CD processor that controls, at least in part, operation of the CD telemetry system and operation of the communication device, wherein the CD telemetry system sends messages to or receives messages from the MD telemetry system, wherein at least one watchdog circuit is capable of causing the CD processor to undergo a predefined process in the event that the watchdog circuit does not receive a first signal and a second signal, which is different from the first signal, within a predefined time period.

In a specific variation of the thirty-third aspect of the invention the predefined process causes the CD processor to be reset. In a further variation one of the first or second signals is a signal generated by mainline software. In a further variation the other of the first or second signals is a signal generated by interrupt hardware.

A thirty-fourth aspect of the invention provides a medical system that includes (a) an ambulatory medical device (MD) that includes MD electronic control circuitry that further includes at least one MD telemetry system and at least one MD processor that controls, at least in part, operation of the MD telemetry system and operation of the medical device, wherein the medical device is configured to provide a treatment to a body of a patient or to monitor a selected state of the body; and (b) a communication device (CD) that includes CD electronic control circuitry that further includes at least one CD telemetry system and at least one CD processor that controls, at least in part, operation of the CD telemetry system and operation of the communication device, wherein the CD telemetry system sends messages to or receives messages from the MD telemetry system, wherein an antenna for the MD telemetry system is mounted on a hybrid circuit board in the medical device and wherein the antenna for the CD telemetry system is mounted on a hybrid circuit board in the communication device.

A thirty-fifth aspect of the invention provides a medical system that includes (a) an ambulatory medical device (MD) that includes MD electronic control circuitry that further includes at least one MD telemetry system and at least one MD processor that controls, at least in part, operation of the MD telemetry system and operation of the medical device, wherein the medical device is configured to provide a treatment to a body of a patient or to monitor a selected state of the body; and (b) a communication device (CD) that includes CD electronic control circuitry that further includes at least one CD telemetry system and at least one CD processor that controls, at least in part, operation of the CD telemetry system and operation of the communication device, wherein the CD telemetry system sends messages to or receives messages from the MD telemetry system, wherein the communication device monitors electrical activity of at least one electronic module or component located within the communication device and compares the electrical activity to at least one predetermined value.

In a specific variation of the thirty-fifth aspect of the invention, there will be one of the following, (1) the at least one electronic module is located within an application specific integrated circuit that includes the CD processor, (2) the at least one electronic module includes a crystal oscillator circuit, (3) the at least one electronic module includes a driver for the treatment or monitoring device, (4) the predetermined value includes an upper and lower limit of a range of values, or (5) the electrical activity includes a current flow.

Additional specific variations, provide the medical devices of each of the above aspects and above noted variations as implantable devices such as implantable infusion pumps, implantable physiological sensors, implantable stimulators, and the like, or external devices such subcutaneous delivery infusion pumps or sensors that ascertain a physiological parameter or parameters from subcutaneous tissue or from the skin of the patient. Such infusion pumps may dispense insulin, analgesics, neurological drugs, drugs for treating aids, drugs for treating chronic ailments or acute ailments. Sensors may be used to detect various physiological parameters such as hormone levels, insulin, pH, oxygen, other blood chemical constituent levels, and the like. The sensor may be of the electrochemical type, optical type, and may or may not be enzymatic in operation.

In even further variations of the above noted aspects, and above noted variations, one or more of the following is provided: (1) a first portion of the MD telemetry system is incorporated into the MD processor and a second portion of the MD telemetry system is external to the MD processor, (2) a first portion of the CD telemetry system is incorporated into the CD processor and a second portion of the CD telemetry system is external to the CD processor, (3) the MD processor includes an MD central processing unit and at least one other MD functional module, (4) the CD processor includes a CD central processing unit and at least one other CD functional module, (5) the MD electronic control circuitry includes at least one external MD functional module, other than a portion of the MD telemetry system, that is external to the MD processor, or (6) the CD electronic control circuitry includes at least one external CD functional module, other than a portion of the CD telemetry system, that is external to the CD processor.

Still additional aspects of the invention set forth method counterparts to the above system aspects as well as to other functional associations and relationships, and processes that have not been specifically set forth above but will be understood by those of skill in the art from a review of the teachings provided herein.

Further aspects of the invention will be understood by those of skill in the art upon reviewing the teachings herein. These other aspects of the invention may provide various combinations of the aspects presented above as well as provide other configurations, structures, functional relationships, and processes that have not been specifically set forth above.

BRIEF DESCRIPTION OF THE DRAWINGS

The above referred to objects and aspects of the present invention will be further understood from a review of the description to follow, the drawings, and the claims set forth hereafter, wherein:

FIGS. 9a and 9b depicts the setup ii menu structure for the user interface of the external communication device of the first preferred embodiment;

FIG. 11 depicts the bolus delivery sequence or menu structure for the user interface of the external communication device of the first preferred embodiment; and FIG. 12 depicts the communication sequence associated with the user interface of the external communication device of the first preferred embodiment.

DETAILED DESCRIPTION OF PREFERRED EMBODIMENTS

Figure 1A:
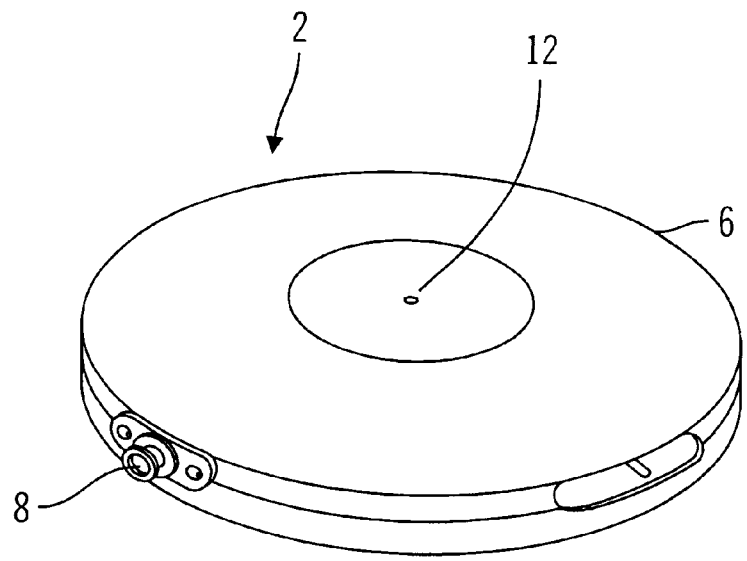
FIG. 1a depicts a perspective view of the main body of the implantable device of the first preferred embodiment.

Various details about the structural and functional configuration and operation of preferred ambulatory medical devices and preferred communication devices are found in several U.S. patent applications filed concurrently herewith and incorporated herein by reference in their entireties: (1) Docket No. USP-1075-A, (2) Docket No. USP-1076-A, (3) Docket No. USP-1077-A, (4) Docket No. USP-1079-A, and (5) Docket No. USP-1080-A.

U.S. patent application Ser. No. 09/768,045, filed on Jan. 22, 2001 (concurrently herewith), by Starkweather, et al., entitled "Ambulatory Medical Apparatus and Method Having Telemetry Modifiable Control Software", corresponding to Medical Research Group, Inc. Docket No. USP-1075-A, is hereby incorporated herein by this reference as if set forth in full herein. This application provides teachings concerning an implantable medical device (e.g. infusion pump) and handheld communication device wherein the implantable device is capable of operating under control of different software programs, wherein a first program operates after resetting the implantable device and is not capable of allowing significant medical functionality but is capable of selected telemetry operations including telemetry operations that allow replacement software to be downloaded, and wherein a second program may be caused to take control of the device and enables medical functionality and selected telemetry operations but is incapable of receiving replacement software. It is also taught that a software image may be received in multiple messages where each message is provided with its own validation code and wherein a validation code for the whole image is provided and wherein each provided validation code must compared to a derived validation code prior to accepting the validity of the replacement software.

U.S. patent application Ser. No. 09/768,202, filed on Jan. 22, 2001 (concurrently herewith), by Lebel, et al., entitled "Ambulatory Medical Apparatus and Method Using a Robust Communication Protocol", corresponding to Medical Research Group, Inc. Docket No. USP-1076-A, is hereby incorporated herein by this reference as if set forth in full herein. An implanted medical device (e.g. infusion pump) and external device communicate with one another via telemetry wherein messages are transmitted under a robust communication protocol. The communication protocol gives enhanced assurance concerning the integrity of messages that impact medical operations of the implantable device. Messages are transmitted using a multipart format that includes a preamble, a frame sync, a telemetry ID, data, and a validation code. The data portion of the message includes an op-code that dictates various other elements that form part of the message. The data portion may also include additional elements such as sequence numbers, bolus numbers, and duplicate data elements. A telemetry ID for the transmitting device may be implicitly embedded in the message as part of the validation code that is sent with the message and that must be pre-known by the receiver to confirm the integrity of the received message.

U.S. patent application Ser. No. 09/768,206, filed on Jan. 22, 2001 (concurrently herewith), by Bowman, et al., entitled "Ambulatory Medical Apparatus and Method using a Telemetry System with Predefined Reception Listening Periods", corresponding to Medical Research Group, Inc. Docket No. USP-1077-A, is hereby incorporated herein by this reference as if set forth in full herein. This application provides teachings concerning an implantable medical device (e.g. infusion pump) and an external device that communicate with one another via telemetry messages that are receivable only during listening windows. Each listening window is open for a prescribed listening period and is spaced from other listening windows by an interval. The listening period is typically kept small to minimize power consumption. To increase likelihood of successful communication, the window may be forced to an open state, by use of an attention signal, in anticipation of an incoming message. To further minimize power consumption, it is desirable to minimize use of extended attention signals, and this is accomplished by the transmitter maintaining an estimate of prescribed listening start times and attempting to send messages only during listening periods. In the communication device, the estimate is updated as a result of information obtained with the reception of each message from the medical device.

U.S. patent application Ser. No. 09/768,207, filed on Jan. 22, 2001 (concurrently herewith), by Starkweather, et al., entitled "Method and Apparatus for Communicating Between an Ambulatory Medical Device and Control Device Via Telemetry Using Randomized Data", corresponding to Medical Research Group, Inc. Docket No. USP-1079-A, is hereby incorporated herein by this reference as if set forth in full herein. This application provides teachings concerning an implantable medical device (e.g. infusion pump) and handheld communication device that communicate with one another via telemetry wherein transmitted messages have enhanced numbers of and/or regularity of bit transitions to minimize the risk of synchronization loss between transmitted bits of data and received bits of data. It is taught that bit transitions for portions of messages may be enhanced by applying a pseudo-randomization scheme to those portions of messages that are transmitted in a way that allows the receiver to extract the original data from the received randomized data. Preferred randomization techniques modify (i.e. randomize) the data using a CRC value that is being accumulated while simultaneously causing the modified data to modify subsequent accumulation of the CRC itself. Upon reception, the reversal of data randomization is then made to occur so that the intended message is appropriately received.

U.S. patent application Ser. No. 09/768,221, filed on Jan. 22, 2001 (concurrently herewith), by Lebel, et al., entitled "Microprocessor Controlled Ambulatory Medical Apparatus with Hand Held Communication Device", corresponding to Medical Research Group, Inc. Docket No. USP-1080-A, is hereby incorporated herein by this reference as if set forth in full herein. This application provides teachings concerning an implantable medical device (e.g. infusion pump) and handheld communication device, wherein an implantable infusion pump possesses operational functionality that is, at least in part, controlled by software operating in two processor ICs which are configured to perform some different and some duplicate functions. The pump exchanges messages with the external communication device via telemetry. Each processor controls a different part of the drug infusion mechanism such that both processors must agree on the appropriateness of drug delivery for infusion to occur. Delivery accumulators are incremented and decremented with delivery requests and with deliveries made. When accumulated amounts reach or exceed, quantized deliverable amounts, infusion is made to occur. The accumulators are capable of being incremented by two or more independent types of delivery requests. Operational modes of the infusion device are changed automatically in view of various system errors that are trapped, various system alarm conditions that are detected, and when excess periods of time lapse between pump and external device interactions.

The first embodiment of the present invention provides a long term implantable medical delivery system that controllably supplies insulin to the body of a patient afflicted with diabetes mellitus. This embodiment includes an implantable medical device and an external communication device. In the most preferred embodiments, the communication device is a hand held device that is used directly by the patient to interact with the medical device as opposed to being limited to use by a physician, nurse, or technician. It is preferred that the communication device provide (1) the ability to send commands to the medical device, (2) receive information from the medical device, and (3) be able to present to the patient at least a portion of the information it receives from the medical device. In preferred embodiments, the patient interacts with the medical device via the communication device at least once per week, on average, more preferably at least once every other day, on average, and most preferably at least once per day, on average.

The implantable medical device (MD) includes a biocompatible housing; a reservoir within the housing for holding a quantity of insulin; a side port that attaches to the side of the housing, a catheter, that connects to the side port; a pumping mechanism, within the housing for moving the insulin from the reservoir through the sideport and through the catheter to the body of the patient; and control, monitoring, and communication electronics located within the housing. In alternative embodiments various portions of implantable medical device hardware may be located outside the housing. For example, the pumping mechanism or a telemetry antenna may be located within the sideport or other side mounted housing; or a telemetry antenna may mounted on the outside surface of the housing, or extend along the catheter The external communication device (CD) communicates commands to the medical device, receives information from the medical device, and communicates system status and system history to the patient. The external communication device includes a housing; a keypad mounted on the housing; a display forming part of the housing; and control, monitoring, and communication electronics located within the housing. In alternative embodiments, the keypad may be replaced in whole or in part by a touch sensitive display or a voice recognition system. In addition, or alternatively, the display may be replaced in whole or in part by a speech generation system or other audio communication system.

Figure 1B:
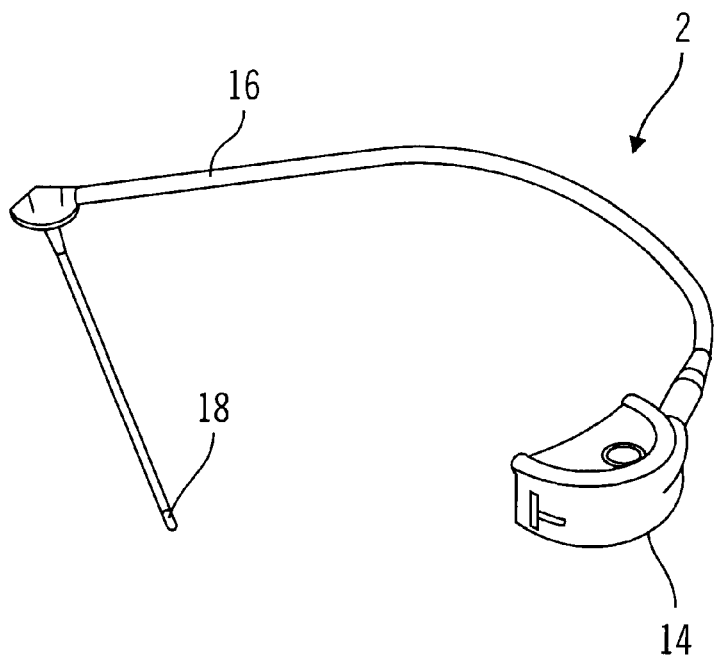
FIG. 1b depicts a perspective view of the support and catheter assembly that attaches to the main body of the implantable device of the first preferred embodiment.

The outer appearance of the implantable device 2 is depicted in two pieces in FIGS. 1a and 1b and includes housing 6 having a drug outlet port 8, and a refill port 12, a removable sideport 14 that mounts against the side of the housing 6 over outlet port 8, and a catheter 16 having a distal end 18 and a proximal end that attaches to sideport 14. In alternative embodiments, the implantable device may take on a different shape and/or the sideport may be removed in favor of a permanently mounted catheter assembly.

Figure 2:
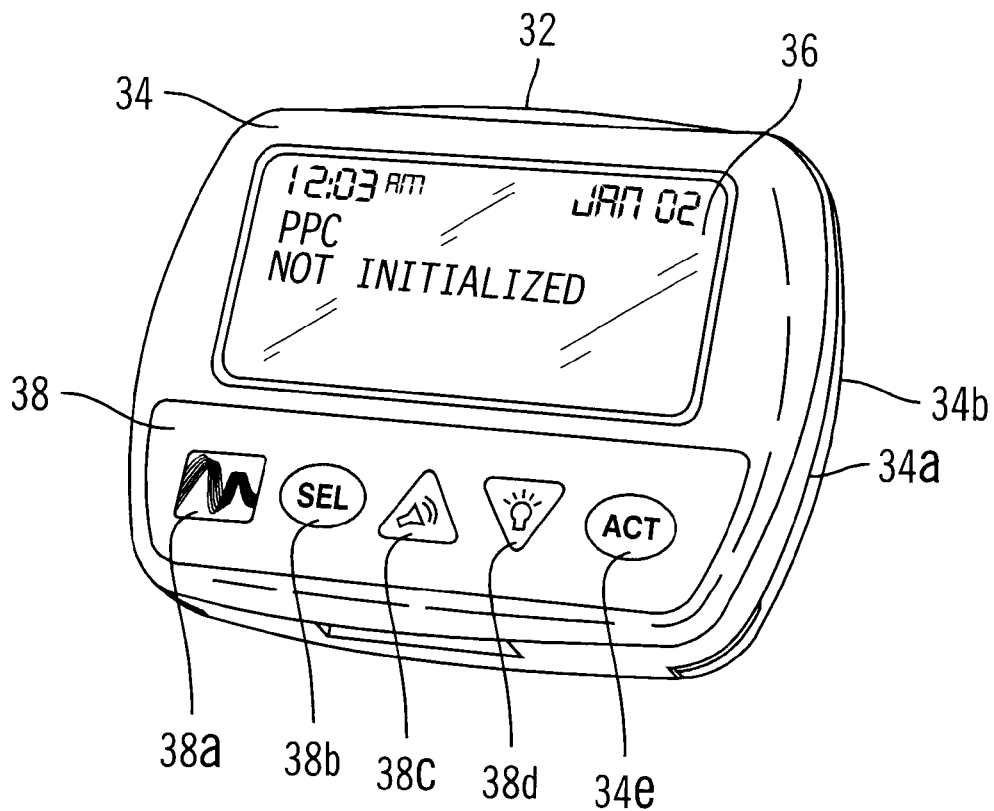
FIG. 2 depicts a perspective view of the external communication device of the first preferred embodiment.

The outer appearance of the external communication device 32 is depicted in FIG. 2. The various components of the external communication device are fitted in or on housing 34. Housing 34 is divided into a front portion 34a and a back portion 34b. The front portion 34a is provided with an opening in which an LCD panel 36 is positioned. The panel 36 has a lower portion that is a bit map display and an upper portion that provides icons and fixed element displays. The front portion 34a of the external communication device is also provided with a five-element keypad 38. A first key 38a is not located under a raised pad and does not provide tactile feedback when it is touched and may be used for special functions. The remaining four keys 38b, 38c, 38d, and 38e have raised pads that provide tactile feedback when they are depressed. These remaining keys may be used in normal device operation and are known as the select key, the up arrow key, down arrow key, and the activate key, respectively. The back portion 34b of the housing is fitted with a door under which a compartment is located for holding a replaceable battery.

The implantable device includes a memory for storing program code and data. A portion of the memory in the implantable device is preferably used to store configuration information for the external communication device and for the implantable device itself. This allows the configuration data to be reloaded into a replacement external communication device if the original should be lost or damaged. This memory is also used to store system operation information in the form of activity logs and counters, such an insulin delivery log. Various portions of the contents of implantable device memory are downloaded to the external communication device periodically. The downloads to the external communication device may occur manually, automatically, or semi-automatically.

The implantable device control electronics include various self-checking mechanisms to ensure that reliable operation of the system occurs. For example, as the pumping mechanism in this first embodiment requires a firing voltage that is significantly greater than the supply voltage, a pre-fire voltage on the pump firing circuit is checked to ensure it is large enough to cause the pump to execute a full stroke. After firing, the voltage is checked again, to ensure that discharging of the circuit occurred. Each processor is monitored by a watchdog circuit that must be serviced, periodically. As implemented in the software, servicing must occur at both the interrupt level and at the mainline code level to ensure that the processor has not malfunctioned at either level. Insulin delivery calculations are performed by both processors in such a manner that both processors must agree on the quantity and timing of insulin delivery. If an error of a significant nature is found in the system, the implantable device may be placed in a protective mode (i.e. suspend mode or stop mode) where insulin delivery is cut back to a medically insignificant rate (e.g. about 1 pump stroke per hour) or stopped completely. It is preferred to have a small amount of insulin be delivered periodically to help prevent the occurrence of catheter blockage. In any event, if system failure does occur the system effectively stops delivery and attempts to warn the patient.

As the implantable device is controlled by messages that it receives from the external communication device, messages sent to the implantable device have their accuracy and appropriateness checked with varying degrees of scrutiny depending on the critically of the message.

First, for example, almost all messages are sent from a particular external communication device to a particular implantable device using explicit identification information of the receiver to identify itself as the intended recipient. It is considered desirable to use identification information with messages that relate to medical treatment (e.g. the changing of insulin infusion rates). More particularly it is desirable to use identification information with messages that relate to changing medical treatment in a way that could have acute ramifications (e.g. to over supplying a drug such as insulin as opposed to under supplying the drug).

Second, the identity of the sender is preferably embedded implicitly in the message. This implicit embedding occurs by using the identification information of the sender in calculating a cyclical redundancy code (CRC) that is sent with the message. As such, the implantable device must know the identity of the sender in order to successfully check the content of the message against the transmitted CRC.

Third, the values of the data in the message are compared to an operation code (Op Code) sent with the message to ensure that the code and data are compatible. This Op Code is also used to set the size of the most messages, thereby providing a mechanism to increase electrical efficiency of the system by providing a way to limit reception time to only that amount necessary to receive a particular message.

Fourth, if the message pertains to drug delivery, the message is sent with redundant data that must match for the message to be interpreted as valid. If for any reason the message is interpreted as invalid, the message is ignored.

To avoid problems associated with long transmissions that may otherwise contain long strings of non-transitioning data (i.e. long strings of 1s or 0s), the data portion of most messages are randomized prior to transmission and de-randomized upon receipt. For energy savings and time savings, randomization and de-randomization preferably occur in a single pass through the data and preferably utilize the semi-random attributes of the CRC tables from which CRC codes are built.

In the event that an error or other significant event occurs in the implantable device, the device may attempt to inform the patient of the event by sending a telemetry message to the external communication device or alternatively by activating an audio alarm mechanism within the implantable device itself.

The implantable device is preferably configured so that the software running in it can be replaced or upgraded if the need should arise. The software may be downloaded into the implantable device through telemetry. The implantable device may be operated under two types of software: (1) bootloader code, or (2) application code. The bootloader code may be broken down into first stage boot loader code which is stored in the ROM that is internal to the ASIC and second stage bootloader code that is stored in a SEEPROM or other non-volatile memory associated with each ASIC. The bootloader code and application code are different for each ASIC.

The bootloader code does not care about the application in which the implantable device may be used. The bootloader code is not concerned with whether, the implantable device is an infusion device, a sensor, a stimulator, or the like, or a combination thereof. On the other hand, the application code is concerned with the medical functionality of the device and thus is designed specifically for a given type of application. As such, if an implantable device includes a pump and was initially configured (i.e. loaded with specific application software) to work with one drug (e.g. insulin) in one manner (e.g. allowing different preprogrammed basal rate changes to occur at the beginning of each half hour of the day and allowing simultaneous use of an immediate bolus and an extended bolus), it could be reconfigured to operate in a completely different manner while using the same drug or a different drug by simply changing its application code. The replacement of application code in this context is different from a mere change in program variables that may allow various control limits to be changed or even to allow the code to execute different algorithms that are preexistant within the code. The replacement of application code in this context involves the replacement of at least portions of the code that set forth program algorithms.

When operating under control of the bootloader code, the implantable device allows certain telemetry operations to occur and also allows downloading of new application code, but does not allow any drug delivery. The application code when controlling the system, on the other hand, knows how to handle drug delivery but is not capable of downloading new code, or otherwise modifying itself (other than to accept changes in parameter values). The bootloader code is also designed and operated in such a way that new bootloader code can be downloaded to the SEEPROM if an upgrade is felt to be appropriate.

In alternative embodiments, it is possible to merge the functionality of the second stage bootloader code and the application code into a single piece of code that can be upgraded as desired. In still further embodiments, it may be possible only to upgrade the application code and not the second stage bootloader code.

As noted above, the implantable device assembly includes a detachable catheter and sideport that provides a pathway for the insulin to a desired infusion location in the patient's body (e.g. into the patient's peritoneal cavity). The sideport allows for non-surgical diagnosis of a catheter blockage by using pressure. The sideport allows introduction of a refill needle and small syringe to clear an obstructed catheter (e.g. using up to 110 psi of pressure). The sideport also allows the introduction of a refill needle and a pipet to verify pump stroking. The catheter includes a check valve that seals (e.g. at between 0.5 to 3 psid) and provides a redundant valve outside the pump to prevent medication or body fluids from back flowing into the implantable device reservoir. The sideport in conjunction with the check valve facilitates rinsing the fluid path within the implanted device with sodium hydroxide, or other functionally similar material, by allowing effluent to be drawn out the sideport rather than pumped out the catheter tip. In alternative embodiments, a sideport may not be used.

As noted above, the external communication device has both an audio alarm and a vibrator for alerting the patient or user of warnings and alarm conditions. The user has some control over the selection of audio alarm or vibration while the system can automatically switch from vibration to audio if the vibrational alarm is not responded to in a timely manner. The audio alarm is programmable to emit at different frequencies, at different volume levels, for different durations, and with different repetition patterns. These various alternatives are used to signal different conditions. The vibratory alarm is also programmable to go off for different durations and with differing repetition patterns. In alternative embodiments, only one type of alarm may be used and it may be used with or without different frequencies, volumes, durations, or loudnesses.

The software controlling the external communication device is permanently stored within the external communication device using a non-volatile memory such as a serial electrically erasable programmable read only memory (SEEPROM) and is transferred to random access memory (RAM) for execution. The code being executed in RAM can be reloaded from that SEEPROM as needed. Software located within the SEEPROM can be replaced with new software under controlled conditions. The external communication device is provided with sufficient memory capability to store a duplicate, or upgrade, version of application software for the implantable device as well as to store about 120 days of operational data. Under controlled conditions the external communication device may be reset to its default configuration automatically (i.e. upon command without the user having to specifically identify specific parameter values). In alternative embodiments the software may be stored in a different device (e.g. a physical ROM, volatile RAM, non-volatile RAM, or in a replaceable plug in module). The software may be divided into bootloader and application code portions.

As noted above, the implantable device and external communication device communicate with each other through radio frequency telemetry where reception and transmission within the implantable device uses an antenna that is located within the metalic device housing based on a carrier frequency that allows an acceptable amount of signal to penetrate through the housing and through the human body. In alternative embodiments, an antenna for the implantable device may be placed on the housing or be otherwise located external to the housing so that outgoing and/or incoming signals need not penetrate the housing material. For the present embodiment the preferred frequency is either about 131 kHz or about 262 kHz. The preferred data transfer rate is at about 8200 bits/second. In alternative embodiments, different carrier frequencies may be used, e.g. from tens of kilohertz to thousands of megahertz. Also in alternative embodiments other data transfer rates may be used. The external communication device and implantable device are configured and operate together to provide rapid feedback to the operator. For example, a response to a basal rate or bolus programming telemetry interaction is preferably provided to the patient within no more than 20 seconds and more preferably within less than about 10 seconds, and most preferably within less than about 5 seconds.

Each implantable device and external communication device are preferably assigned unique telemetry identifiers and a particular implantable device and particular external communication device are made to undergo a linking process (alternatively known as a marrying process) so substantive communication (e.g. communications that allow the external communication device to control the medical operation of the implantable device) is limited to a joined pair. The communication link between the external communication device and implantable device provides various levels of checking and confirmation to minimize the possibility of the implantable device receiving and then acting on an erroneous delivery command message. In alternative embodiments unique identifiers may be supplied to only one of the implantable or external communication devices, or even non-unique identifiers may be utilized.

The linking or marrying process is completed prior to a external communication device being allowed to send drug delivery commands or updated software to a particular implantable device. In this embodiment, each time an external communication device is replaced or reset, the marrying process must be repeated. The marrying feature provides the mechanism to configure an implantable device to communicate with a particular external communication device. This is carried out when the implantable device and the external communication device are initially configured. The linking process requires positive assertion from the user indicating that external communication device is linking to the correct implantable device. The linking process starts with the external communication device sending an interrogate message to all implantable devices within range by using a universal identifier. Each implantable device that is within range responds to the external communication device's interrogate message by sending a response that includes patient identity information as stored in that particular implantable device. If the desired implantable device is the first to respond to the interrogate signal, the user can acknowledge his/her desire to link the external communication device and the implantable device. Otherwise, if the first responding implantable device is not the one to be linked to, the patient may indicate so and that particular implantable device identifier is added to a temporary exclusion list and the interrogate message is resent (including the exclusion list). When the interrogate message is received by each implantable device, only those whose identifiers are not in the exclusion list will attempt a response, thereby allowing other implantable devices within range to respond and be heard. Once the correct implantable device is the one that has its response displayed by the external communication device, the user can elect to start the linking process. Once the link is established, the implantable device is made to enter suspend mode and then the user must reprogram all basal rates including temporary basal rates that were in progress, profile basal rates, and delivery patterns. In alternative embodiments, all or a portion of this information may be retrieved from the implantable device, assuming it was programmed previously, but in this particular embodiment as an added measure of safety, it was preferred that these parameters should be reprogrammed so that the user is made to provide a positive assertion that he/she knows the delivery parameters that the implantable device is using. During the linking process the external communication device obtains other data from the implantable device that it requires in performing its operations, e.g. the external communication device obtains stroke volume information for the pulsatile pump and obtains insulin concentration data that is stored in the implantable device.

The sending and receiving of IR signals by the external communication device is based on basic IrDA standards. In the present embodiment, the transfer rate for the IR link is about 115 kbits/second. Of course in other embodiments other baud rates may be used or even automatically selected between. The IR link may be used to (1) upload new software to the external communication device from a second external device, (2) download system operation information to the second external device for further analysis as desired, and/or (3) pass commands/responses to or from a second external device from or to the implantable device. The second external device may be personal computer running appropriate software or a more specialized system. The communications sent over the IR link are based on protocol details that ensure that only intended messages, and correctly received messages, are received and acted upon.

In an alternative embodiment a second or third external communication device may be used in conjunction with the first external communication device or as a temporary or partial replacement therefor. For example, at night, a chest strap, wrist watch, mattress pad, or the like containing appropriate telecommunication capabilities might be used as a relay device to pick up warning signals or other communication signals coming from the implantable device and then to transmit them to the first external communication device or a third external communication device so that a warning may be sounded to wake up the patient, to directly notify emergency personnel of a problem, or to notify other monitoring personnel in a timely manner of medical device operation or patient condition. Such notification may occur using any appropriate telecommunication systems, such as telephonic or internet connections. In the case of directly warning the patient, if the second communication device has sufficient power and functionality it may implement the warning signal directly. The second or third external communication devices may communicate with the first external communication device via RF telemetry, IR communication link, optical link, galvanic connection, inductive communication, or the like.

The implantable device of the present embodiment has various delivery modes. One of these modes is the suspend mode wherein the system is caused to reduce insulin delivery to a clinically insignificant amount (e.g. 1 pump stroke (approximately 0.2 units of insulin assuming a stroke volume of 0.5 microliters and a U-400 insulin concentration) per hour. It is intended that this minimal rate of delivery keep the catheter open. The "suspend mode" mode may be used to interrupt delivery of a bolus, priming bolus, profile basal rate, diagnostic rate, and/or temporary basal rate. The system is programmed to alarm periodically to indicate to the user that the system is delivering insulin at a clinically insignificant rate. The user may exit suspend mode and resume basal delivery. In this embodiment, any bolus that is in progress when suspend mode is asserted is canceled such that any undelivered portion will not be delivered even when suspend mode is cleared. Other than when entering suspend mode through the linking process, if the implantable device is delivering a temporary basal rate when suspend mode is entered, the temporary basal rate duration continues while the pump is in suspend mode, and the temporary basal rate is reasserted when suspend mode is cleared for any portion of the duration that has not already lapsed. Of course in other embodiments other control options may be implemented with regard to going into or coming out of a mode analogous to suspend mode.

The external communication device is programmable using an audio bolus mode. This mode allows a user to program the delivery of a bolus without looking at the external communication device display. This mode provides an audio feedback to the user to indicate the amount of the bolus that is being programmed. The audio bolus feature allows programming of immediate boluses. Immediate boluses are those that specify a quantity of insulin to be delivered in as short a time as possible, e.g. a short as time as necessitated and allowed by any required repeated operation of the pumping mechanism. Under selected conditions a parameter selection may be made that dictates the incremental increase in bolus amount with each successive key entry (e.g. press of the Up-Arrow Key) when in audio bolus mode. Under selected conditions, the external communication device provides another parameter that enables or disables the audio bolus feature. In the present embodiment, once the desired bolus amount has been achieved by the repeated pressing of the select key, the user may confirm the accuracy of the selected amount by pressing a different key (e.g. the ACT key). When this confirmation key is pressed for the first time the external communication device plays a sequence of audio tones so as to indicate the amount programmed. If the amount is correct the user may press the ACT key again to initiate delivery. If the amount is incorrect the user may simply wait a predetermined, but short, period of time for the external communication device to time out or alternatively, the user may press any key other than the confirmation key. A distinct sound is emitted to indicate that delivery was not initiated, at which point the user may simply start over with the audio or visual programming.

Of course in other embodiments, other key press sequences may be used in the performance of programming an audio bolus. Alternatively, if the system were configured with a microphone or other sound transducer and appropriate audio command recognition software or hardware, audio programming could be performed without any keystrokes or with a single keystroke to activate the external communication device's listening mode. In a similar vane, if the external communication device were configured with a sound transducer and appropriate speech enabling hardware and/or software, then instead of sounding a series of beeps to indicate program status, it could communicate to the user, in a predefined language, to indicate the status. In still further alternatives, speech recognition and/or speech generation hardware could be used to replace or supplement keypad or touch screen input capabilities.

In the present embodiment, basal rate delivery and bolus delivery may be programmed to occur in conjunction with each other as opposed to one replacing the other. The system does not replace basal rate delivery with bolus delivery but instead combines the amount to be delivered under basal programming with the amount to be delivered under bolus programming to cause a net amount to be delivered that is equal to the sum of both amounts. The user may program a bolus amount on the external communication device and the implantable device will respond by delivering that amount. The amount of the bolus is subjected to a bolus maximum as described below.

The system allows the user to program an amount to deliver that the implantable device will deliver as quickly as possible using a required number of pump strokes with typically no more than 6 seconds between successive pump strokes (e.g. 1–3 seconds per stroke). This type of bolus is sometimes referred to as an immediate bolus or phase I bolus.

The system allows a bolus to be delivered where the user programs an amount and a duration. The implantable device delivers the amount as a rate (i.e. number of pump strokes per unit time) for the duration specified such that the amount programmed by the user is delivered within the duration. This is analogous to a basal rate or temporary basal rate delivery in some manner but is not identical as the total amount to be delivered is the sum of this amount and any basal rate that is currently in effect. Furthermore, in this delivery mode the user does not program the delivery amount as a rate. This type of bolus is sometimes referred to as a square wave or phase II bolus.

The system supports a "dual wave bolus" where the user programs an amount for immediate delivery (immediate bolus) and a second amount for delivery during a specified duration (square wave bolus). When programmed in this manner the implantable device delivers the immediate amount as described above, followed by delivery of the second amount over the duration as a square wave amount also as described above.

The system also supports delivery of an immediate bolus while delivery of a square wave bolus is in progress or while delivery of the square wave portion of the dual wave bolus is in progress so long as the immediate portion of the dual wave bolus has been completed.

The programming of boluses in the external communication device is further controlled by a variable bolus option. If the variable bolus option is set to "no", only immediate bolus programming is allowed and the square wave and dual bolus options are removed from the menu choices available on the external communication device. If the variable bolus option is set to "yes", immediate, square wave, and dual wave bolus programming are allowed and all menu options are presented to the user.

The implantable device holds a number of logs. One of these logs is a bolus history log. In this log the implantable device maintains the time and amount of boluses that have been delivered. This log contains the most recent boluses that were delivered. This log is set to contain up to a predefined number of boluses after which the log wraps around and deletes older entries in favor of recording new entries. The external communication device receives these records from the implantable device. These records may be viewed on the external communication device or alternatively they may be downloaded to a second external device where they can be viewed in numerical form or be plotted for viewing in graphical form. The storage of this log information in the implantable device ensures that historical information remains available even in the event that the external communication device is lost, damaged, or otherwise fails. Each time a new bolus is programmed from the external communication device and confirmed by the implantable device, the details of the previously delivered bolus are provided back to the external communication device so a log maintained in the external communication device is almost as up to date as the log maintained by the implantable device. The log maintained in the external communication device can be scrolled through for review by the patient or healthcare provider. Each bolus history record includes the amount, time, and date of the bolus delivery.

The implantable device maintains another log that provides the total amount of insulin delivered by date. The implantable device maintains a history of the most recent 120 days of insulin delivery totals with the daily total separated by basal delivery and bolus delivery. The daily totals are downloaded automatically or semi-automatically from the implantable device to the external communication device each day. As with the bolus log, this information is protected from loss or failure of the external communication device by its retention in the implantable device.

The system maintains multiple sets of basal rates where each set dictates basal rate delivery for a selected interval of time and each element in each set dictates the basal rate delivery for a subset of that selected interval of time. In the present embodiment the number of sets is three, the selected interval of time is 24 hours beginning at midnight, and the subset of the selected interval of time is 30 minutes which starts at the beginning of each half hour mark during the day. As such, each set consists of up to 48 rates that can start on any half-hour of the day.

For programming convenience, the delivery rates need not be entered for each subset but instead only for those subsets that represent a change in delivery rate compared to the previous subset. As such, in this embodiment, basal rate values are only entered for the subset half hours in which transitions occur and are entered by specifying the start times and rates. Up to three 24-hour profiles may be entered with only one of the profiles selected as active at any given time. When a profile is made active, information about that profile is communicated to the implantable device to replace any other basal rate information retained there. As an added safety feature, only one profile set is stored in the implantable device at any given time. The active profile is repeatedly used day after day to control basal rate delivery in the implantable device until it is replaced by a different or revised profile. Such basal profile sets may be used for different types of days, e.g. work days, non-work days, exercise days, non-exercise days, sick days, high stress days, and the like.

The system allows a temporary basal rate to replace any profile based basal rates during a specified period. This feature allows the user to program a basal rate without changing the basal profile. When the temporary basal rate duration lapses, the implantable device resumes delivery of the basal profile rate that is then in effect based on the selected profile and the then current time of day. The temporary basal rate, for example, may be utilized to program lower basal rates during periods of exercise, or used to program higher rates during periods of high stress.

Selected "personal events" are recordable by the user in a personal event log. The personal event log is accessed through the external communication device and stored in the external communication device. In alternative embodiments these events may be communicated to the implantable device for safekeeping. The user may record the time that certain events occurred, such as exercising, meals, or illness. A parameter may be set so as to disable personal event logging. When disabled, the option does not present itself on the user menu in the external communication device. In the present embodiment, the system provides sufficient memory and control for retention and review of up to 100 such events.

"Automatic Off" is another feature of this embodiment. When this feature is enabled the insulin delivery system turns itself off if the user does not interact with the implantable device through telemetry for a programmed amount of time. This feature may be enabled or disabled. In this context, the turning off of the implantable device refers to the implantable device going into suspend mode. The implantable device alarms if it goes into minimum delivery mode as a result of the automatic off interval lapsing. The automatic off interval is reset each time the implantable device receives a valid telemetry message from the external communication device intended specifically for it. In order to save battery power in the implantable device, the external communication device is programmed to track the time that elapses between communications and to alarm 5 minutes before the automatic off interval lapses. This enables the user to clear the alarm and interact with the implantable device before the implantable device itself alarms and thus results in reduced power consumption by the implantable device.

An additional parameter of the present embodiment is bolus maximum which specifies the size of the largest single bolus that can be delivered. A pumping operation used in setting up the implantable device, called priming bolus is not subject to this maximum. The external communication device is programmed so that a user can not program an immediate bolus amount greater than the bolus maximum. The external communication device is also programmed so that the sum of the immediate amount and the extended amount of a bolus (regardless of the duration) may not exceed the Bolus Maximum. The implantable device uses the bolus maximum as a safety check of each bolus request that is received from the external communication device.

The external communication device is programmed to sound a maximum alarm if the user attempts to deliver an amount of insulin during a predefined period that exceeds a predefined limit. In this embodiment the predefined period of time is one hour and the maximum alarm is termed the hourly maximum alarm and the predefined limit is 2.5 times the Bolus Maximum. This alarm is intended as a safety alert to the user and not as an absolute limit on the amount that can be dispensed in any one hour period. The external communication device is programmed to compute the total amount of bolus delivery during the previous one hour period each time a bolus is programmed. If the amount already delivered summed with the programmed amount exceeds 2.5 times the programmed bolus maximum, the external communication device alarms and the bolus is not allowed. When an hourly maximum alarm is cleared, there is a short window where the user may program a bolus that normally would trigger an hourly maximum exceeded alarm. Following the short window, bolus programming is subject to the hourly maximum limitation and warning again. In the present embodiment the short window is set at ten minutes. In the present embodiment both amounts programmed for an immediate and square wave boluses are considered in triggering the hourly maximum exceeded alarm regardless of when the extended bolus amount was or is to be delivered. In alternative embodiments, the external communication device may be programmed to take into account quantities that have or will be delivered within a one hour period based on the programmed amounts and time intervals. In other embodiments the maximum amount in the predefined period may be determined based on something other than the maximum bolus amount. In still further embodiments the maximum bolus amount may be implemented as a hard limit. In still further embodiments, a second or subsequent bolus programmed in the same short window would not be subject to the warning. In other embodiments, the external communication device could not only warn the patient that the maximum amount has been exceeded but would also indicate the amount that was delivered in the period being considered.

External communication device programming and implantable device delivery are also limited by a basal rate maximum which is the highest rate that may be delivered using a profile basal rate or a temporary basal rate. A delivery rate used for diagnostic purposes known as the diagnostic rate is not subject to this maximum. The external communication device is programmed to inhibit the user from entering a basal rate greater than the basal rate maximum. The implantable device uses the basal rate maximum as a safety check of each basal rate that is programmed. The implantable device ignores delivery requests that include basal rate amounts greater than the basal rate maximum. The external communication device is configured to inhibit the user and physician from setting a maximum basal rate that is less than any of the basal rates already programmed including those in the profiles that are not currently active.

The external communication device is capable of displaying an estimate of the amount of medication remaining in the insulin reservoir. The external communication device is programmed to alarm when the medication remaining becomes less than a predefined low-reservoir threshold. As with other alarm conditions in the system, low-reservoir threshold alarms are reasserted after clearing if appropriate actions have not been taken to resolve the condition that gave rise to the error or event (e.g. refilling of the reservoir has not been completed). Once the low-reservoir alarm is cleared, and a predetermined period of time has lapsed and the system determines that the reservoir has not yet been refilled, the alarm will be reasserted so as to provide the user with a reminder to have the reservoir refilled.

The implantable device and external communication device retain clinical history information as records of various events that the system tracks. For example, events that stop the delivery of insulin such as alarms are recorded in the clinical history. User-initiated events such as suspend mode that stop the delivery of insulin are also recorded. Refills are also recorded. The system also contains logs for system diagnostics such as implantable device battery levels. Through menu options the user may view these various history logs.

In this embodiment, the system is programmed to allow a user to initiate a self test in both the external communication device and the implantable device. If there are any error conditions detected, they are reported to the user. The system self test includes a number of different checks: (1) implantable device memory, (2) external communication device memory, (3) implantable device piezo operation, (4) external communication device piezo operation, (5) external communication device vibrator operation, and (6) external communication device display. If an error is detected, the system reports the error to the user using visual, vibrational or audio alarms.

The external communication device is configured to emit audio alarms, or to vibrate, in the event an alarm condition exists. The implantable device always emits an audio alarm if an error condition persists beyond a predefined amount of time based on the particular alarm condition that exists. The external communication device is configured to allow the user to selected audio or vibration notification when alarm conditions exist. For many alarm conditions, the implantable device is programmed to contact the external communication device by telemetry prior to sounding an alarm on its own. In the event that the external communication device receives the message and successfully notifies the user of the condition and the user clears the alarm prior to a predefined time period passing, the implantable device does not sound the alarm directly on its own. In the event that the alarm condition is cleared but not resolved, the implantable device may directly reassert and sound the alarm later or may reassert and recontact the external communication device through telemetry.

The system supports an audio feedback mode where the implantable device may be programmed to beep on a first predefined number (e.g. 3–10 pump strokes after a rate change, and for a first predefined number (e.g. 3–10) pump strokes of a bolus. In other alternative embodiments, other feedback techniques may be implemented.

The system supports a storage mode for the implantable device and for the external communication device. Storage mode in the implantable device is a state where there is no drug delivery and no alarms and the frequency of waking up to listen for incoming telemetry messages is reduced. Storage mode in the external communication device is a state where the screen is blank and no user functions are available. The implantable device is programmed to enter storage mode upon receipt of a particular telemetry command. The implantable device is programmed to exit storage mode by receipt of a particular telemetry command. There is no implantable device alarm that indicates that the implantable device is entering storage mode.

The external communication device is programmed to enter storage mode if there is no user interaction with the external communication device for an extended period of time (e.g. 5–10 days). The external communication device is programmed to exit storage mode in the event of user interaction with external communication device such as button presses. When the external communication device is in storage mode the screen is blank and the external communication device hardware is put into a low-power state.

The system allows refilling of the pump and reporting on delivery accuracy. The system is programmed to allow entry of an extracted volume and a fill volume during the refill process. The external communication device may be made to display delivery accuracy based on a difference between the expected amount remaining in the insulin reservoir and the actual amount of insulin removed during the refill process.

In the present embodiment, the system is configured to support user and physician programming of the delivery options using insulin units based on a desired resolution value not based on a predetermined pump stroke volume. When the external communication device is programmed to deliver a certain amount of insulin, the external communication device calculates the number of pump strokes necessary to deliver that quantity and passes the pump stroke information onto the implantable device. The pump stroke information is passed in fixed point format including both an integer portion and a fractional portion. The determination of pump strokes is based on the implantable device pump stroke volume and the insulin concentration.

The system of this embodiment is configured to allow a programming option to be set that allows the physician to prime the catheter quickly. As will be discussed further hereafter, this option is only available as a supervisor function. The priming function/option triggers the implantable device to deliver an amount of insulin large enough to fill the catheter. In this mode, pump strokes are delivered as fast as possible. The physician is notified when the priming bolus is completed.

The system supports a special rate called diagnostic rate that is only programmable as a "supervisor only" function. This special rate is used in determining delivery accuracy. The diagnostic rate function triggers the implantable device to deliver at a programmed rate that is not subject to the basal rate maximum.

In this embodiment, the setting of system maximum basal rate and maximum bolus amounts may be programmed to be inaccessible to the patient and only accessible through a supervisor menu. The patient's ability to access these maximum values is controlled by a maximum lock parameter that is a supervisor function. When the maximum lock feature is enabled, the user may view, but not change, the bolus maximum and the basal rate maximum. When the maximum lock feature is disabled, the user may change the bolus maximum and the basal rate maximum.

The system includes memory space and program capability to personalize the external communication device and implantable device so that information such as the patient name and physician name can be stored for later retrieval and review. For example, the personal ID may be as little as 10 characters and as much as 200 characters or more. In the linking process it is preferred that at least a portion of this information be used in determining that the external communication device has contacted the desired implantable device (assuming the implantable device has already been previously programmed with identity information. When identification information is updated in the external communication device it is passed on to and stored in the implantable device.

The system retains factory default information and may be reset to those values when operating under supervisor control so that the system may be configured rapidly to a known state. The system may also be placed in a stop mode or controlled to replace or reload implantable device software when operating under supervisor control.

As noted above certain system functions require special control and their access is restricted. These features are only accessible via a supervisor menu on the external communication device. The supervisor menu is password protected. The password may be set by the physician while in supervisor mode. The supervisor menu system may also be entered by using a factory password. The factory password may be derived from the system characteristics. For example, the factory password may be a fixed number or character pattern. It may be based on a variable parameter, such as the date reflected by the external communication device, and/or the time reflected by the external communication device, and/or the serial number of the external communication device. Supervisor options/functions include the following: (1) refill, (2) priming bolus, (3) diagnostic rate, (4) maximum lock, (5) personal ID setting, (6) initialize to factory defaults, (7) download implantable device software, (8) stop pump, and (9) set supervisor password.

The user interface uses four keys, e.g. a SEL, ACT, UP and DOWN key, to navigate through menus, display options and features, and to program values. The external communication device changes the display to the idle display which shuts off the bit map display if the external communication device keypad is idle for a predefined period of time, preferably between 2 seconds and 30 seconds, more preferably between 4 seconds and 15 seconds and more preferably between 5 seconds and 10 seconds ,e.g. 7 seconds, while the user is viewing options. The external communication device may change the display to the idle display using a different predetermined time, e.g. a longer time such as 15 seconds, if the external communication device is idle while the user is in a programming or data entry screen.

As noted previously the system is programmed to display the current time and date. The time may be displayed in either a 12-hour or 24-hour format depending on user preference though in either event internal calculations that require time are based on a 24 hour clock.

All time displays by the external communication device are shown in the same format including time stamps on historical data and profile start times. This format in the present embodiment is based on a relative time measured in minutes since the factory initialization of the implantable device.

Acceptable parameter ranges for selected variables used in this first embodiment are depicted in the following table. Of course, in other embodiments other ranges are possible, other programming units may be used, some parameters may be converted to constants while other parameters may be added as variables.

Acceptable Parameter Ranges

| Parameter Name | Values |
| --- | --- |
| Automatic Off Duration | Off, 1–16 hours |
| Audio Bolus Increment | 0.4 units or 0.8 units |
| Bolus Amount | 0.2 U to Bolus Maximum by 0.2 U |
| Bolus Duration | 30 min to 4 hours |
| Maximum Bolus | 0.2 U to 35.0 U by 0.2 U |
| Hourly Maximum Bolus | 2½ times the programmed Maximum Bolus |
| Basal Rate | 0.2 U/hr to Basal Rate Maximum by 0.1 U/hr |
| Temporary Basal Rate | 0.2 U/hr to Basal Rate Maximum by 0.1 U/hr |
| Temporary Basal Rate Duration | 30 min to 24 hrs by 30 min |
| Basal Rate Maximum | 0.2 U/hr to 35 U/hr by 0.1 U/hr |
| Diagnostic Rate | 10 to 150 u/hr by 10 u/hr in U-400 |
|  | 10 to 185 u/hr by 10 u/hr in U-500 |
| Insulin Concentration | U-400 or U-500 |

As noted above, both the implantable device and the external communication device detect and report alarm conditions. The following table depicts examples of different types of alarms and examples of associated delivery states that are entered in response to the condition that gave rise to the alarm.

Alarm Conditions

| ALARM | Alarm Condition | Alarm State Action |
| --- | --- | --- |
| Low Battery | Alarm when there is battery energy remaining of about 8 weeks or less | Alarm Only/ Icon ON |
| Depleted Batter | None guaranteed | No Delivery |
| Low Reservoir | Alarm when 2 mL of drug remaining | Alarm Only/ Icon ON |
| Empty Reservoir | Alarm when 1 mL of drug remaining | Alarm Only/ Icon ON |
| Any implantable device Hardware Failure Detect | Alarm | No Delivery |
| Over Delivery | Alarm when disagreement from various delivery calculations produces a discrepancy of a first type. | No Delivery |
| Under Delivery | Alarm when disagreement from various delivery calculations produces a discrepancy of a second type. | No Delivery |
| Self Test Failure | Alarm when the periodic self test including the memory test fails | No Delivery |

As noted above, even when an alarm is initially cleared, it may be reasserted if the condition that gave rise to it continues to persist. When a condition persists, the reassertion of and sounding of the alarm may occur for example as indicated in the following table.

TABLE 1

Alarm Reassertion Intervals

| Exception | Reassertion | Internal Beep | Menu Options Disabled | Persistent Icon/Message Display |
| --- | --- | --- | --- | --- |
| Over Delivery | 0 | 5 min | Yes | Yes |
| Under Delivery | 0 | 5 min | Yes | Yes |
| Low Implantable Device Battery | 7 Days | 24 Hrs | N/A | Yes |
| Low Reservoir | 24 Hrs | 24 Hrs | N/A | Yes |
| Empty Reservoir | 24 Hrs | 24 Hrs | N/A | Yes |
| Depleted Implantable Device Battery | N/A | N/A | N/A | N/A |
| Automatic Off | N/A | 5 min | N/A | Yes |

In this embodiment, physical and functional features have been considered as well as implantable longevity. In addition to the various features noted above, the implantable device and external communication device preferably meet certain physical targets: (1) The implantable device is preferably packaged in disk shaped housing that is thinner than about 1 inch, and preferably thinner than 0.9 inches, and more preferably thinner than about 0.8 inches or less, with a diameter of less than about 4 inches and more preferably about 3.2 inches or less, and having an empty weight of less than about 180 grams and more preferably less than about 165 grams, and (2) The external communication device has been packaged in a somewhat rounded but nominally rectangular shaped package having dimensions of less than about 1.0 inch by 3.5 inches by 4.0 inches, but more preferably having dimensions about 0.8 inch or less by about 2.8 inches or less by about 3.5 inches or less, and weighing less than about 6 oz. In other embodiments, various other device shapes and sizes may be used.

The implantable device and external communication device are preferably also designed and are controlled to meet certain longevity requirements in combination with the desired functional requirements. It is desired that the implantable device remain operational within the body of a patient for a period of about five years or longer, more preferably a period of about seven years or longer, and most preferably a period of about 9 years or longer. As the present embodiment uses a non-rechargeable battery, the longevity of the implantable device is primarily dictated by the power consumption of the electronic modules and the capacity of the battery. The determination of longevity is complicated by the fact that the power consumption of the electronic modules is not constant over time but varies depending on the actions that are required by the user. Two elements of the preferred embodiment that lead to an acceptable level of longevity are the use of low power electronic circuit elements and the controlled application of power and/or clocking signals to various modules. The power and/or clocking signals are supplied to the modules on an as needed basis and operational protocols have been put into place to minimize the amount of time that the various modules need to operate. As noted previously, an example of such protocols include the implantable device's attempt to communicate with the external communication device by telemetry prior to using a more power consumptive internal alarming process. Another example involves the implantable device having a storage mode that uses less power than a normal operational mode. A further example includes the implantable device's process of turning on its receive telemetry for short periods of time (about four milliseconds) on a periodic basis (once every two seconds) to listen for incoming messages and then shutting off the telemetry system if no messages are incoming. An additional example, includes the processor's ability to turn itself off when it is not needed and to be awakened by interrupt signals when needed. These and other examples of controlled power consumption are discussed further hereafter.

Figure 3:
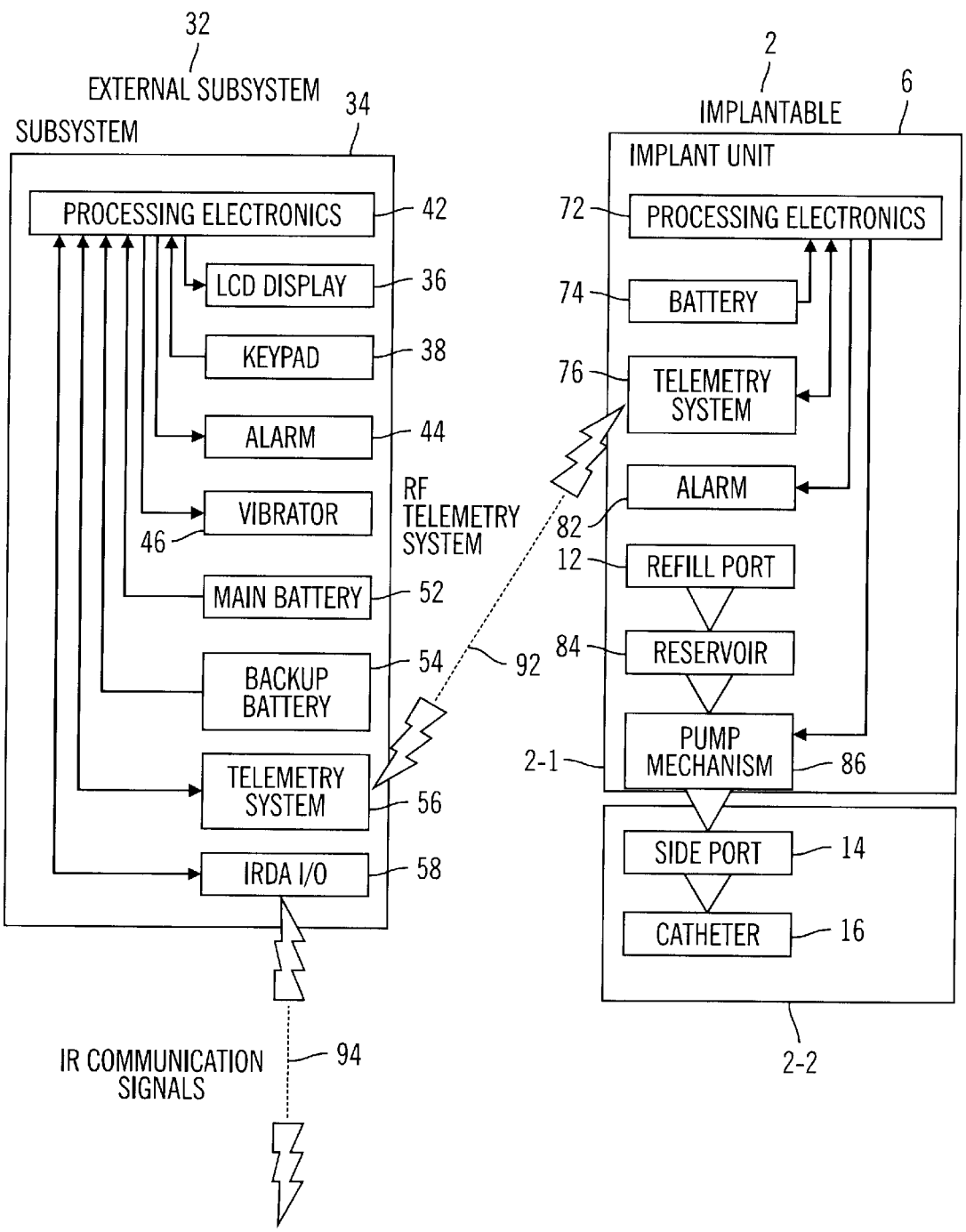
FIG. 3 depicts a block diagram of the main components/modules of both the implantable device and the external communication device of the first preferred embodiment.

FIG. 3 depicts a simplified block diagram of various functional components or modules (i.e. single components or groups of components) included in the implantable medical device 2 and external communication device 32. The external communication device 32 includes (1) a housing or cover 34 preferably formed from a durable plastic material, (2) processing electronics 42 including a CPU and memory elements for storing control programs and operation data, (3) an LCD display 36 for providing operation for information to the user, (4) a keypad 38 for taking input from the user, (5) an audio alarm 44 for providing information to the user, (6) a vibrator 46 for providing information to the user, (7) a main battery 52 for supplying power to the device, (8) a backup battery 54 to provide memory maintenance for the device, (9) a radio frequency (RF) telemetry system 56 for sending signals to the implantable medical device and for receiving signals from the implantable medical device, and (10) an infrared (IR) input/output system 58 for communicating with a second external device.

The second external device may include input, display and programming capabilities. The second device may include a personal computer operating specialized software. The computer may be used to manipulate the data retrieved from the communication device or the medical device or it may be used to program new parameters into the communication device or directly into the medical device, or even used to download new software to the communication device or to the medical device. The manipulation of the data may be used in generating graphical displays of the data to help aid in the interpretation of the data. Such data interpretation might be particularly useful if the medical device provides data concerning a physiological parameter of the body of the patient, such as a glucose level versus time. More particularly the computing power and display attributes of the second device might be even more useful when the medical device includes both an implanted sensor (e.g. glucose sensor), or external sensor, and an implanted pump (e.g. insulin pump), or external pump, where the second external device may be used to enhance the ability to ascertain the effectiveness of the two devices working together. Successful control periods and problem control periods could be more readily identified. In fact, if the two devices work on a closed loop basis or semi-closed loop basis, the analysis performable by the second external device may be useful in deriving new closed loop control parameters and/or in programming those parameters directly into the communication device or the medical device or devices.

The implantable device 2 includes (1) a housing or cover 6 preferably made of titanium that may or may not be coated to enhance biocompatibility, (2) processing electronics 72 including two CPUs and memory elements for storing control programs and operation data, (3) battery 74 for providing power to the system, (4) RF telemetry system 76 for sending communication signals (i.e. messages) to the external device and for receiving communication signals (i.e. messages) from the external device, (5) alarm or buzzer 82 for providing feedback to the user, (6) refill port 12 for accepting a new supply of drug as needed, (7) reservoir 84 for storing a drug for future infusion, (8) pumping mechanism 86 for forcing selected quantities of drug from the reservoir through the catheter to the body of the patient, (9) sideport 14 for providing a replaceable connection between the (10) catheter and the pump housing and for allowing diagnostic testing of the fluid handling system to occur, and catheter 16 for carrying medication from the implant location to the desired infusion location.

In this embodiment, the pump mechanism is preferably a low power, electromagnetically driven piston pump. Such as for example Model Nos. P650005 or P650009 as sold by Wilson Greatbatch Ltd. of Clarence, N.Y. which have stroke volumes of 0.5 microliters and draw under 7 mJ (e.g. about 6 mJ) per pump stroke and under 4 mJ (e.g. about 3 mJ) per pump stroke, respectively. The pump mechanism dispenses a sufficiently small volume of insulin per stroke so that a desired level of infusion resolution is achieved. For example if an infusion resolution of 0.2 units of insulin were desired when using U400 insulin, then a stroke volume of about 0.5 microliters would be appropriate. In other embodiments other types of infusion pumps may be used, e.g. peristaltic pumps, screw driven pumps, and the like.

As depicted in FIG. 3, the implantable device includes a reservoir 84 for holding a desired quantity of insulin. In this embodiment, the drug held in the reservoir is preferably maintained at a slight negative differential pressure (with respect to the pressure on the outside of the housing) so that in the event of a leakage in the reservoir 84 or housing 6, the drug will not be forced from the housing into the body of the patient. The drug is added to the reservoir 84 by means of a transcutaneous needle that is passed from a position exterior to the body into self sealing refill port 12. Due to the slight negative pressure that the reservoir experiences, insulin in a syringe connected to the needled is drawn into the reservoir without need of external force. The drug is extracted from the reservoir 84 and forced through catheter 16 by an electronically controlled pump mechanism 86. In alternative embodiment positive pressure reservoirs may be used in combination with pumping mechanisms that force the medication or drug from the implantable device and/or used with flow restrictors that dispensed the drug at a fixed rate or at a variable rate with the aid of valves or flow diverters.

The size of the reservoir is preferably large enough to hold sufficient insulin so that refilling does not have to occur too often. For example, it is preferred that time between refills be within the range of 1.5–4 months or longer, more preferably at least 2 months, and most preferably at least 3 months. Opposing the containment of a large volume of insulin, is the desire to keep the implantable device as small as possible. In the present embodiment the implantable device and reservoir has been designed to hold about 13 ml of insulin. A preferred insulin has a concentration of 400 units per milliliter and is available from Aventis HOE 21 Ph U-400 from Aventis Pharma (formerly Hoechst Marion Roussel AG, of Frankfurt am Main, Germany). This insulin is a highly purified, semi-synthetic human insulin with 0.2% phenol as a preserving agent, glycerol as an isotonic component, TRIS as a buffer, plus zinc and Genopal® as stabilizing agents. This quantity and insulin concentration allows about 2–4 months between refills. In other embodiments higher insulin concentrations may be used (e.g. U-500 or U-1000) to increase time between refills or to allow reduction in reservoir size. In some embodiments, when higher concentrations are used, any quantized minimum delivery amounts may be reduced by modifying the pumping mechanism, control circuitry, or software control algorithm so that infusion resolution is not adversely impacted.

The external communication device contains appropriate software to provide proper control of the device including appropriate functionality to allow communication with the medical device, to allow adequate control of the operation of the medical device, and to give appropriate feedback to the user regarding overall system operation. The medical device is provided with appropriate software to allow communication with the external communication device, to allow safe and appropriate operation of the medical functionality of the device, and to allow direct feedback to the user concerning device status via the internal alarm.

The control electronics of both the implantable device and external communication device are centered around microprocessor based integrated circuits, i.e. processor ICs, that are implemented in the present embodiment in the form of application specific integrated circuits (ASICs). Two such ASICs are used in the implantable device to increase operational safety of the device by configuring the device to require that the two ASICs act in conjunction with each other in order for medication infusion to occur.

In different embodiments, more or less of the control electronics may be implemented within one or more processor ICs while any remaining portions may be implemented external to the processor IC(s). The processor IC may be referred to as an MD processor if used in the medical device portion of the system or a CD processor if used in the communication device portion of the system. In other embodiments the process IC used in the communication device may be different, e.g. have a different CPU or different peripheral modules, from a processor IC used in the medical device. In embodiments where more than one processor IC is used in either the medical device or the communication device each of the processors may be different. They may be specifically designed for their intended roles when they perform at least partially different functions. Depending on particular design constraints portions of the electronics not embodied in the processor ICs may form part of one or more hybrid circuit boards or be otherwise mounted within, on, or even in some cases external to a device housing.

Figure 6:
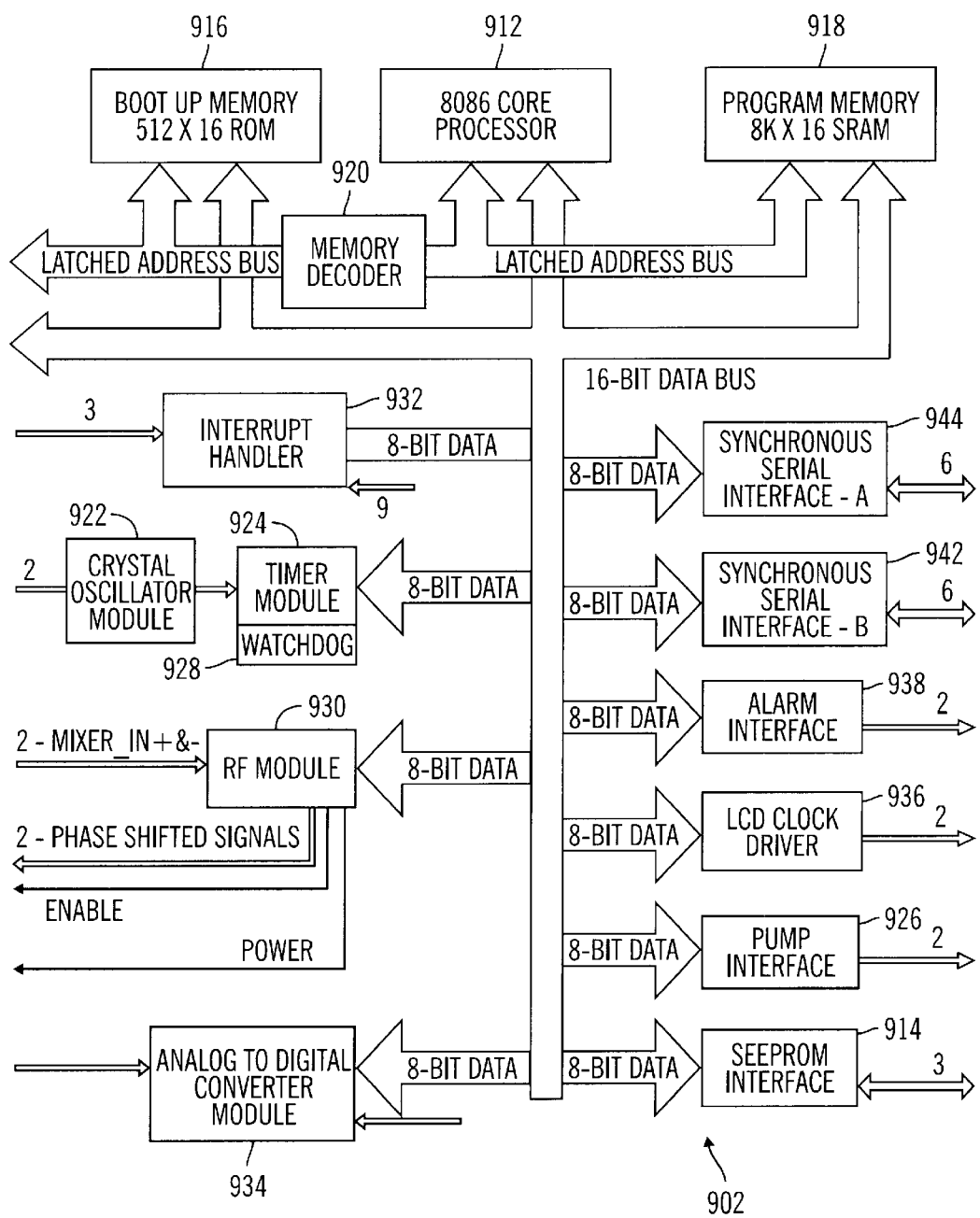
FIG. 6 depicts a block diagram of the various modules of the processor IC used in both the implantable device and the external communication device of the first preferred embodiment.

A functional block diagram of the Processor IC for the present embodiment is depicted in FIG. 6. Each processor IC of the present embodiment includes a CPU 912 and various peripheral modules that are used for system control, data acquisition, and interfacing with electrical components external to the processor IC. The peripheral modules of the processor IC of the present embodiment include (1) a non-volatile memory interface module, e.g. a SEEPROM interface module 914, (2) a boot ROM module 916; (3) an SRAM module 918; (4) a memory decoder module 920; (5) a crystal oscillator module 922; (6) a timer module 924; (7) a pump interface module 926; (8) a watchdog module 928; (9) an RF telemetry module 930; (10) an interrupt handler module 932; (12) an analog-to-digital converter module 934; (13) an LCD clock driver module 936; (14) an alarm interface module 938; and (15) first and second synchronous serial interface modules 942 and 944. The memory decoder module interfaces with the core processor, boot ROM, and internal SRAM using a 16 bit address bus which also is available off chip for addressing external memory. With the exception of the crystal oscillator module all other internal module communicate over an 8-bit data bus or 16-bit data bus. FIG. 6 further illustrates that the A/D module may take input from sources internal to the processor IC and similarly the interrupt handler can take up to 9 interrupts from sources internal to the processor IC. Additionally, most of the modules communicate with outside components or modules over one or more input/output lines.

In alternative embodiments fewer, additional, or different peripheral modules may be incorporated into the processor ICs. In one extreme the processor IC may simply incorporate a CPU with all other modules being external thereto. In the other extreme almost all, if not all, electronic components may be incorporated into a single processor IC. Intermediate alternatives might incorporate a single additional module into the processor IC (in addition to the CPU), others might incorporate more than one, e.g. 4 or more, 8 or more, or the like. In still other alternatives, the number of peripheral modules or components in an entire device may be considered and more than a certain percentage of them incorporated into one or more processor ICs, e.g. more than 50%, more than 75%, or even more than 90%.

The processor ICs are responsible for basic system management and communication of information between the implantable device and the external communication device through the RF telemetry link. The telemetry systems of the present embodiment are implemented in part through electrical hardware and in part through software controlled by a processor IC.

In the present embodiment, most of the required electrical modules for the implantable device are integrated within the processor ICs. However, several are not. These additional modules include two independent crystal oscillators (one for each ASIC); two non-volatile memory modules (one for each ASIC), e.g. SEEPROM chips; a volatile memory module (used only by one of the ASICs), e.g. an SRAM chip; pump driver circuitry (partially controlled by the each ASIC); front end telemetry system circuitry; and voltage measurement circuitry associated with the pump driver circuit; a buzzer; and a battery.

Within the implantable device telemetry operations are controlled by a single ASIC (sometimes known as the main processor). The other processor (sometimes known as the monitor processor) controls the buzzer and is thus responsible for audio communications coming from the implantable device. The medical functionality of the implantable device (i.e. the administration of insulin in the present embodiment) is controlled by both processors. To maintain the implantable device in a fail-safe operational mode, these two processors must maintain an appropriate level of agreement concerning infusion instructions or a system reset is forced to occur. The main and monitor processors communicate with each other through the use of hardwired serial input and output ports.

As with the implantable device, the control electronics of the external communication device are centered around an ASIC that controls and interacts with a number of peripheral modules. These peripheral modules include an LCD display and driver, an IR port and driver, a crystal oscillator, a keypad and keypad interface, power management modules and reset circuitry, external volatile memory (e.g. SRAM) and non-volatile memory (e.g. SEEPROM), a buzzer, and front end telemetry hardware.

The external communication device (CD) is a hand-held device that allows a user to program and communicate with the implantable device. The external communication device of the present embodiment preferably has a weight of less than about ounces, a thickness of less than about 0.8 inches, a width of less than about 2.8 inches, and a length of less than about 4.0 inches.

Figure 4A:
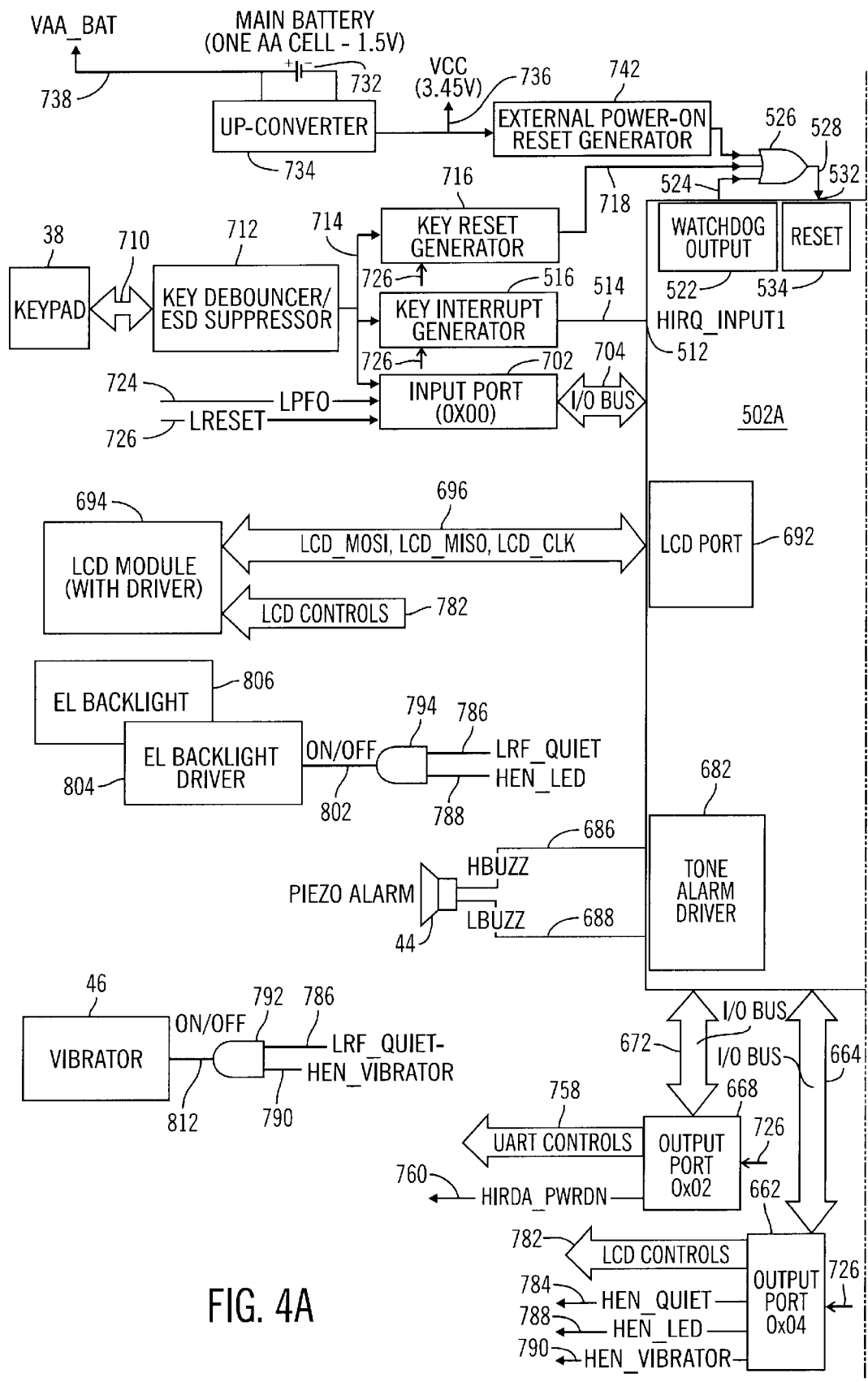
FIGS. 4a and 4b depict a block diagram of the main components/modules and their inter-connections as used in the external communication device of the first preferred embodiment.
Figure 4B:
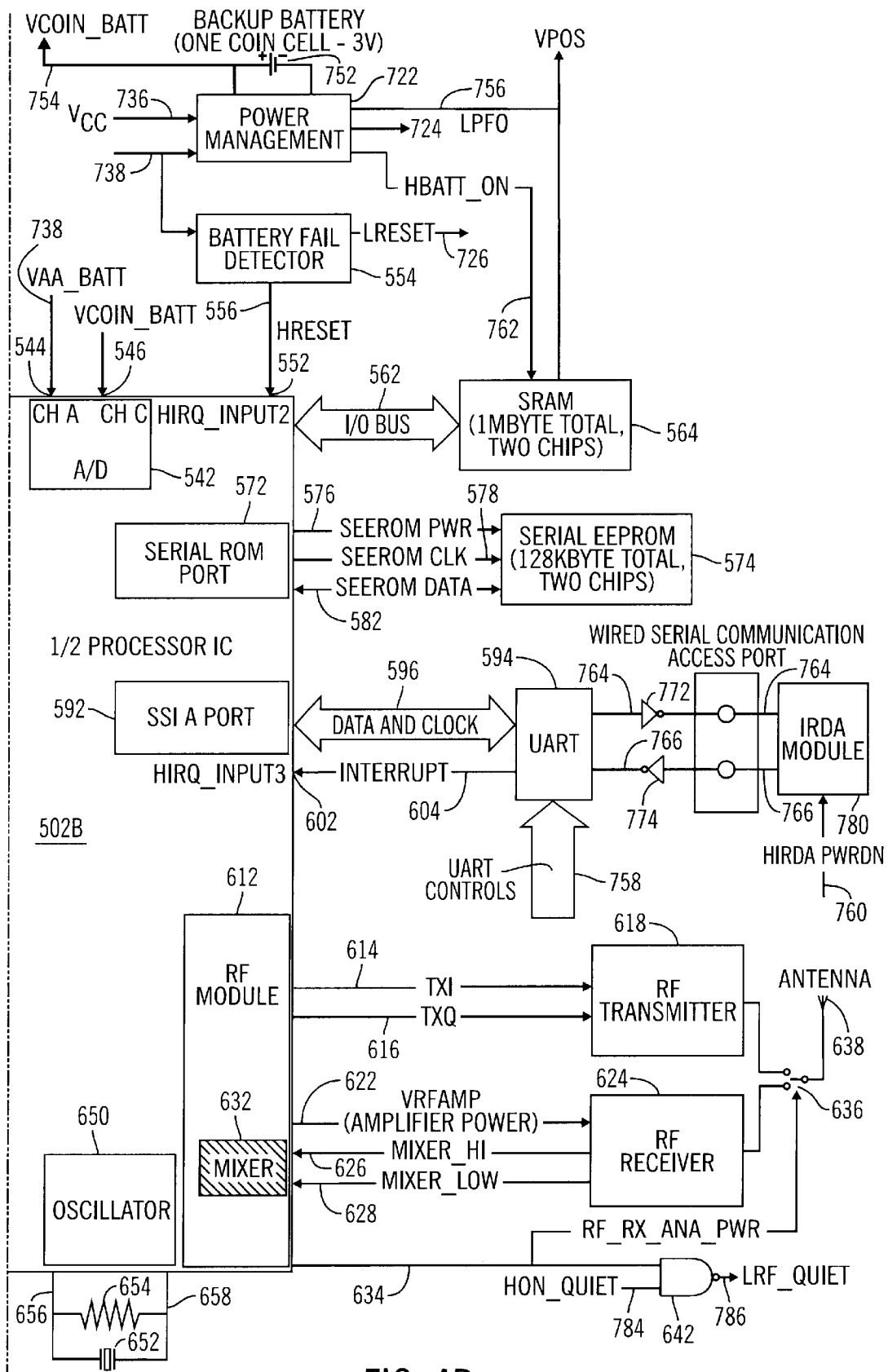

The external communication device is enclosed by housing 34 as depicted in FIG. 2 and includes within housing 34 a number of different electronic modules or components. These modules and a high level outline of their interconnections are depicted in FIGS. 4a and 4b. FIGS. 4a and 4b, form the left and right halves of a single block diagram. The electronic configuration of the external communication device is centered on an ASIC 502 which has been divided for presentation purposes into left and right halves 502a and 502b.

The ASIC 502 includes a microprocessor, internal ROM, internal RAM and a number of additional modules. A number of the ASIC modules used by the external communication device are depicted in FIGS. 4a and 4b. These modules include (1) a watchdog 522, (2) an external reset 534, (3) an A/D converter 542, (4) a serial ROM port 572, (5) a first serial synchronous interface port 592, (6) an RF module 612, (7) an oscillator module (650), (7) a tone alarm driver 682, and (8) LCD port 692, (9) three interrupt inputs, and (10) a number of I/O buses. According to this first embodiment, the preferred ASIC for use in the external communication device is identical to the ASICs used in the implantable device. Further details about the ASIC are provided hereafter.

The ASIC includes a first interrupt input 512 that receives interrupt signals 514 generated by a key interrupt generator circuit 516.

The ASIC includes a watchdog 522 and watchdog output 524 that is fed into "OR" logic circuitry 526 that effectively performs an "OR" operation on three different signals. An output signal 528 of the OR logic circuitry 526 is fed into an input 532 of the ASIC which in turn is connected to reset circuitry 534 that triggers the Processor IC to be reset. The Processor IC can be reset by making any of the three signals high which in turn will drive the output of the "OR" logic circuitry high and thus the input 532 high. The watchdog output signal 524 is made to go high when the processor does not reset the watchdog in a timely manner.

The ASIC includes analog-to-digital converter electronics 542 that uses two external inputs 544 and 546 which are used, respectively, for measuring a voltage (VAA) of a main battery and a voltage (VCOIN) of a backup battery.

The ASIC includes a second external interrupt input 552 that is connected to battery failure detection circuitry 554 by line 556 that carries a high reset signal.

The ASIC includes an I/O bus 562 for carrying address, data and control signals to and from 1 megabyte of external SRAM 564 located on two external chips. Each chip is a four megabit, low power SRAM, organized as 256k by 16 bits, operating between 2.7 and 3.6 volts, with a maximum standby current of 15 $\mu A$. This memory may be accessed either byte-wide or word-wide, as controlled by two external ram signals from the ASIC. Furthermore, an additional two signals from the ASIC are used for chip selection and a third additional signal is sued for bank selection. The third additional signal uses the same output as did the pump fire signal on the monitor processor in the Implantable Device. I/O bus further provides 17 address lines and 16 data lines.

A power management module 722, to be further discussed hereafter, produces a back up battery power signal 762 that goes high when the main battery 732 fails and power is being supplied by the back up battery 752. When the signal 762 is high, access to the SRAM chips is disabled and thus memory access is denied. This is implemented to prevent memory access during unstable periods and to tri-state the memory chip outputs so they are not driving low impedance inputs when boosted voltage 736 (VCC), coming from up-converter 734 that is powered by the main battery 732, fails.

The 762 signal and one of chip selection signals (depending on the SRAM chip being selected), are provided to the inputs of an OR gate and the signal from the OR gate (not shown) is the control signal that is passed to the SRAM. As such, for the particular SRAM chip to be accessible both these signals must be in their low states.

These memory chips are powered by power signal 756 (VPOS) that is derived from VCC when it is available and from the backup battery when VCC is not available.

The ASIC includes a SEEPROM port 572 that is used to connect to two external SEEPROMs 574 using a power output signal 576, a clock output signal 578, and a bidirectional data communication line 582. The SEEPROMs may be identical chips, for example. They preferably have a two wire interface, are internally organized as 64k by 8 bits, support bidirectional data transfer, and use an operating voltage between 1.8 and 3.6 volts. These chips are used to provide memory space for program code and program data. The addresses of these two SEEPROM chips are set by hard wiring. Each chip has a capacity of 64K bytes, organized as 512 pages of 128-bytes each. Each SEEPROM is configured so that it can be written to as well as read from during run time by the system processor.

In the present embodiment one of the SEEPROMs is used for storing external communication device software which is loaded into internal RAM or external RAM during system boot up, while the other SEEPROM is capable of holding software for download to the implantable device.

The ASIC includes a first synchronous serial interface port 592 that is functionally connected to an external UART 594 using several lines 596, including a single clock line for both incoming and outgoing data, a data-in line for data coming from the UART to the Processor, and a data-out line for data going to UART.

A third external interrupt input 602 for the ASIC is connected to UART 594 by line 604. A high signal is generated on line 604 by the UART chip whenever serial data is received through the IrDA port.

The ASIC also provides an RF telemetry module 612 which provides TXI and TXQ signals, on lines 614 and 616, to RF transmitter circuitry 618. The RF telemetry module also provides a power signal 622 to RF receiver circuitry 624. The RF receiver circuitry provides a first and second mixer input signals, 626 and 628, respectively, back to a mixer 632 in the RF telemetry module 612. The RF module also provides a control signal 634 to switching circuitry 636 that effectively connects either the RF transmitter circuitry to an antenna 638 or RF Receiver circuitry to the antenna 638. The control signal 634 is also provided to a NAND gate 642.

The RF telemetry system in the external communication device is similar to that of the implantable device in overall configuration and in control though some differences in circuit detail do exist. The RF system uses a carrier frequency of about 250 kHz (e.g. 262,144 Hz+/−125 Hz). The RF telemetry subsystem is composed of analog and digital modules. The digital module includes a QFAST® modulator/demodulator, a control and timing logic circuit that are integrated in the Processor IC.

The analog module consists of an RF front-end circuit and a mixer. The mixer is also integrated in the processor IC. The RF front-end circuit consists of RF transmitter circuitry and RF receiver circuitry, which is in-turn composed of a band-pass filter and a 3-stage amplifier.

The RF receive circuitry and transmit circuitry share the same antenna 638. The antenna 638 is a faraday-shielded, air-coil, housed within the housing of the external communication device. The antenna and the faraday shield are connected to the printed circuit board.

The antenna is switched between transmit and receive functions in a similar manner to that described above with regard to the implantable device. Switch 636 is similar to switch 234 of the implantable device and includes a tristate driver and an analog switch. The switch is also controlled in an analogous manner. The transmitter 618 is substantially the same as that described above for the implantable device.

The RF Receiver 624 is similar to that used in the implantable device. As with the implantable device, the RF Receiver module 624 includes three amplifier stages that are tuned to pass and amplify desired signals. In contradiction to the implementation in the implantable device, all three stages of in the external communication device are tuned. The first stage has its frequency response set by a tank circuit with tuning adjustable by a variable capacitor. The signal from the tank circuit is passed through a direct current voltage blocking capacitor and then on to a pair of transistors in a push-pull configuration. The transistors may be identical to those used in the implantable device. The second and third stages use tuned push-pull transistor configurations.

The signal resulting from these three stages has preferably been amplified by 70 to 90 dB with an RF passband of about 16 kHz (e.g. about $2^{14}$ Hz) centered around a 262,144 kHz carrier at the 2 dB ripple peak-to-peak maximum. An RF stopband of about −65 dB is provided at below about 150 kHz and at above about 550 kHz.

The line carrying the output signal from these three stages is taken to ground through a 100 kΩ resistor and then a 390 pF capacitor. A first signal, RFI, is taken from the output signal prior to the output signal passing through the resistor. A second signal, RFQ, is taken from the output signal from between the resistor and the capacitor. The RFI and RFQ signals are then passed onto the main processor IC. The RFI signal is the filtered and amplified RF signal that was received by the telemetry system, while the RFQ signal is a direct current signal having a voltage value equal to the average voltage value of the RFI signal.

The ASIC is also connected in parallel to a crystal oscillator 652 and associated resistor 654 by lines 656 and 658.

The ASIC is additionally connected to a first output port 662 by an I/O bus 664 and a second output port 668 by an I/O bus 672. Each of these two output ports may be formed from an octel tristate non-inverting D flip-flop. These output ports are latching so that inputs from the CPU need not be maintained constantly.

Address decoding and port enablement are provided by a single external port and address decoder chip. This decoder is preferably a 1-of-8 Decoder/Demultiplexer. This address decoder chip is used by both the output ports as well as the keyboard input port 702.

The output ports are enabled/disabled by the RESET signal 726. Such that when RESET is asserted (low) due to the main battery voltage VAA falling below a programmed threshold, the output ports are tri-stated. When this happens, pull-up resistors set the outputs to appropriate states so that all high current devices are shutdown. This is done to preserve the energy stored in the VCC storage capacitors so it is only used for powering the appropriate portions of the circuit for an orderly shut-down.

The ASIC further provides tone driver circuitry 682 to an audio alarm 44 (e.g. a piezo alarm) by lines 686 and 688 that carry first and second buzzer signals that are produced by the Processor IC.

The ASIC further includes a second synchronous serial interface port 692 that functions as an LCD port for communicating with an LCD module 694 that includes LCD driver and display 36 (FIGS. 2 and 3). Three communication lines 696 are used between the serial interface port and the LCD module. One of the lines provides a selectable clock, for driving the LCD, of either about 64 kHz or 32 kHz (i.e. about $2^{16}$ Hz or $2^{15}$ Hz). An additional three control signals 782 are provided by output port 662. These control signals include a chip select signal, a reset signal, and a clock loop back signal.

The LCD of the present embodiment is powered by an LCD driver chip, such as Part No. MC141800A from Motorola. Communication to the LCD module is performed using I$^2$C serial communication protocol. The communication lines are supplied directly from the second serial synchronous interface communication port of the Processor IC.

The external communication device visually communicates to the patient using an LCD display 36. This display includes a dot-matrix graphics LCD for displaying a portion of the information to be conveyed and an icon/fixed segment display for displaying the remaining information to be conveyed. The dot-matrix display allows various languages to be displayed with only a software change or change of a parameter (variable) within the software. In the present embodiment the dot-matrix portion has a display region of about 100×55 pixels.

Figure 5:
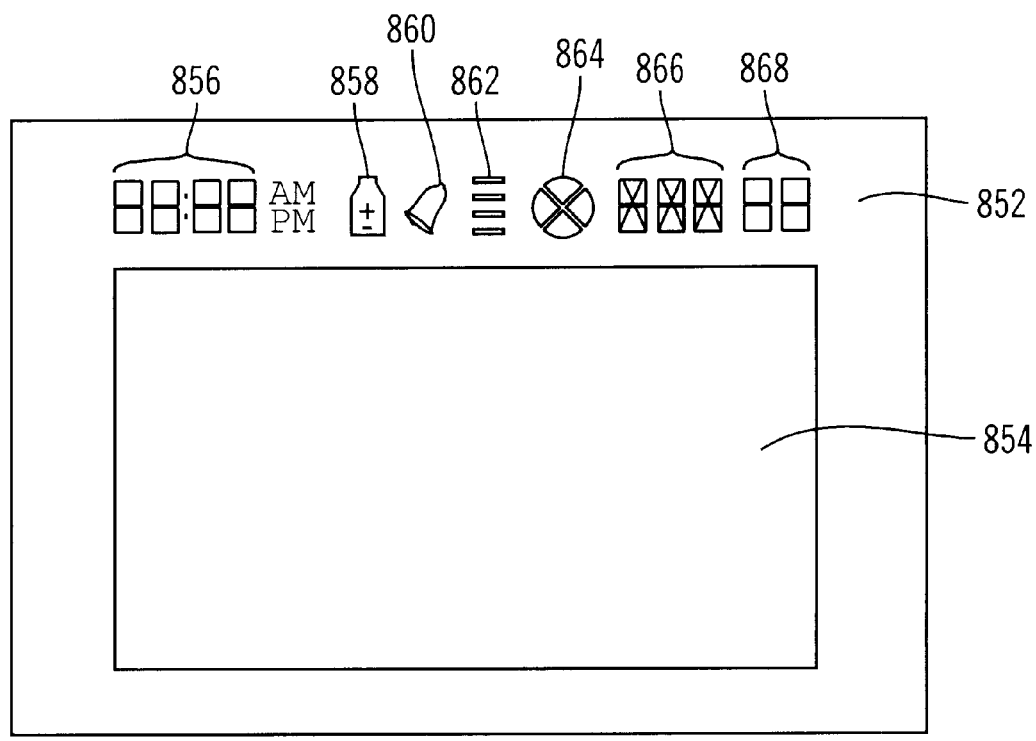
FIG. 5 depicts the display screen of the external communication device of the first preferred embodiment.

FIG. 5 depicts the display 36 of external communication device 32 including the icon/fixed display region 852 and the bitmap display area 854. The icon/fixed element display bar includes a time-of-day indicator 856 which is made up of 4 seven segment display elements, a ":" symbol, an "AM" symbol, and a "PM" symbol. The icon bar also includes a battery symbol 858 that turns on when the main battery of External Communication Device is getting low. The icon display also includes an alarm icon 860 in the shape of a bell that is turned on when an alarm condition is in effect. The icon display further includes a 4 segment reservoir level indicator 862. When the reservoir is estimated to be full all four segments are powered and as the estimated reservoir level drops individual segments are successively turned off. The icon display further includes a circular display 864 comprised of 4 pie shaped wedge elements. The number of pie-shaped wedges being displayed and their motion are indicative of the delivery condition that is currently active. A month indicator 866 is formed from three 16-segment displays while a date display 868 is formed from two additional 7-segment displays.

Turning back to FIGS. 4a and 4b, the ASIC is further connected to an input port 702 by an I/O bus 704. This input port preferably is an octal 3-state non-inverting/buffer/line driver/line receiver. This is a non-latching port. Address decoding and port enablement is provided by a single external port and address decoder chip whose use is shared by output ports 668 and 662.

The keypad 38 is linked to an integrated key interface device 712. The integrated key interface device includes key interfacing, key debouncing, and ESD suppression functions. This device is preferably an octel CMOS switch debouncer with ESD protection for input pins up to 15 kV. The keypad 38 includes four keys with raised buttons and tactile responsiveness and one key without a raised button or tactile responsiveness (i.e. a hidden key).

The integrated key interface device 712 outputs five signals 714 that are provided to input port 702, the key interrupt generator 516, and to a key reset generator 716. Signals 714 include a separate signal for each of the five keys. The signal for each key is low when that key is depressed. The de-bounce duration provided by device 712 is at least 20 ms and is 40 ms typically. The ESD suppression is rated at 15 kV using the human body model.

The key interrupt generator 516 includes an 8 input NAND gate that takes the signal from each of the five keys and performs a NAND operation on them, such that if any one of the keys is depressed (i.e. at least one low input) a high signal will be output by the NAND gate and if no key is depressed (i.e. no low input) a low signal will be output by the NAND gate. The output of the NAND gate is then passed to one input of a two input AND gate along with the reset signal 726 as the other input. As a result if reset signal 726 is high (i.e. not asserted and at least one key is depressed then a high asserted signal is received on line 514 by the first interrupt input 512. If reset signal 726 is low (i.e. asserted) then any keyboard activity is blocked from asserting the interrupt signal.

The key reset generator 716 provides an output signal 718 to an input of the OR logic circuitry 526. The key reset generator 716 receives low signals from the keys that are pressed and high signals from the keys that are not being pressed. A series of OR gates are used to determine if all five keys are depressed (i.e. the four keys with raised buttons and one key without a raised push button). The output of the OR gates is passed through a 100 KΩ resistor and is linked to ground using a 0.1 μF capacitor. This capacitor and resistor are used to suppress short glitches that might be caused by static discharge from the external world via the keypad. Glitches shorter than about 10 milliseconds are suppressed. The output signal is then fed to an inverter and then passed to one input of a two input AND gate. The other input of the AND gate is reset signal 726. The output of the AND gate is the key reset signal 718. Which is passed on to the OR logic circuitry 526.

In addition to the input port 702 receiving key press signals 714 from the integrated keyboard interface 712, it also receives main battery low input signal 724 from power management circuitry 722 and a reset signal 726 from battery fail detector 554. The signal 724 is asserted low and when asserted indicates that the main battery voltage is low. The reset signal 726 is asserted low and when asserted indicates that the main battery is dead. The state of keypad is monitored by input port 702 and the processor is expected to read the input port to determine which key was pressed after receiving a keyboard interrupt.

The main source of power for the external device is a replaceable, AA cell main battery 732 of either the alkaline type or lithium type. A main battery voltage signal 738 (VAA) is supplied to various components and modules as needed. Signal 738 is supplied to an input pin 544 of the analog-to-digital converter that is included in the Processor IC.

The VAA signal 738 is also supplied to a switching type pulse width modulated DC-DC up-converter 734 that produces a boosted voltage signal 736 (VCC) of a definable amount. In the present embodiment the definable amount is 3.45 volts +/−0.1 volt when powering a minimum load of 30 ohms and when supplied with an input voltage of between about 1.1 volts and 1.8 volts. The maximum ripple is 80 mV peak-to-peak. The start-up voltage of the up-converter is no greater than 1.00 V when the starting load is less than 100 ohm at the output. The switching frequency is between 550 kHz and 750 kHz, nominally 600 kHz. However, under light load, the up-converter utilizes burst mode, resulting in a wider noise spectrum. As VCC is generated using high frequency switching, the up-converter is preferably shielded from other components so as to minimize negative effects that might otherwise result, such as, for example, on telemetry reception. In the present embodiment about 440 μF of capacitance is supplied to the VCC lines so as to provide some energy storage for the VCC signal.

The output signal 736 of the converter 734, VCC, is the main operating power for the external communication device though FIGS. 4a and 4b, explicitly depict only two of the modules to which voltage signal 736 (VCC) is routed: (1) the external power on reset generator module 742, and (2) power management module 722.

A backup battery 752 is shown as supplying a voltage signal 754 VCOIN, to power management module 722 and is also passed to analog-to-digital converter input 546 for voltage monitoring. A preferred backup battery is a 3.0 volt lithium battery having a 48 mAHr capacity. As noted above, the power management module outputs a signal 756 that supplies power to the any circuits that are to remain powered by the backup battery when the main battery voltage signal 738, and thus boosted voltage signal 736, falls below a usable level.

In the present embodiment the external SRAM 564 is powered by signal 756. For data retention to occur the voltage supplied must be at least 2.3 volts. In this embodiment signal 756 supplies a voltage of about 2.7 to about 3.6 volts depending on whether or not the power is being supplied by the main battery or backup battery. The maximum operating current for signal 756 is about 1 mA.

Power management in the present embodiment is based on the power management module 722, battery fail detector module 554, and external power on reset generator module 742. These modules are implemented using three primary integrated circuits along with other peripheral elements. The functions of the power management system include providing back-up power for the on-board SRAM, providing proper power-up reset, and providing adequate time for orderly system shut-down when the main battery is dead or removed.

The first chip is a 3 volt adjustable microprocessor supervisory IC which handles the functions performed by the power management module 722. This chip monitors signal 736, VCC, and provides signal 736 as the source for output signal 756 so long as VCC is about 2.7 volts or greater and otherwise provides signal 754, VCOIN, as the source for output signal 756. When VCC rises above, about 2.90 volts, signal 736 is switched back in as the source for output signal 756. The chip also monitors main battery voltage (VAA) and provides low power signal 724 when VAA falls below a desired threshold that is settable by selection of peripheral voltage dividing resistors. In the present embodiment the selected amount is about 1.1 volts. The low power output signal 724 is connected to input port 702 where it can be monitored by the system processor. The low power signal 724 is used by the Processor IC to provide a low battery indication to the patient.

As noted above, the battery management IC also asserts an output signal 762 when the backup battery is switched in as the source of VPOS. This signal is used to gate the chip select of the SRAM chips 564 so that when the back up battery is maintaining the data in the SRAM chips, the SRAM chips cannot be accessed so as to protect the integrity of the data. This asserted state also cuts the backup battery voltage to the processor using a PFET switch that opens line 754 so that it is not connected to A/D input 546. This is done so that the backup battery is protected from a potentially low impedance path to ground (e.g. the A/D input of the ASIC) that may occur when VCC is absent.

When the main battery is dead or removed, all memory access must be completed before the back up battery on signal 762 is asserted. The energy storage capacitance on VCC serves this function by providing time for system shutdown (enough time for completing selected shutdown activities before VCC falls low enough that the back up battery on signal 762 is asserted.

The second chip is a micro-power voltage monitor IC that is used as a programmable voltage detector and handles the functions performed by the battery fail detector module 554. The programmability is determined by the two voltage divider resistors. A hysteresis effect is used to ensure a good pulse and is obtained by use of a 500 kΩ resistor that bridges the input and output lines of the chip. This comparator monitors the voltage signal 738 of the main battery. The output line of the chip provides low reset signal 726. A second output signal for the battery fail detect module is provided by passing signal 726 through an inverter to obtain a high reset signal 556. The threshold is set at about 1.0 V in the present embodiment. The low reset output signal 726 is connected to one of the inputs of input port 702. The high reset signal 556 is used as a power-fail interrupt signal to the processor. This interrupt signal is fed directly to the second external processor interrupt input 552.

When the low reset signal 726 is asserted, the Processor disables the output ports, which in turn shut down all high power devices. This is to ensure that the energy stored in the VCC storage capacitance is used only to support the orderly shutdown activities of the system in the case when the AA battery is dead or removed. During shutdown mode a number of conditions are set: (1) key presses no longer generate key board interrupts to the processor, (2) UART activity no longer generates a UART interrupt to the processor, (3) the output ports, 668 and 662 are tri-stated, (4) the LCD is held in unselected and reset state, (5) the backlight is disabled, (6) the vibrator is disabled, (7) the IrDA module is put in shutdown state, (8) the UART is put in shutdown state, and (9) a 150-ohm dummy load is disabled.

Since the high reset signal 556 is asserted by VAA falling below a threshold value (i.e. failure value for VAA) and since the failure of VM will cause voltage up conversion by module 734 to cease and since all high powered circuits have been shut down and since the back up battery on signal is triggered by VCC failing and since VCC will be maintained for some period of time by storage capacitance, there is a time lag between assertion of the high reset 556 and then assertion of the back up battery on signal 762. In this embodiment, the circuitry and storage capacitance have been configured to provide a lag of at least about 100 ms. This amount of time has been selected as it is sufficient to enable all shut down activities by the processor to be completed prior to assertion of the back up battery on signal 762.

The third chip is an open drain reset IC and handles the functions performed by the external power-on reset generator 742. It monitors the voltage signal 736, VCC. The chip produces an output pulse, or reset pulse, when the VCC voltage level transitions through a programmed threshold voltage level. This reset pulse occurs when transitions are from low to high or from high to low. This reset pulse is routed through an inverter and then to an input of an AND gate.

The input to the inverter is normally retained in a high state by a pull up resistor. However, the input to the inverter is brought low when the low level reset pulse output by the chip occurs. A second input to the AND gate is provided by the low reset signal 726. This is done so as to only pass the pulse on VCC rising but not the pulse on VCC falling. From the AND gate the signal is routed to OR gate 526.

Output port 668 provides UART control signals 758 to the UART circuitry and provides a signal IrDA power down signal 760 to an IrDA module. The UART control signals include a chip selector signal and a shutdown signal. A preferred UART has an SPITM/Microwire™ interface and is capable of supporting RS-232 and IrDA links.

The UART supplies data on line 764 to an inverter 772 and from the inverter 772 to an IrDA transceiver module 780 on line 764'. The IrDA transceiver module then transmits that data through an infrared carrier to a receiver in a second external device (not shown). Data that the IrDA device receives from the second external device through an infrared carrier, is in turn passed to an inverter 774 on line 766' and the inverter then sends the data on line 766 to the UART.

The data transfer rate through this port is fixed at 115.2 Kbit/s. This port complies with the IrDA 1.2 Low Power standard. Whenever external data is received by the IrDA transceiver, a UART interrupt is generated by the UART IC. This interrupt, after passing through an inverter, is fed directly to the third external interrupt input of the processor.

The UART may be placed in a shutdown state to save power. When the UART is in shutdown state, its oscillator is stopped. When the UART is set to be taken out of shutdown state, it takes some time to start up the oscillator, and as such, application software is configured to provide a minimum of 100 ms for the UART to come out of shutdown state before real data is transported using this port.

Output port 662 also provides an enable quiet mode signal 784 to NAND gate 642. The enable quiet mode signal 784 is used for quiet RF mode control. This signal is asserted high and is used when asserted to disable the EL backlight 806 and the vibrator 46. This signal is asserted during RF reception so that noise from these devices will not interfere with RF reception.

The NAND gate 642 takes signals 784 (enable quiet mode) and 634 (RF receive power) and produces an RF quiet signal 786 and provides it as input to AND gates 792 and 794. As the enable quiet signal 784 and RF receive power signals are both asserted high, the output of the NAND gate is low when both are asserted. The low RF quiet signal 786 disables the high noise devices stated above. It is also connected to VCC using a 150 ohm dummy load. The purpose of this load is to force the up-converter to operate at the 600 kHz nominal switching frequency, instead of any other frequency or burst mode. This helps in reducing noise during RF reception.

Output port 662 provides an output signal (not shown) to a 150 ohm dummy load that may be used to place a load on the AA battery during battery voltage measurement. This load is turned on by providing a high signal to it from the processor IC.

Output port 662 provides an enable LED signal 788 to AND gate 794. The enable signal 788 is the backlight "on" signal and is asserted high. When asserted, this signal causes the backlight to be turned on unless the RF quiet signal is being asserted (i.e. low). AND gate 794 supplies its output 802 as an input to a backlight driver 804 which in turn powers an Electroluminescent (EL) backlight 806 which lights up the LCD device. A high RF quiet signal 786 enables the selection of the backlight while a low RF quiet signal disables the selection of the backlight, while the enable LED signal turns on and off the backlight when enabled. The backlight is controlled in this way because it is high current/high noise device, and it is desirable to disable it during RF reception. When the system is not in an RF reception state, the backlight is enabled regardless of the setting of enable quiet signal 784 because RF receive power signal 634 is low.

The Electroluminescent (EL) backlight panel is used to illuminate the LCD in low light level conditions with a green light having about 0.15 ft Lm brightness at 0.75 inches from the output of the LCD display. The EL panel is driven by a DC-AC converter IC that boosts the voltage level. The DC-AC converter with the aid of an inductor to help generate the boosted voltage level and a capacitor for setting the oscillator frequency boosts the voltage from VCC to a signal of about 140 VAC peak-to-peak at about 300 Hz.

Output port 662 provides and an enable vibrator signal 790 to AND gate 792. The enable vibrator signal 790 is asserted high. When asserted this signal turns the vibrator on unless the RF quiet signal 786 is being asserted (i.e. low). AND gate 792 provides its output 812 as an input to the vibrator device 46. The RF quiet signal 786 enables (logic high) and disables (logic low) the selection of the vibrator, while the enable vibrator signal 790 turns on and off the vibrator when enabled. The vibrator is controlled in this way because it is a high current/high noise device, and it is desirable to disable it during RF reception. When the system is not in RF reception state, the vibrator is enabled regardless of the setting of the enable quiet signal 784 because the RF receive power signal 634 is low.

The vibrator 46 is a DC vibration motor which is used as a secondary alarm device. The preferred motor draws a current of about 60 mA and has a nominal rpm of about 8100. The signal from AND gate 792 is used to control an N-MOSFET transistor switch to supply the VCC signal to the motor.

As discussed above, a single processor IC is used in the external communication device while two processor ICs are used in the Implantable Device. In this first preferred embodiment all three of these processors are identical.

As it is preferred that the implantable device have a long implanted life, and as the implantable device of the present embodiment does not use rechargeable batteries, a low-power constraint is imposed on the processor IC. This low power constraint is three fold: (1) use of low power circuit elements and design, (2) use of electronic modules that are capable of being put into low-power consuming states or non-power consuming states when not needed to perform specific functions, and (3) use of control hardware or software to put the modules in their reduced power states and to pull them out of those states. The result is that the processor IC is designed and controlled to operate at an average power of less than about 30 $\mu$W. At a supply voltage of 2.9 Volts, this power consumption turns into an average current of less than about 11 $\mu$A. The entire implanted electronic system preferably draws an average of less than about 32 $\mu$A. In this embodiment, the processor IC operates with a voltage of between about 2.3 V and 3.6 V. To achieve desired overall power consumption for the implantable device, the processor IC is a custom designed CMOS device using 0.8 micron technology with the physical construction of cell design utilizing small gates, drains, and diffusion regions.

The core processor 912 design preferred in the present embodiment is a CMOS low power version of the INTEL 8086 processor with a minimized number of logic gates and enhanced timing so as to consume less power. The Core Processor includes ten additional instructions so that it is software compatible with the 80186 processor. It is a multiplexed bus device having the 16 low order address bits, out of a total of 20 address bits, multiplexed with the 16 data lines. De-multiplexing is achieved with on-chip latches so that the low order 16 address lines are available as outputs to the device. The four high order address lines and the bus high enable signal are not multiplexed. As noted above, the processor IC also integrates a number of modules and functions so as to reduce the power consumption as compared to using discrete components for achieving the same functionality.

A SEEPROM interface 914 is provided within the processor IC for exchanging information with an off chip SEEPROM device. A two line interface is used to exchange data with the SEEPROM device and a power line is also supplied from the processor IC to the SEEPROM so that it may be selectively powered so as to reduce power consumption when access to the SEEPROM is not needed. In the present embodiment, the SEEPROM associated with each of the two processor ICs in the implantable device has a capacity of 32 kbytes while the two SEEPROMs used in the external communication device have a capacity of 64 kbytes each. In the present embodiment, the SEEPROM provides periodic acknowledgments when the SEEPROM is interacted with. A SEEPROM control register and a SEEPROM data register are also provided. These two registers provide a bit that supplies power to the SEEPROM, a bit that provides an oscillating signal to the SEEPROM, a bit that provides data to be written to the SEEPROM, and a bit that can be read to pickup data that is being supplied by the SEEPROM.

The Boot ROM 916 is an on-chip read only memory that provides the initial boot code for the CPU. The Boot ROM is 1 kbyte metal mask programmable ROM.

The address location of the beginning of the boot ROM 916 is is consistent with the Intel 8086 specification for reset vectors. When reset occurs, the processor begins execution of the code found in ROM which is a program that loads further code from the SEEPROM located off-chip. Further details on execution of the ROM code may be found in the previously referenced U.S. patent application corresponding to Docket No. USP-1075-A.

A 16 kbyte section of static RAM (SRAM) 918 is provided within the ASIC. This space is used for stack, general variables, and core program space such that most of the operational implantable device code and external communication device code reside in this space.

The processor IC includes a memory decoder module 920 that is capable of decoding the 16 kbytes of internal SRAM and is also directly capable of decoding 512 Kbytes of external memory. The memory decoder contains Boolean logic gates to decode the 8086 address space for each individual bus transaction. The amount of externally addressable SRAM may be increased by adding one or more additional bank select triggers such as by using the a processor IC output that is not being used for some other function. For example, in the external device the output signal that is used to fire the pump mechanism may instead be used as a bank select signal as it is otherwise not being used. This provides the ability for the external communication device to be able to decode 1 Mbyte, or more, of external SRAM. The memory decoder is further capable of decoding the 1 Kbyte of internal ROM.

A low power crystal oscillator module 922 internal to the Processor IC is used in conjunction with the an external oscillator crystal and a shunting resistance to provide a stable 1.049100 MHz +/−500 Hz clock source while drawing less than about 2 μA from a 2.2 V to 3.5 V supply. The circuit is intended to operate with a minimum frequency of 1.048576 MHz crystal using a shunt resistance of about 20 MΩ in the implantable device and about 2 MΩ in the external communication device. The shunt capacitance of the crystal is preferably no greater than 1.5 pF. An external shunt resistor is provided in parallel to the clock crystal across two external connectors of the ASIC to provide DC feedback to the circuit. The amount of resistance is selected as a balance between oscillation start up and current consumption.

The timer module 924 is composed of the system clock generator and circuits responsible for generating various timing signals. The processor IC uses the (1.048576 MHz+ 500 Hz) external crystal to generate the system clocks. Tolerance of the crystal oscillator is be better than +/−500 parts per million (ppm) including the drift due to aging, and temperature induced variances within a range of −10° to 50° C.

The Timer Module 924 consists of a (A) system clock generator; (B) a CPU clock module; (C) a pulse stealer; (D) a clock enable register; (E) four independent timers (wake up 1, wake up 2, sleep, and one minute), and (f) a time-of-day timer that can be made to register time in subsecond intervals.

The system clock generator module, is a 20 bit ripple counter that has the ability to load a pattern into its lower 14 bits. This counter is used to provide the system clocks necessary for operation of all other modules. In the present embodiment a pulse stealing technique is used to fine tune the oscillation frequency for all clock signals generated by this module that have a frequency of about 8192 Hz or less.

The clock frequency of the CPU (i.e. the frequency of the CPU clock) may be selected and the CPU clock made to stop by writing appropriate values to appropriate CPU clock registers. The frequency select circuit consists of two registers and a synchronizing circuit. The synchronizing circuit is used to ensure that narrow clock signals (i.e. glitches) are avoided when the frequency of the CPU Clock is changed.

A pulse stealer circuit is provided for precise system timing of selected clock signals. In the present embodiment the pulse stealer function is applied to the clock signal that has a frequency that is just slightly more than 8192 Hz target frequency as provided by the system clock generator. The pulse stealer circuit gives the ability to periodically steal pulses from a selected clock signal to produce a clock signal of lower and more desirable average frequency. In the present embodiment the pulse stolen signal, is used to create all system clocks that of lower frequency. In implementing pulse stealing for the present embodiment, the CPU loads a 16 bit value into two eight bit configuration registers. The timer whose signal is to be modified is used to cause a counter to count up from zero to the value loaded into the registers at each time a comparator recognizes a match. After the counter reaches the value specified in the registers, a single pulse is removed from the output signal (stolen from the output signal) to provide the modified output signal. Then the counting begins again from zero and the process is repeated over and over so that a modified output signal, or pulse train, having a desired average frequency is generated.

A clock enable control register is provided so as to allow the CPU to selectively enable or disable the clock signals used by other modules. In the present embodiment these other modules include the first and second synchronous serial ports, the analog-to-digital converter, and the insulin pump charging circuitry. Enablement/disablement for a given module is "bit mapped" to the control register so that the control register may be used to "gate" these clocks on or off.

Four system timers are provided. These timers provide interrupts to the CPU at selected intervals. The internal logic of the first three of these timers is identical with the exception of the input clock frequency and the number of bits to count to before causing an interrupt. The interrupt interval for each timer is programmable by the CPU by writing an appropriate value to an appropriately sized control register associated with each timer. Once an interrupt interval is written into the timer by the CPU, interrupts will be continuously generated by the timer without further intervention of the CPU. The timers continue to "run" independent of when or if the CPU services the interrupts that they create. Thus, interrupts will continue to be "issued" at the same programmed interval, and will stay asserted if not serviced. The act of servicing the interrupt clears the interrupt condition. The CPU clears any pending interrupts by writing to the associated control register.

The first of these timers is the first wake-up timer and it generates a first wakeup signal that based on a 1 Hz input clock frequency and a programmed count value that is to be reached before generating its interrupt signal. Examples of the use of this timer in the present embodiment include Watchdog monitoring and nominal RF reception and transmission start times.

The second of these timers is the second wake-up timer and operates off an 8 Hz input clock frequency and is also programmable to count to a specified value before generating its interrupt signal. Examples of the use of this timer in the present embodiment include various uses within the external communication device, including spinning the pumping status indicator on the display panel, IrDA timing for missing bytes and closing the channel, beeping, and keyboard blink timing.

The third timer is the sleep timer which operates off a 1,024 Hz input clock frequency and is programmable to count to a specified value before generating its interrupt signal. An example of the use of this timer in the present embodiment includes pump stroke charging and recharging.

The fourth timer is a one minute wake up timer and provides an interrupt every 60 seconds based on a 1 Hz input clock frequency. This counter provides two functions: (1) it provides the seconds portion for the time of day, and (2) it interrupts the CPU every 60 seconds. The principal purpose for the CPU writing into this timer is to adjust the software perception of the second number within a minute. The register for this timer does not hold the number to be counted to but instead holds the present count of the counter that continues to increment each second until a count of 60 is reached and then it starts over. Examples of the use of this timer in the present embodiment include counting elapsed minutes, performance of delivery calculations for pump strokes, determination of the present half hour, and one minute RF listening by the external communication device.

In the present embodiment one register bit is controllable to indicate whether RF reception is given priority over the charging of the pump circuit for noise considerations even though there may be some negative impact on power drain resulting from a need to partially recharge the pumping circuitry after a telemetry interruption. Toward this end, the pump clock itself is disabled whenever an RF receive power signal is asserted and the priority bit is set to give priority to RF reception. On the other hand, when this bit is oppositely set, by software, then the pump clock is allowed to remain on regardless of telemetry activity. As both telemetry operations and pumping operations are current intensive, it may be desirable to avoid both systems operating simultaneous so as to reduce maximum current drain on the battery at any given instant in time.

A watchdog monitor circuit 928 is provided to ensure that detection and system reset will occur if the CPU ceases to properly execute instructions. To achieve this, the watchdog monitor is configured to assert a system reset signal if an interrupt signal from the first wake-up timer occurs twice without the CPU properly servicing the watchdog monitor. In the present embodiment, the CPU resets the watchdog monitor by two writes into the watchdog monitor. Data for the first write has first pattern and data for the second write has a second pattern that is different from the first pattern. To ensure that the system is operating properly at both the interrupt level and the mainline code level, one of the two values is written by an interrupt routine while the other is written by the mainline code. Writes of values other than the first pattern followed by the second pattern will reset the sequence that the Watchdog is expecting. The reset signal generated by the watchdog is brought out of the ASIC and back to the external reset input of the ASIC.

Following a system reset or power-on reset, the watchdog monitor is not active. This allows the CPU time to perform initial configuration and housekeeping. The watchdog is activated, or enabled, as soon as the CPU writes any data pattern to a watchdog monitor register. Once enabled, the watchdog cannot be disabled until another CPU reset occurs. The ROM boot code activates the watchdog early on in its execution but sets the first wake up interval to a time sufficient for system configuration to occur. When the watchdog causes a reset, a piezo signal is put out so that an audio alarm will sound. This piezo signal remains on until the CPU re-activates the Watchdog.

The RF Module 930 in the processor IC consists of an (A.) RF timer circuit, (B.) a digital RF transmitter section that includes a QFAST® RF modulation transmitter, (C.) an analog receive module, (D.) a digital receive section that includes a QFAST® RF modulation receiver, and (E) a time synchronization section.

The RF timer circuit provides clock signals used by the other portions of the telemetry circuitry to provide a carrier signal for transmission, provide a signal for modulating the carrier, provide signals for demodulating received signals, and the like. The primary signal timer signal is pulled from the system clock generator module. The generation and shut of the primary RF timer signal is controllable by hardware or software based on values that are written into various registers which enable signal generation when needed and power savings when not needed. The time synchronization module ensures that the concept of time as held by the communication device and as held by the medical device are sufficiently close so as to enable RF communication to occur while maintaining transmission time and listening time of the RF hardware to a minimum. Further details on RF timing synchronization, autonomous and software activation and deactivation of telemetry hardware components are provided in the above referenced US patent application corresponding to Docket No. USP-1077-A.

The telemetry system provides a half-duplex link between the implantable device and the external communication device using a carrier frequency of about 250 kHz and a data signal having a frequency of about 8 kHz. The transmitter hardware uses the 8 kHz data signal to modulate the carrier signal to generate signals that will be transmitted by the antenna. The receive hardware receives the modulated signal and demodulates it to extract the 8 kHz data signal. Both the implantable device and the external communication device have transmit and receive capabilities to allow two-way communication.

Most of the RF telemetry circuits necessary for communication between the external communication device and the implantable device are implemented in the processor IC. In order to minimize the digital noise interference that the processor IC might impart to the weak RF signals that are being received, a high-gain RF amplifier is implemented off-chip. Also as discussed above, an RF antenna, that is used for both transmission and reception, and circuitry to select between reception and transmission are implemented off chip. The remaining analog sections and all the digital demodulation circuits are implemented in the processor IC.

The RF module of the Processor IC outputs transmission signals for transmission by the external antenna. It also provides a power signal to the external amplifier and an RF receive power control signal that is used to switch between a transmission configuration and a reception configuration. Both these signals are controllable by bit values placed into registers so that power consumption may be minimized when component operation is not required. The RF module also receives input signals from the external receiver hardware.

A Quadrature Fast Acquisition Spread Spectrum Technique (QFAST®) is used as the modulation technique. QFAST® modulation is based on an Offset Quadrature Phase Shift Keying (QPSK) modulation technique. In this technique, data generated by the CPU modulates clock signals at the carrier frequency. As a result of quadrature modulation, in-phase and quadrature-phase components of the given data stream are generated. These two components are then applied to opposite ends of the external antenna so that a combined signal is transmitted.

In QFAST®, data rate adaptability is accomplished through a spread-spectrum "coding gain" concept, with the spreading code being a simple clock. The modulation produced by the QFAST® modulator can be demodulated in a manner which delivers both clock and data. All of the QFAST® modulation and demodulation circuits are digital and are incorporated into the processor IC.

The QFAST® technique provides a communication system with the following attributes: (1) it extracts the clock from the received signal without a clock recovery loop; (2) it provides demodulation of data without phase ambiguity and without the requirement for synchronous demodulation; (3) it makes effective use of the available transmission bandwidth, (4) it results in fast acquisition of the message signal; (5) it is relatively immune to the effects of highly dispersive and distorting propagation media; (6) it does not require regeneration of a phase-coherent local replica at the receiver of the transmitted carrier; (7) it does not require resolution of ambiguity between the in-phase and quadrature-phase channels in the receiver; and (8) it does not exhibit data phase ambiguity.

The transmitter section of the telemetry system receives byte wide parallel data packets from the CPU and then loads the data into a parallel-to-serial shift register. The serial data is then sent to the QFAST® RF modulation transmitter section to modulate two quadrature clock signal components each operating with a carrier frequency of about $2^{18}$ Hz) and shifted in phase relative to each other by 90 degrees. The two components are then delivered to opposite ends of the antenna. As long as there is data in the transmitter parallel-to-serial shift register, the RF transmitter remains activated. If the transmitter doesn't have data available when the next byte is to be transmitted the message is considered to have been completely transmitted and the CPU shuts off the transmitter circuitry so as to minimize continued power drain.

External to the processor IC, the received RF signal is amplified by a high gain receive amplifier. A bandpass filter is used to attenuate out-of-band components such as those due to AM radio stations. The amplified RF signal then enters a mixer in the RF module of the processor IC and is converted to baseband using a two mixers, one in-phase mixer and one quadrature mixer both at the carrier frequency. The mixer outputs are the quadrature components of the baseband signals. An integrator & dump function in the RF module then removes the sum frequency (2fc) and high frequency noise (i.e. acting as a low pass filter) from each of the two signal components. The processed signals are then digitized using a comparator and passed to the demodulator where the data and clock are recovered.

Further detail about QFAST® (Quadrature Fast Acquisition Spread Spectrum Technique) may be found in U.S. Pat. No. 5,559,828, entitled Transmitted Reference Spread Spectrum Communication Using a Single Carrier with Two Mutually Orthogonal Modulated Basis Vectors, by Armstrong, et al.

The ASIC also includes an interrupt handler 932. There are nine interrupt sources. All interrupts except one are maskable. The only non-maskable interrupt is generated by the memory decoder as a result of an invalid address detection. The interrupt handler module consists of a capture module for capturing interrupt conditions, a handling module, and a priority encoder module. Three of the nine interrupts may be used for external as well as internal interrupt sources, as for example by the external communication device.

The capture module is used to capture the occurrence of an interruptible event. This module contains two sets of registers: an enable control register (under CPU control), and (2) the capture register. The enable control register is bit mapped to each of the possible interrupt inputs. If the bit corresponding to an interrupt in this register is high the interrupt is enabled and can cause the interrupt signal to the CPU to be asserted. When enabled, an interrupt condition signal sets a bit in the capture register and a corresponding interrupt signal is asserted. The bits in the Capture Register are de-asserted only by a system reset or individually when a corresponding signal is asserted. The interrupt signals are passed to the interrupt processor module and combined with respect to priority to provide a single interrupt to the 8086 CPU delivered on the CPU's interrupt input line.

The handling module provides the necessary logic to accommodate the 8086 double interrupt acknowledge cycle as well as daisy chaining the interrupt signals to provide a priority for the highest level of interrupt in cases where multiple interrupts are pending simultaneously. When multiple interrupts are pending, the highest is serviced first. This is accomplished by asserting the output signal corresponding to the highest pending interrupt during the second CPU interrupt acknowledge cycle. This signal serves two purposes. First it is fed back to the capture module to clear the pending interrupt and second it is sent to the priority encoder module for encoding the interrupt vector.

Only one of the inputs to the priority encoder module is asserted at a time. This module encodes the interrupt level number of the asserted input and generates the appropriate interrupt vector value.

An analog-to-digital converter 934 (A/D) and associated signal multiplexer system are provided to sample analog signals. The analog signals for the implantable device include (1) battery voltage, and (2) the charge pump voltage. The analog multiplexer is used to select the analog input signal that is to be provided to the A/D. An amplifier is used following the MUX to provide signal conditioning for the input signals. Bits are provided in a control register for selecting the MUX channels, for enabling the MUX, for enabling the amplifier, enabling the analog to digital converter, providing a conversion status indication, providing a begin conversion signal, and for supplying a clock signal to the A/D converter.

The LCD Clock Driver consists of two input clocks (e.g. about 64 kHz (e.g. $2^{16}$ Hz) and about 32 kHz (e.g. $2^{15}$ Hz)), a MUX to select between them and a bit and an AND gate to gate the clock on and off.

The Processor IC has an alarm driver and interface 938 that offers direct control of a piezo buzzer alarm. The processor IC drives the alarm through a 2-wire interface. Software may be used to select one out of 128 frequencies ranging from about 64 Hz to about 8192 Hz. The tone duration and volume are also under software control. In the dual-processor implantable device, the monitor processor controls the buzzer. The piezo buzzer logic consists of a register, a counter, and compare functionality to provide a variable frequency to the piezo buzzer. The value in the register is compared to the value in the counter. Each time the values are equal the driving signal toggles to the next programmed signal. Additional logic circuitry is provided to allow volume control for the piezo buzzer. The outputs of each line are used externally as differential signals to the piezo buzzer. Thus with this scheme, the piezo can sound different frequencies and the volume of the piezo buzzer can be controlled.

After a processor IC reset, the piezo is driven at about 1024 Hz. This signal is gated with the output of a register bit that is under control of the CPU. The piezo signal is inhibited by this gate when the CPU writes into the watchdog enable register.

The Processor IC has two Synchronous Serial Interface (SSI) ports 944 and 942. Each interface provides full duplex serial communication ports that operate at about 500 kHz. One of these ports is used for inter-processor communication in the dual processor implantable device. In the external communication device, one port is used for IR based serial communications and the other is used as an interface for the LCD display panel. Each interface port supplies both data and clock. The clock driving the SSI may be enabled or disabled, thus controlling power consumption when the SSI is not needed. A control register is used to turn ON/OFF the SSI.

The RF communication between the implantable device and the external communication device occurs in the form of messages (sometimes referred to as communication signals or packets) that are passed back and forth between the two devices. In this embodiment these messages have a multi-part format or protocol: (1) preamble, (2) frame sync, (3) telemetry identifier, and (4) data.

For communications from the implantable device to the external communication device the preamble is a repeating pattern of "10", i.e. 10101010. This alternating pattern of ones and zeros is broadcast for 8-bit times. This pattern is considered the standard preamble pattern.

For communications from the external communication device to the implantable device, the preamble is either of the standard preamble pattern but applied for an extended number of bit times (e.g. 24, 48, or 96) or is of an attention preamble pattern that is applied for, typically, even a longer extended number of bit times. The attention preamble pattern is formed of a repeated pattern of "110110 . . . 110". In other embodiments, other attention preamble patterns may be used (e.g. repetitions of "011", "100", "001, "1011", and the like).

The preamble, whether of the standard pattern or the attention pattern, is used so that the RF reception hardware can establish bit synchronization (i.e. bit boundary recognition) of the incoming data. However, the attention preamble is further used to get and hold the receiver's attention for a defined period of time. As long as the attention preamble is being received, the receiver's hardware will stay on and continue tracking the signal in anticipation of an incoming message.

The attention preamble is considered to be lost, or no longer being received, when the receiver receives more than 2 inappropriate bit values during receipt of any 64-bits or when the frame sync pattern is received.

The attention preamble may be used when there is some uncertainty in the time synchronization of the two devices. The extra length of the attention preamble allows the receiver's reception window to open a little latter than anticipated and to still have the receiver pick up the entire message. The extra length of the attention preamble allows the receiver's reception window to open earlier than anticipated, so long as a minimum number of bits are heard by the receiver during the time its reception window is normally open, and still have the receiver's attention locked onto the preamble and have the receiver remain on as long as the attention preamble is being received, plus a little more, in anticipation of receiving a frame sync pattern.

In the present embodiment, frame sync may actually be considered byte sync (i.e. frames are bytes) and is a single byte of a selected pattern and is used so the receiver can obtain byte boundaries for the transmitted data. In the present embodiment, the selected pattern is "10110000.

This comparison process continues so long as the receiver continues to listen for an incoming message or until a valid frame sync pattern has been received. If the receiver is continuing to listen beyond its normal reception window (i.e. listening period), due to the reception of an attention preamble, the listening will not stop immediately upon the attention preamble being lost. The comparison process for ascertaining the receipt of frame sync continues for a number of bits after attention preamble is lost, even if the listening period has ended, as its loss may be associated with the partial receipt of frame sync. Once frame sync is received a valid frame sync signal is asserted.

In the present embodiment, the telemetry identifier (i.e. telemetry ID) is a 3-byte value that is used to ensure that only the intended receiver receives a message. The value of all "1s" indicates a universal message that is to be received by all receivers, otherwise the telemetry ID must be agreed upon between the receiver and transmitter. A unique ID is provided for each implantable device and each external communication device during manufacturing. Only the external communication device can transmit a message using the universal ID code. The telemetry IDs that the receiver will consider to be valid are the ID of the receiver or the universal ID. All other incoming bit patterns will be rejected with the result that the receiver will be either turned off or will start again looking for a valid frame sync pattern attention preamble.

If a valid telemetry ID is received, the receiver listens to the remaining portion of the message.

In the present embodiment, data is provided in an integer number of bytes following the telemetry ID. In the present embodiment the first byte of the data indicates the message type. The first seven bits of the first byte is an operation code or op-code while the eighth bit is either ignored or is set and interpreted as a sequence number (to be discussed hereafter) dependent on whether or not the first seven bits call for a sequence number or not. Each op-code, based on its nature, is followed by data in a defined number of bytes. The specific op-code itself may dictate the number of bytes that follow or alternatively the specific op-code may dictate that the number of bytes to follow may be extracted from the first byte or several bytes of information that follow it. In alternative embodiments, op-codes may have a different length, or not be used at all, the message length or message end may be dictated in other ways. Based on the op-code and potentially one or more bytes following it, the receiver knows exactly how many more bytes of data to listen for. After receiving those bytes, the receiver may be turned off to conserve power.

For some messages dealing with drug delivery, the data portion of the message may include a bolus number. The bolus number is similar to the sequence number in that it is incremented by both the implantable device and external communication device under controlled conditions so as to reduce the possibility of bolus requests being delivered more than once when duplicate requests may be made as a result of the external communication device failing to receive a confirmation that a previous request was received. The bolus number may be a single bit number in some embodiments but in more preferred embodiments it is a multibit number (e.g. 2-bit, 4-bit, 7-bit, 1-byte, or 2-bytes) so that it can take on more than two values thereby making it less likely that an error will escape detection due to received and expected numbers erroneously matching. The incrementing of the bolus number may occur within the external communication device when it receives confirmation that a message was correctly received and it may be incremented by the implantable device when it correctly receives a bolus request. As such when a duplicate request for a bolus is received by the implantable device it can recognize that the expected and received bolus numbers do not match and that requested bolus is not a new request. As such the implantable device can respond to the repeated request that the bolus was correctly received and delivered (with out performing a second delivery and without incrementing its expectation of what the next bolus number will be).

In the present embodiment, the data portion of the message ends with a one or 2-byte validation or error checking code (its type is dictated by the op-code included with the message). The preferred error checking code of this embodiment is in the form of a cyclic redundancy code (CRC).

In the present embodiment, the telemetry system may loose bit synchronization if insufficient bit transitions are received per unit time (e.g. if more than about 100 to 120-bit times lapse without receiving a transition. In order to ensure that a sufficient number of bit transitions occur, the data portion of the message, with the exception of the op-code is randomized prior to transmission and is de-randomized upon receipt.

In order to keep power requirements low in a preferred implementation, the external communication device and implantable device attempt to maintain a common time base, transmissions are set to start at specified times, and reception windows are set for specified times and lengths. In this way, the receiver may remain in a powered down mode most of the time and can turn on to listen for a potential incoming message at the specified times for the specified lengths of time. If a message is found to be incoming, the receiver stays on, otherwise it goes back to sleep (i.e. power down mode).

In the present embodiment time synchronization for telemetry communication is maintained using two techniques. The first technique periodically determines the present difference in the concept of time (e.g. second boundaries) as held by the communication device and medical device and the difference is used to reestablish synchronization of the timers. In the present embodiment, reestablishment occurs on the part of the communication device each time it receives a valid communication from the medical device.

The second technique determines a rate of drift that has occurred between the concept of time held by the communication device and that of the medical device. The determined rate of drift is used in combination with a determined lapse in time to estimate how much drift has occurred. This amount of drift is then used in shifting a listening start time or transmission start time of a first one of the devices to match what is believed to be the potential transmission period or listening period of a second one of the devices.

In the present embodiment, software may be downloaded from the external communication device to the implantable device. The downloading of software may include the downloading of executable software as well as the downloading of data structures that may be used by the executable software.

In the present embodiment, a specific external communication device is configured/programmed to communicate substantively with only one specific implantable device, that is in turn configured/programmed to communicate substantively with only the same specific external communication device. An external communication device is capable of retaining the telemetry ID of exactly one implantable device at a time and an implantable device is capable of retaining the telemetry ID of exactly one external communication device at a time. A small amount of non-substantive communication (i.e. communication that does not impact insulin delivery) can occur between external communication devices and implantable devices that are not linked (i.e. partnered or married) to one another (i.e. provided with each others telemetry IDs).

In the present embodiment, many different types of messages and responses thereto can be written into the programs that control the implantable device and the external communication device according to the guidelines set forth above. These messages may be used for a number of different purposes. For example, (1) they may be system level messages that are used for testing devices, for resetting devices, or for establishing relationships between implantable devices and external communication devices, (2) they may be alarm messages that are used to convey alarm conditions or to clear alarm conditions, (3) they may be miscellaneous messages that set various parameters or perform various read operations, (4) they may be delivery messages that set delivery amounts, read delivery status, or set parameters such as concentration and pump stroke volume that may be required to appropriately control delivery of the drug, (5) they may be data log messages that set data log boundaries, read boundaries, or clear data logs, boundaries or read information from various data logs or supply information to those data logs, (5) they may be refill messages that are related to amounts of material that are added to the reservoir periodically, (7) they may be compound messages that perform more than one function, or (8) they may be error messages that request error condition status or supply error condition status.

Additional preferred features and aspects of a telemetry system are provided in previously the referenced US patent applications that correspond to Docket Nos. USP-1076-A, USP-1077-A, and USP-1079-A.

The External Communication Device (CD or ECD) is a hand-held device that is used to program and communicate with an Implantable Device (ID). The External Communication Device, of the present embodiment, includes the hardware features discussed herein above. The CD hardware and CD software work together to provide the desired functionality for the system.

The hardware includes a display with an icon region and a dot matrix region, a backlight for the display, a five-button keypad (one button is hidden), an alarm, a vibrator, and an IR device for serial communications with a second external device. The CD software is menu-driven. The device operates from a replaceable 1.5 Volt AA battery. There is a backup battery that retains memory while the replaceable battery is removed.

The dot matrix region is used to display the majority of the information that is provided to the user. This region, however, consumes more battery power than the icon region, as such when the external communication device is idle, the dot-matrix region is powered down to conserve energy. If the dot-matrix region is powered down, it is powered back on once a key is pressed.

Figure 7A:
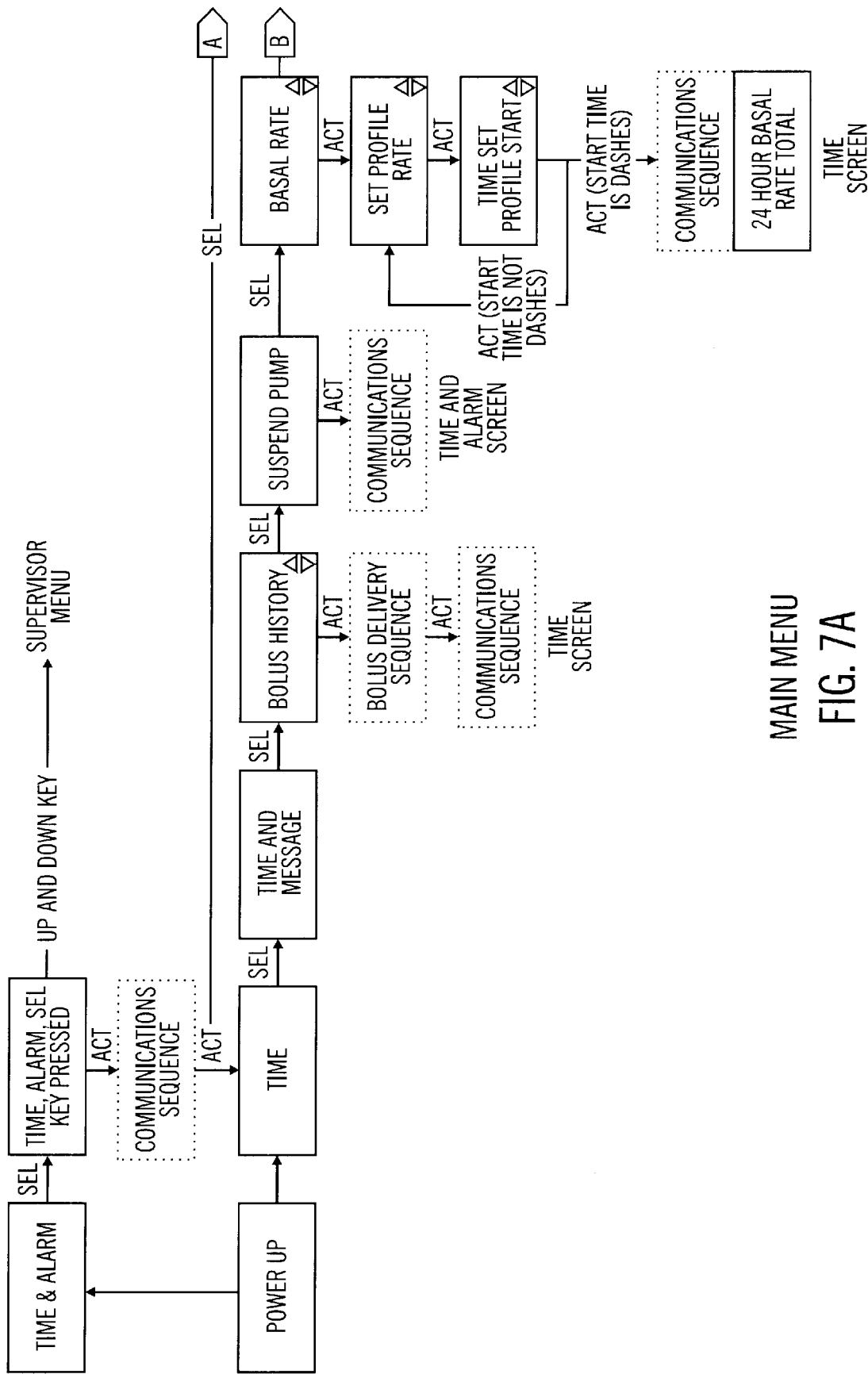
FIGS. 7a and 7b depicts the main menu structure for the user interface of the external communication device of the first preferred embodiment.
Figure 7B:
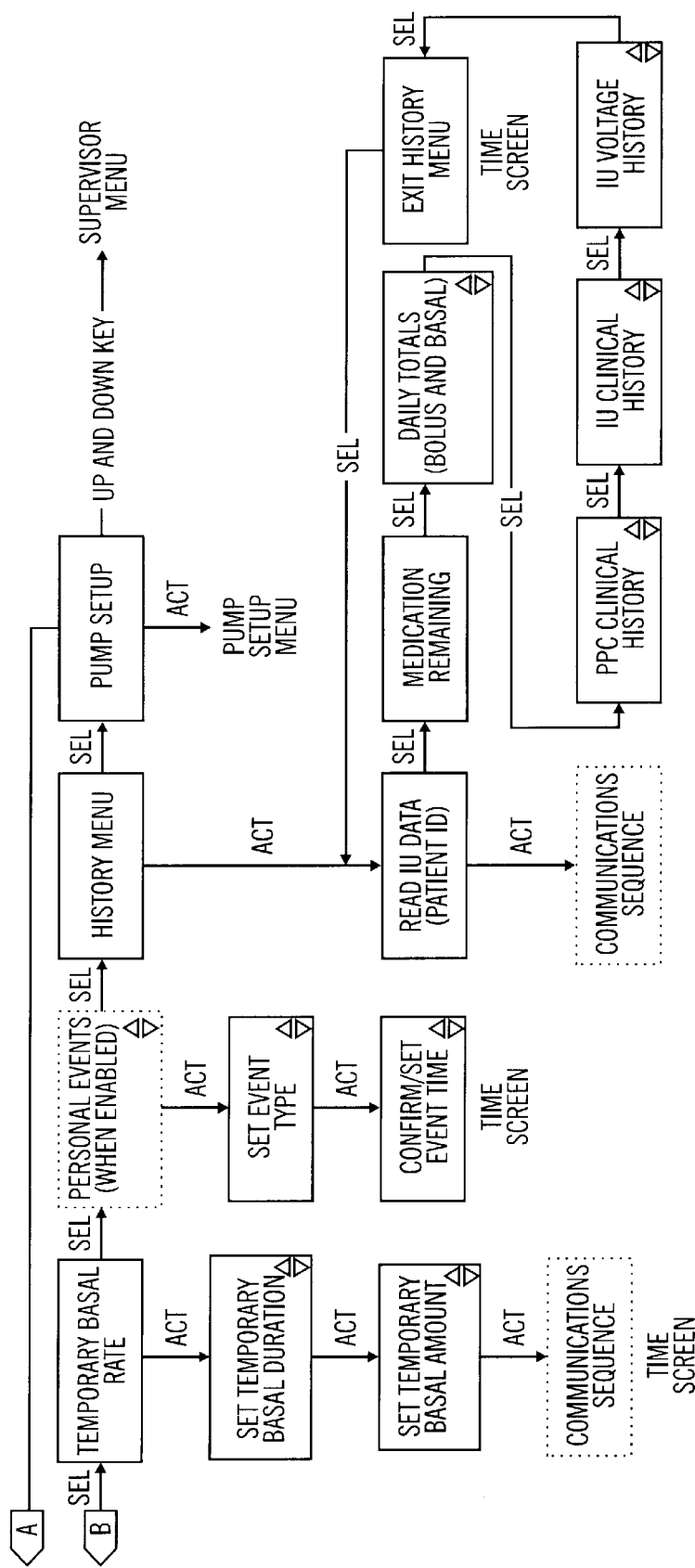
Figure 8A:
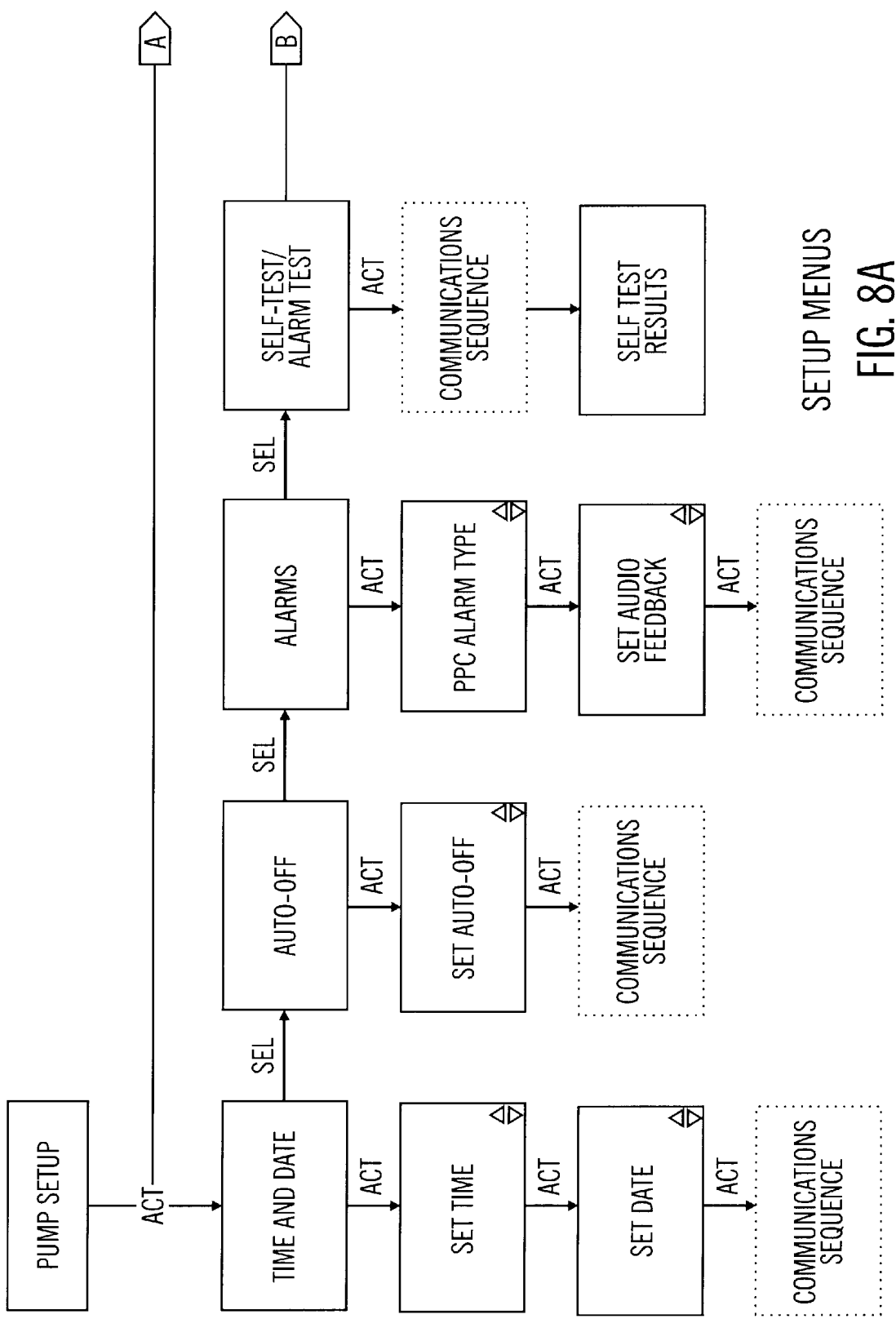
FIGS. 8a and 8b depicts the setup menu structure for the user interface of the external communication device of the first preferred embodiment.
Figure 8B:
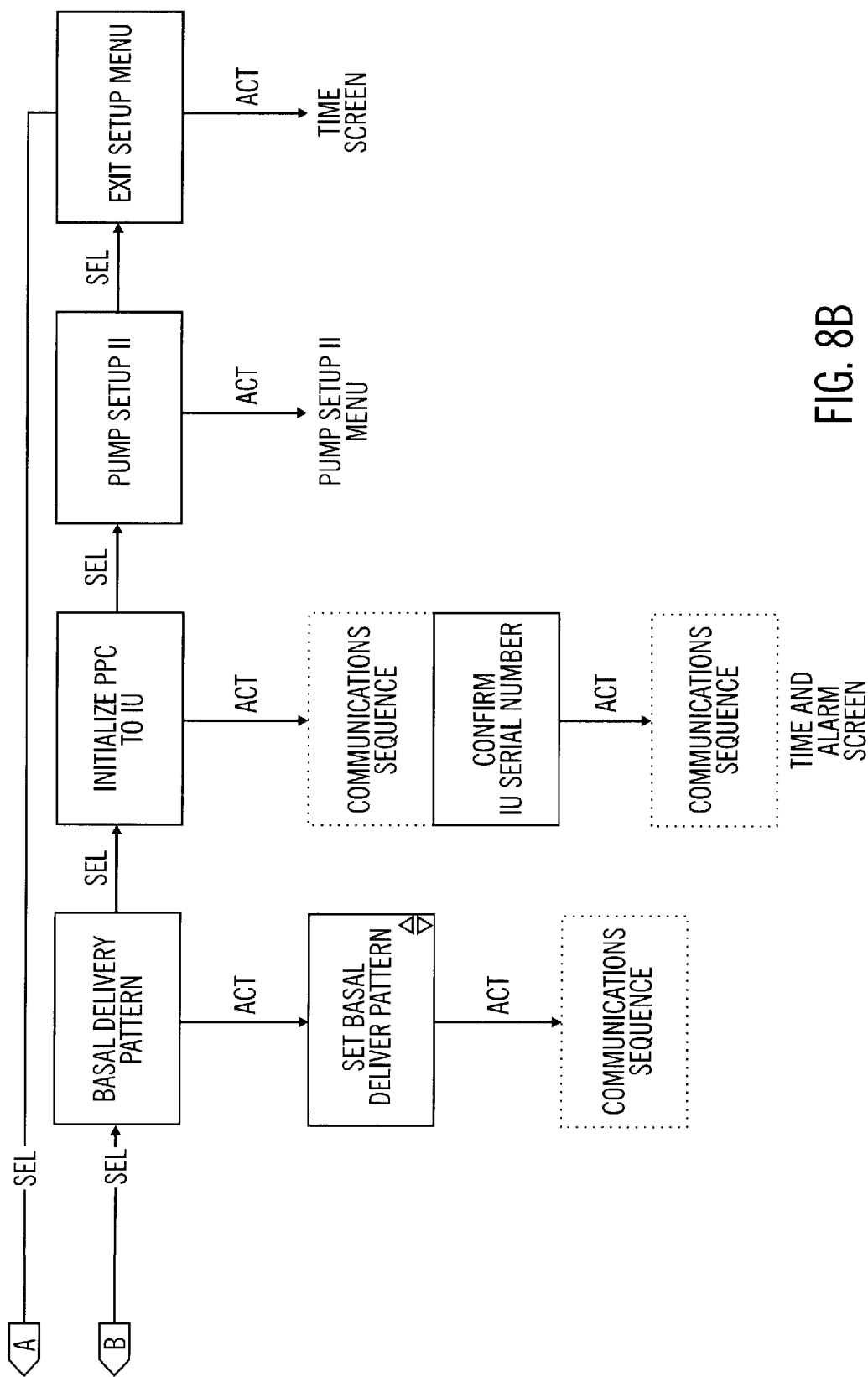
Figure 9B:
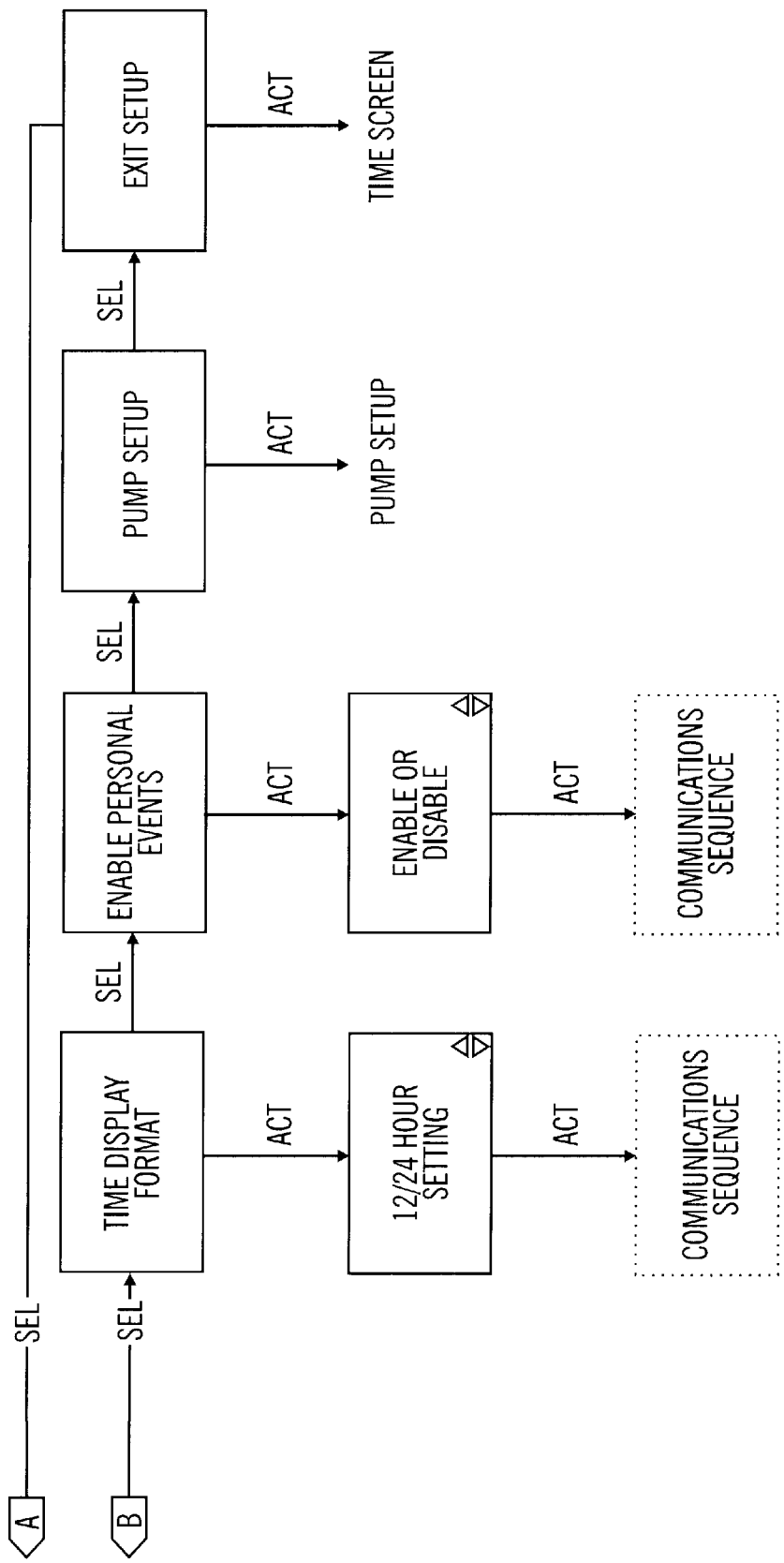
Figure 10A:
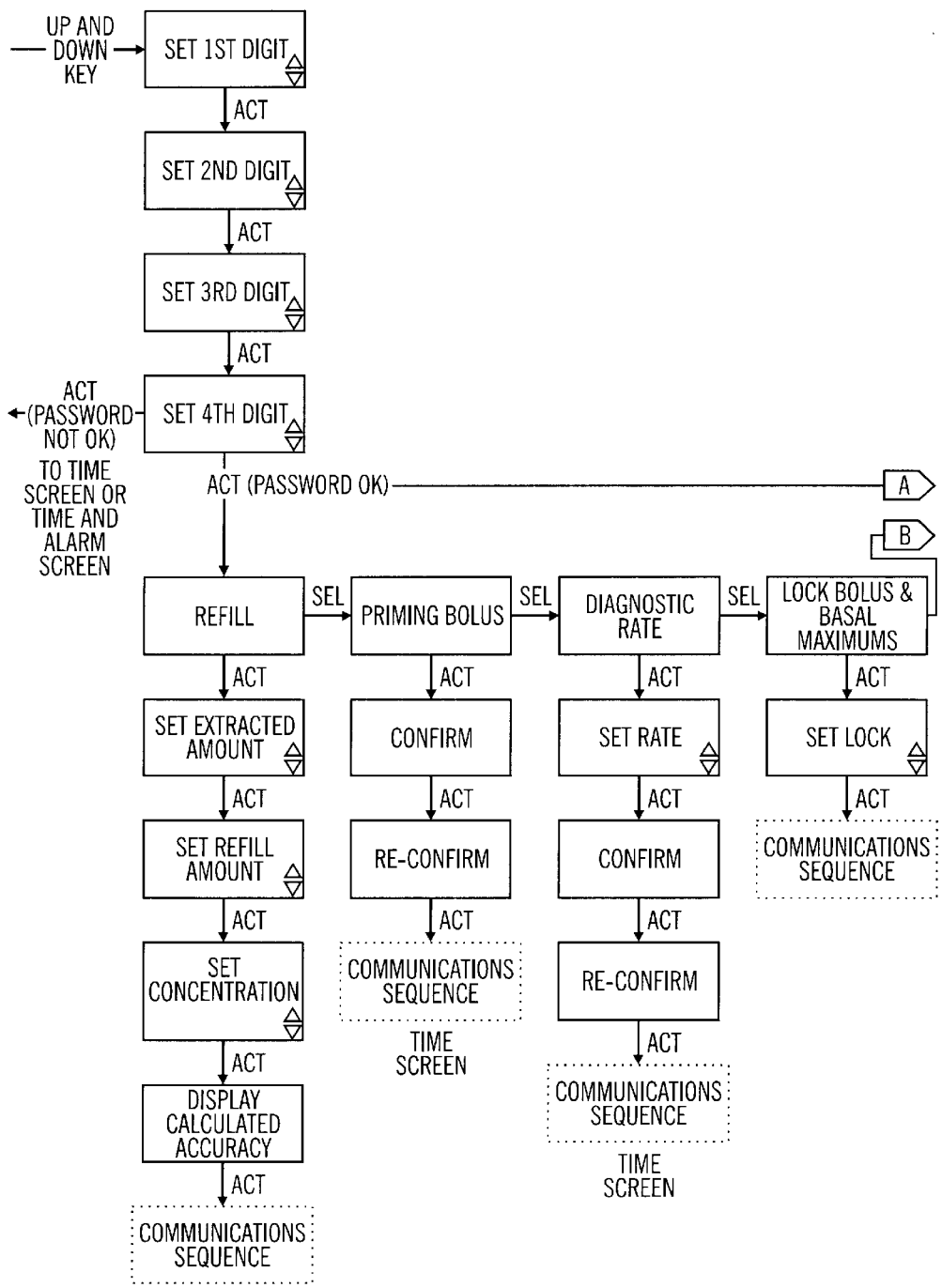
FIGS. 10a and 10b depicts the supervisor menu structure for the user interface of the external communication device of the first preferred embodiment.
Figure 10B:
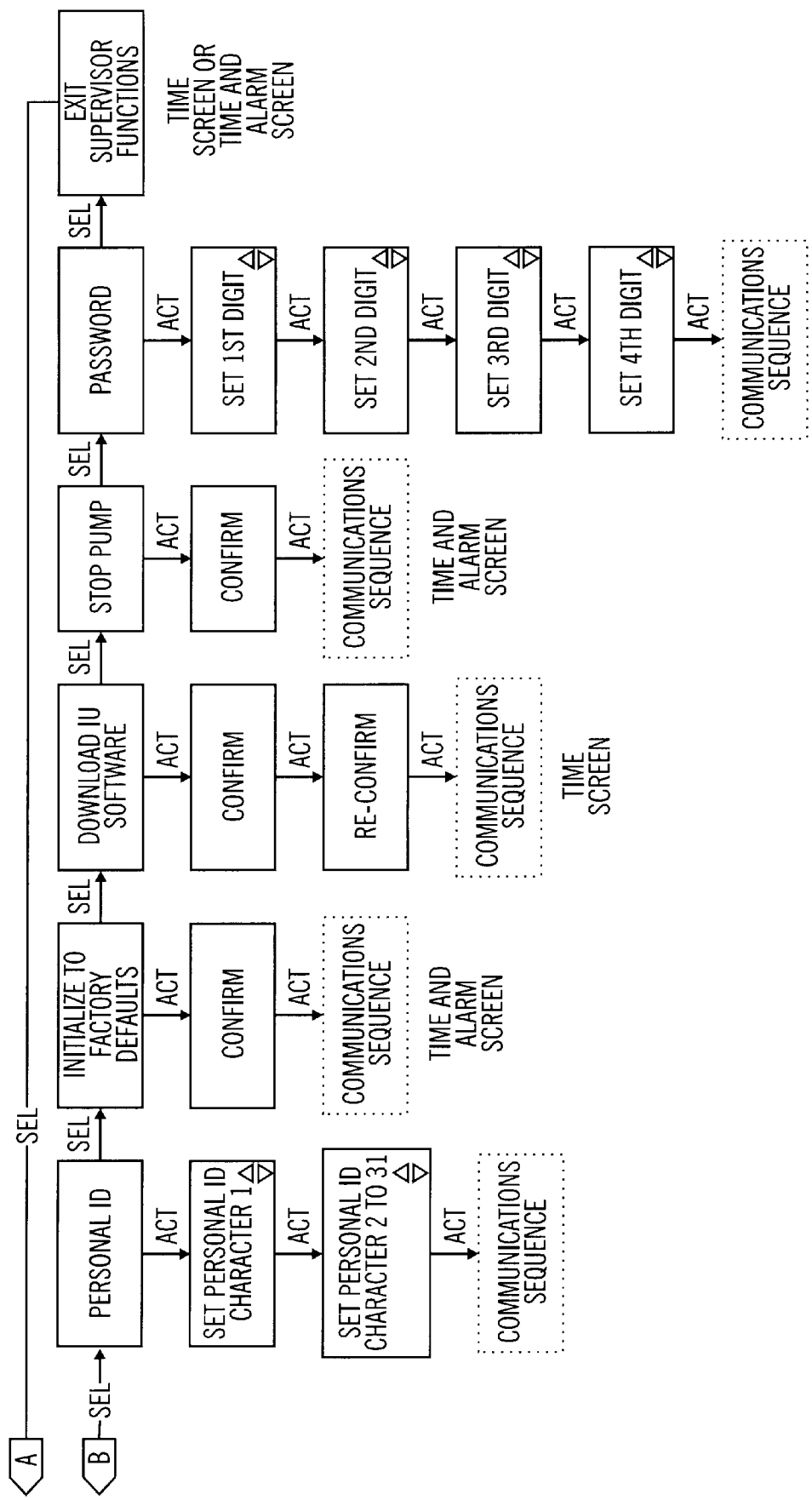

The various main menu options provided to the user in this embodiment are depicted in the block diagram of FIGS. 7a and 7b. Various set up menu options accessible from the pump setup menu display of FIGS. 7a and 7b are depicted in the block diagram of FIGS. 8a and 8b. Various pump set up II menu options accessible from the pump setup II display of FIGS. 8a and 8b are depicted in the block diagram of FIGS. 9a and 9b. Various supervisor functions/options that are accessible from the Supervisor display of FIGS. 7a and 7b are depicted in the block diagram of FIGS. 10a and 10b. The bolus delivery sequence of FIGS. 7a and 7b is further detailed in the block diagram of FIG. 11. The communications sequence of FIGS. 7a and 7b is further detailed in FIG. 12. In these Figures the ACT and SEL indications depict the keystroke necessary to change from one display to the next. The up-arrow symbol and down-arrow symbols indicate that parameter values within the menu display may be modified by pressing the UP key or the Down key.

One of the icons included in the icon region is the low-battery icon 858 (FIG. 5) which is displayed when there is a low or depleted main or backup battery. Another icon is the bell icon 860 (FIG. 5) which is turned on by the CD software when the external communication device receives a telemetry message from the implantable device indicating that the implantable device has detected one or more for the following: (1) implantable device inter-processor communications failure, (2) under-delivery, (3) over-delivery, (4) charge time too long, (5) post-fire voltage too high, (6) low implantable device battery, and (7) depleted implantable device battery. The bell icon is cleared by CD software when all alarm conditions above have been cleared. The bell icon is displayed when the external communication device is showing the 'time and alarm' screen.

Another icon is the reservoir level indicator icon 862 (FIG. 5). It is composed of 4 segments that provide a graphical indication as to the level of insulin in the implantable device reservoir. The CD software maintains an estimate of the implantable device reservoir level. The estimate is based on the refill amount indicated at the time of the latest refill which is decremented by an estimate of the insulin that has been delivered each day. The estimate of insulin delivered each day is derived from the daily total log that records the number of pump strokes delivered each day. All segments of the reservoir level icon are set when the pump is refilled. The top-most segment of the reservoir level icon is cleared when the external communication device estimates that the reservoir is less than 75% full. The top two segments of the reservoir level icon are cleared when the external communication device estimates that the reservoir is less than 50% full. The top three segments of the reservoir level icon are cleared when the external communication device estimates that the reservoir is less than 25% full. All segments of the reservoir level icon are cleared when the external communication device estimates that the reservoir is empty. Of course, in alternative embodiments a greater number, or lesser number of indicators may be used to convey the reservoir level. The last icon could be cleared when the reservoir level is not empty but instead has reached a predefined "low level". Alternatively, one or more of the elements could be controlled to blink when a low or empty reservoir condition exists.

Another icon is the Insulin Delivery Icon 864 (FIG. 5). This icon provides a rotating display when the external communication device estimates that insulin delivery is in progress. The icon includes four elements each forming a quarter of a pie shape. The rotational appearance is provided by the CD software displaying alternating patterns that change every four seconds. When the external communication device is simulating the delivery of a bolus, the pattern includes three delivery segments on, and one off. When the external communication device is simulating the delivery of a basal rate, the pattern includes one delivery segment on, three segments off. When the external communication device is simulating no insulin delivery, all four segments are on and as such, the rotational appearance is removed.

Four keys on the external communication device are provided with raised pads and provide tactile responsiveness when depressed. These four keys are labeled SEL, ACT, UP, and DOWN. Some general rules apply to the use of these keys: (1) A SEL key press moves the current screen option to the next screen option and does not change any parameter value, (2) Parameters that blink on the screen change by depressing the UP or DOWN key one or more times or by holding down one of these keys, thereby causing accelerated scrolling to occur, (3) Once parameters are set to the desired value, they are accepted by depressing the ACT key. A valid ACT keystroke is accompanied by a predefined ACT tone that is sounded by the alarm buzzer. When the ACT key triggers a telemetry message to be sent to the implantable device, upon completion of all telemetry transactions, the external communication device emits a second ACT tone to indicate that telemetry is complete.

The backlight is activated by pressing the DOWN key from the 'Time and Message' screen or the 'time & alarm' screen. The backlight is programmed to remain on for a selected period of time that may vary (e.g. 4 to 15 seconds) depending on the screen that is being displayed and/or the keys that have been pressed. For example, preprogrammed time is 4 seconds following the display of the 'time and message' screen, the 'self test results' screen, and the '24 hour basal total' screen. The timer controlling automatic shut off is reset each time a key is pressed or held down so that the timing out of the backlight may be held off.

The external communication device includes two SEEPROMs, one is used to hold CD software and data and the other may contain an image of the implantable device software. A third SEEPROM may be loaded into the external communication device for providing updated calibration parameters and the like.

The external communication device uses the power management hardware to determine the battery voltage level for the main battery and for the backup battery.

The external communication device includes A/D hardware that is used in conjunction with CD software to read the main battery level every hour, and to read the backup battery level every day at noon. The CD software checks the main low battery bit/signal 724 (FIG. 4b) in the hardware every hour to detect a dead battery.

Upon battery removal, the external communication device writes data from internal RAM to external RAM to prepare for the hardware to put the microprocessor in the reset state. The data written from internal to external RAM includes parameters and data that are necessary for the external communication device to recover when the battery is replaced. This data is termed "external communication device recovery data." When the batteries are removed, the CD software powers down the LCD so that the screen goes blank and power is conserved for completion of the writing operation. The CD software also computes a 16-bit RAM sum of the external communication device recovery data, and stores the RAM sum and its arithmetic inverse in external RAM. When the battery is replaced, external communication device performs boot up operations as described herein later.

The external communication device communicates with the implantable device through messages passed by a RF telemetry link. When the external communication device attempts to change parameters in the implantable device, the external communication device does not consider the parameter values to have been changed unless it receives the appropriate telemetry response message from the implantable device. The CD software verifies the CRC of all the telemetry messages that are received. If the calculated CRC does not match the CRC in the telemetry message, the external communication device updates a counter and otherwise ignores the receipt of the message. The CD software ignores all messages that were transmitted with the universal ID.

When transmitting most messages, sequence numbers are used. The sequence number provides a means to recover when the external communication device does not receive a telemetry response from the implantable device. When the external communication device sends a telemetry message and is expecting a response, if the response is not received, the external communication device has no way of knowing if the implantable device received the message and the external communication device missed the response, or if the implantable device simply missed the message. The sequence number provides a means for the implantable device to know whether or not it has already received a message and thus whether or not it should act on a message. When the external communication device resends a message (as it did not get a response from the previous message), the external communication device uses the same sequence number it used when it initially sent the message. If the implantable device received the previous message, the implantable device knows not to duplicate its actions because the sequence number in the current message is the same as the sequence number in the previous message. In response to the resent message, the implantable device resends its response packet using the same sequence number. This mechanism allows for the retransmission of a telemetry message without the implantable device acting on the message more than once.

The external communication device uses the sequence number parameter in the sync response telemetry message as the sequence number for the next telemetry message. The external communication device uses the sequence number parameter in the interrogate response telemetry message as the sequence number for the next telemetry message after the user has confirmed the patient ID by pressing ACT on the 'confirm implantable device serial number' screen.

When the external communication device receives a valid response to a telemetry message, unless the response is an error message, the external communication device changes the sequence number. In the present embodiment the sequence number is a single bit and as such can take on the values of "1" or "0". When the Sequence Number is 0, it is changed to 1. Similarly, if the Sequence Number is 1, it is changed to 0.

The external communication device transmits to the implantable device on inbound time slots. The external communication device enables the RF receiver every minute on the outbound time slot (e.g. on the second boundary after the minute boundary). Following the transmission of a telemetry packet, the CD software in the external communication device may enable the RF receiver on the one-second boundary and may use a listening window size that is proportional to the length of the transmitted preamble. Alternatively, the CD software may simply enable the receiver and force it on for a time that is sufficient to capture an outbound response. The RF timing system on the external communication device is configured to synchronize its concept of seconds and subseconds to those of the implantable device time upon receipt of each telemetry packet if the calculated CRC matches the CRC in the telemetry message, and the telemetry message is a valid response to an external communication device message or a valid unsolicited message.

When the time between receptions is greater than 4 minutes and less than 240 minutes, the external communication device computes a value for a one-minute RF drift variable and enters RF drift mode. If the time between receptions is not in this range, the external communication device enters preamble mode.

When the external communication device is in RF drift mode, the CD software updates a register, known as register B, by using a running RF drift value. The register B value may also be updated based on a predefined value or based on the length of the preamble so as to start transmission a desired amount of time prior to when the external communication device believes the implantable device will open its reception window. For example, the desired amount of time may be from zero to up to one half the preamble length or more. The running RF drift value is initialized to zero or some other nominal value when drift mode is entered. When the external communication device is in RF drift mode, the running RF drift value is incremented by a one-minute drift value each minute. The one-minute drift value is obtained by consideration of the time between the previous two communications and the amount of drift that was detected upon receipt of the latest transmission. When operating in RF drift mode, the external communication device uses a preamble of 6 bytes. Further detail about register B and how the information in it is used to set reception times and transmission times is provided in previously referenced US patent application No. (Docket No. USP-1077-A)

If after the increment, the running RF drift value is out of range, the external communication device enters attention mode. When in attention mode, the external communication device transmits using a two-second preamble of the attention pattern and initiates transmission using the maximum B Register value. This use of the maximum value in the B register is selected in hope of missing the reception window of the implantable device when the transmission is first initiated and in the hope of catching the attention of the implantable device closer to the end of the transmission, thus minimizing the time that the implantable device's reception system is forced to remain powered up.

When the external communication device is in preamble mode, the CD software maintains a running number of preamble bytes variable. This variable is initially set to a desired minimum value (e.g. 4, 6, or 8 bytes) and is incremented by a desired incremental value (e.g. 1–4 byte) each minute since the last communication occurred and is transmitted using the attention preamble pattern. When the external communication device is in preamble mode, the external communication device sets the register B value so that the preamble is centered on the telemetry second boundary as determined by the external communication device. When in the preamble mode, and when the running number of preamble bytes exceeds a predefined maximum value (e.g. 256–512 bytes), the external communication device enters attention mode.

In alternative embodiments, other decision-making processes may be used to select between the use of preamble mode, RF drift mode or attention mode. In fact, other modes may be defined such as a combined preamble and drift mode that widens the preamble length as time passes since the previous communication and also uses a drift rate to reposition the transmission window to keep it targeted to what the external communication device believes is the most likely position of the reception window on the implantable device.

The external communication device initiates communication with the implantable device by sending a telemetry message. If there is no response from the implantable device within a predefined time that is set by the CD software, or if the CRC of the received message does not match the CRC as calculated by the CD software, the CD software causes the packet to be resent. The CD software sets the preamble of this second packet to be twice as long as that used by the former packet but no longer than two seconds. The second message may be termed a retry packet. If the retry packet fails, the CD software initiates another retry but this time using a two-second preamble. If the external communication device does not receive a response to the second retry message, or if the response CRC does not match the calculated CRC, the CD software reports a no response error.

When the no response error is acknowledged by the user, the CD software sets aside the original message and a sync message is prepared and sent using an attention preamble that spans the gap that is believed to exist between successive reception windows (e.g. 2 seconds). If a response is still not received, the CD software may automatically (and without user notification) resend the sync message again up to a predefined number of times (e.g. 0–3 times). If a response has not been received, the no response error is again displayed. This process is repeated each time the error is cleared.

If a valid response is eventually received, and if the message was not an insulin delivery request, the CD software then retransmits the original message using a sequence number as provided in the sync response message. If the original message was for an insulin request, the user may check the delivery logs that were updated in conjunction with the last sync response message to determine whether or not the previous delivery was acted upon and thus whether or not it is appropriate to prepare a new delivery request.

If no valid response is received, the external communication device is locked out from performing any other operations other than continued attempts to reestablish communication. After taking appropriate steps to increase the likelihood of a successful communication without success, the user may elect to reset the external communication device and program it to send an interrogate message which will initially be sent with a preamble that spans the entire period between successive reception windows that exist when the implantable device is in normal mode. If this fails to achieve communication, the CD software automatically, and without user notification, resends the interrogate message using a preamble that spans the entire period between successive reception windows when the implantable device is in storage mode.

When telemetry is initiated by the external communication device, the CD software controls the external communication device to display the "transmitting to implantable device" screen so as to present the user with a positive visual feedback that the external communication device is attempting to communicate the required telemetry commands.

If a response is received from the implantable device, the acceptability of the response is verified by CD software. If the response is incorrect, or the response is not detected, the above noted no response error is asserted after making the multiple initial attempts to establish communication.

The external communication device recognizes a number of different types of alarms and conditions. The various alarms and conditions are defined with an alarm description, siren, alarm origin, and a display definition for three message areas on the dot matrix portion of the display. The siren indicates whether a yellow (Y) or blue (B) siren will be used when the alarm is active. The alarm origin indicates if the alarm is generated from a condition associated with the external communication device or with the implantable device. An alarm code is specified for a number of the potential alarm conditions. This is a unique number for each alarm condition and is used to identify the alarm in the error log and on the display.

When the CD software recognizes an alarm condition originating from the implantable device (received through telemetry), the CD software activates a siren and displays a message on the dot matrix display. The message is displayed on the 'time & alarm' screen and the siren is initiated immediately. The CD software cancels any active user interactions. When the alarm is acknowledged by the user, (e.g. by pressing the SEL key followed by the ACT key), the CD software prepares a telemetry message to clear the active implantable device alarm and to request an update of the error log. If multiple alarms are present, they are presented one at a time in prioritized order and each one may be acknowledged, cleared, and the log updated according to the above noted process. After clearing the alarms, the processing that was in progress when the alarm conditions are asserted is allowed to continue in most cases. In alternative embodiments, multiple alarm conditions may be displayed simultaneously and cleared simultaneously, or they may reviewed in turn and then cleared simultaneously.

The purpose of alarm conditions is to get the user's attention as soon as possible under most conditions. Exceptions are stop pump, suspend pump, and implantable device auto off as these conditions are system states that are cleared when the user presses SEL and ACT. As the system generally attempts to initiate alarm conditions on the external communication device first to save power in the implantable device, since telemetry transmissions are less power consumptive than buzzer activations, minimizing the duration of the alarm condition on the external communication device result in reducing the possibility of the Implantable Device alarming internally.

Reassertion of implantable device alarms are dependent on the alarm condition not being removed (i.e. the condition has not been cleared though its existence was previously acknowledged) by the time reassertion is to occur and on the implantable device communicating the error to the external communication device. Reassertion results in the alarm condition again being displayed on the LCD and the siren being activated and requiring that the use acknowledge the alarm.

The CD software handles external communication device alarms in much the same manner that it handles implantable device alarm conditions with the exception that telemetry packets need not be prepared and sent to acknowledge the alarm conditions. Reassertion of external communication device alarm conditions is similar to that for reassertion of Implantable Device alarm conditions in that they also result in a new alarm condition on the external communication device which the user must acknowledge. The exceptions to this rule are temporary basal rate, delivering diagnostic rate, and delivering priming bolus which are system states that require the external communication device to beep periodically. The following Table depicts the various alarm conditions that are recognized in the present embodiment in order of priority.

Alarm Conditions

| P | Alarm Description | O | S | Messages 0–1 | M2AC |
|---|---|---|---|---|---|
| 1 | MAIN_BATTERY_DEPLETED | CD | Y | CD - DEPLETED BATT | |
| 2 | MAIN_BATTERY_LOW | CD | Y | CD - LOW BATTERY | |
| 3 | BACK_UP_BATTERY_LOW | CD | Y | CD - NEEDS SERVICE | |
| 4 | NO_RESPONSE_EVENT | CD | Y | TELEMETRY - COMM ERROR | 3 |
| 5 | ID_DEAD_BATTERY | ID | Y | PUMP STOPPED | 6 |
| 6 | ID_EMPTY_RESERVOIR | ID | Y | EMPTY - RESERVOIR | |
| 7 | ID_OVER_DELIVERY_ERROR_BIT | ID | Y | PUMP STOPPED | 4 |
| 8 | ID_UNDER_DELIVERY_ERROR | ID | Y | PUMP STOPPED | 5 |
| 9 | ID_IP_COMM_ERROR | ID | Y | PUMP STOPPED | 1 |
| 10 | ID_CHARGE_TIME_TOO_LONG | ID | Y | PUMP STOPPED | 2 |
| 11 | ID_POST_FIRE_VOLTAGE_TOO_HIGH | ID | Y | PUMP STOPPED | 3 |
| 12 | ID_AUTO_OFF_INTERVAL_EXCEEDED | ID | Y | AUTO OFF - PUMP SUSPENDED | |
| 13 | ID_LOW_RESERVOIR | ID | Y | LOW - RESERVOIR | |
| 14 | ID_LOW_BATTERY | ID | Y | PUMP - LOW BATTERY | |
| 15 | APPLICATION_VERSION_ERROR_EVENT | CD | Y | PUMP - ERROR | 0 |
| 16 | TELEMETRY_VERSION_ERROR_EVENT | CD | Y | PUMP - ERROR | 1 |
| 17 | INVALID CONCENTRATION | CD | Y | PUMP - ERROR | 40 |
| 18 | INVALID STROKE VOLUME | CD | Y | PUMP - ERROR | 41 |
| 19 | EXCLUSION_LIST_FULL | CD | Y | TELEMETRY - COMM ERROR | 20 |
| 20 | STOP_PUMP_ALARM | CD | B | PUMP STOPPED | |
| 21 | SUSPEND_ALARM | CD | B | PUMP SUSPENDED | |
| 22 | DOWNLOAD COMPLETE | CD | Y | DOWNLOAD - COMPLETE | |
| 23 | DOWNLOAD_FAILURE | CD | Y | TELEMETRY - COMM ERROR | 27 |
| 24 | UNINITIALIZED_CD_EVENT | CD | Y | CD - NOT INITIALIZED | |
| 25 | ID_RESET_TO_DEFAULTS | CD | Y | PUMP - RESET | |
| 26 | CHECK_PUMP_STATUS | CD | Y | CHECK - PUMP STATUS | |
| 27 | HOURLY_MAXIMUM_EVENT | CD | Y | HOURLY MAX - EXCEEDED | |
| 27 | ID_INITIALIZED | CD | Y | PUMP - INITIALIZED | |
| 29 | ID_SELF_TEST_ERROR | CD | Y | PUMP - SELF TEST FAIL | |
| 30 | AUTO_OFF_ALARM | CD | Y | AUTO OFF - IN 5 MIN | |

Where P = Priority, O = Origin, S = Siren, and M2AC = Message 2 Alarm Code

When the text in Messages 0–1 do uniquely define an alarm condition, an Alarm Code is additionally displayed as a numeral that indicates the specific cause of the alarm condition.

The CD software records all external communication device alarms in the external communication device system events log.

If the low battery voltage signal is active, the CD software initiates a CD battery low alarm. A low battery message will persist on the 'Time and Message' screen until the battery has been replaced. In alternative embodiments, instead of constantly displaying this condition and thus keeping the dot matrix powered continuously, the existence of this condition may only be displayed for limited times. For example, it may be displayed when the user first interacts with the device after a time out period, or it may also be displayed after various commands are given. If the external communication device is not recognizing a dead battery condition, the CD software initiates a low battery condition check every hour. When the low battery condition is detected, the CD software logs the event.

If the dead battery voltage signal is active, the CD software initiates a CD Main Battery Depleted alarm. The CD software causes a depleted battery message to persist on the 'Time and Message' screen until the battery is replaced. When the depleted main battery condition is detected, the CD software logs the event.

The CD software causes the voltage of the backup battery to be checked every day. If the battery voltage is too low, then the external communication device needs to be refurbished. The CD software also checks for the depleted backup battery condition every day. When the depleted backup battery condition is detected, the CD software causes the depleted backup battery message to be displayed on the 'time and message' screen and logs the event. Though the user may clear the alarm, the depleted backup battery message continues to be displayed on the 'Time and Message' screen until refurbishing occurs.

When an alarm is displayed, the external communication device 'Time and Alarm' screen is active, and the user must clear the display. In the present embodiment, this is accomplished by pressing the SEL key and then the ACT key for alarms generated by the external communication device. This is initiated by pressing the SEL key and then the ACT key for alarms generated by the Implantable Device.

When an implantable device alarm is cleared by the user, the CD software prepares a clear alarm telemetry message that is transmitted to the implantable device. Upon receipt of the response, the CD software clears the active alarm condition that is displayed to the user. The CD software also re-prioritizes its alarm conditions. If there are any outstanding errors, the CD software causes the one with the highest priority to be displayed and the external communication device remains in an error state. The process of displaying, clearing, and reprioritizing continues until there are no more outstanding errors. If the alarm was detected during a telemetry transaction, the CD software resumes the telemetry transaction. However, if the alarm notification from the Implantable Device to the external communication device occurs as a result of one of the messages transmitted as part of the external communication device to Implantable Device initialization process (i.e. marrying process) the initialization process is not resumed but must be restarted beginning with the Interrogate Message.

The CD software is configured to periodically write to the watchdog hardware registers. If the system watchdog requirements are not met, a watchdog alarm is triggered and the watchdog tone is enabled by the hardware. An infinite loop at mainline or an infinite loop at interrupt level will cause the watchdog to reset the processor IC as the CD software must write one of a 0x5B or a 0A5 to the watchdog register in mainline code and the other at interrupt level.

Sirens (either audio alarm or vibrational alarm) are activated by the CD software when the external communication device detects an alarm condition. Sirens are deactivated by CD software when the alarm condition is cleared by the user. There are two types of sirens, yellow sirens and blue sirens. For yellow sirens, when the alarm type is set to 'vibrator,' the CD software activates the vibrator for 3 seconds every minute while the yellow siren is active. When the alarm type is not set to 'vibrator,' the CD software initiates a high beep tone 6 times with 250 ms between each beep, every minute while the yellow siren is active. If the yellow siren is active for more than 30 minutes, (user does not acknowledge the alarm within 30 minutes), the CD software sets the alarm type to high and initiates an alert tone every minute until the yellow siren is deactivated. If the alarm type was set to vibrator prior to crossing the 30-minute threshold, the alarm type is converted to high (i.e. loud audio) at the 30-minute threshold.

For the blue sirens, when the external communication device alarm type is set to 'vibrator,' the CD software will activate the vibrator for 3 seconds every 30 minutes while the blue siren is active. When the external communication device alarm type is not set to 'vibrator,' the CD software initiates a high beep tone 3 times with 250 ms between each beep, every 30 minutes while the blue siren is active.

The frequency and durations for the types of sounds generated by the tone generator are listed in the following table.

| Tone Frequencies | | | |
|---|---|---|---|
| Tone | Duration | Frequency | Repeat Number |
| ACT Tone | 125 ms | 516 Hz | 1 |
| High Beep Tone | 250 ms | 941 Hz | 1 |
| Audio Bolus Tone 1 | 250 ms | 516 Hz | 1 |
| Audio Bolus Tone 2 | 250 ms | 592 Hz | 1 |
| Audio Bolus Tone 3 | 250 ms | 667 Hz | 1 |
| Audio Bolus Tone 4 | 250 ms | 696 Hz | 1 |
| Double Audio Bolus Tone 1 | 250 ms | 516 Hz | 2 with 125 ms delay between |
| Double Audio Bolus Tone 2 | 250 ms | 592 Hz | 2 with 125 ms delay between |
| Double Audio Bolus Tone 3 | 250 ms | 667 Hz | 2 with 125 ms delay between |
| Double Audio Bolus Tone 4 | 250 ms | 696 Hz | 2 with 125 ms delay between |
| No Action Tone | 500 ms | 380 Hz | 1 |
| Alert Tone | 250 ms each | 941 Hz followed by 516 Hz | 6 |
| Alarm Tone | 250 ms each | 941 Hz followed by 516 Hz | 50 |
| End Bolus Tone | 250 ms | 444 Hz | 1 |

ROM boot code within the processor IC loads the external communication device bootloader code from the SEEPROM and factory defined parameters. When the external communication device boots, CD software reads the power down recovery data from external RAM and calculates the power down recovery data checksum by performing a 16-bit sum with the carry of the data. The CD software calculates the power down recovery data checksum inverse by performing an arithmetic inverse of the power down recovery data checksum.

If the calculated power down recovery data checksum matches the value in external RAM, and if the calculated power down recovery data checksum inverse matches the value in external RAM, the bootloader code copies the CD software (i.e. application code) from external RAM into internal RAM.

If the calculated checksum or checksum inverse do not match the values in external RAM, the external communication device loads the application code into external RAM from the SEEPROM. Once application code is resident in external memory, the internal portion of the code is copied from external memory to internal memory.

If the select, up, down, and activate keys are all depressed at power-up, the external communication device loads the application code into external RAM from the SEEPROM. Once the application code is resident in memory, the internal code portion is copied from external memory to internal memory.

When loading of the software is complete, the external communication device application code is started by an inter-segment jump to the main external RAM initialization address location.

Before performing conversions between insulin units and pump strokes, the CD software compares the stroke volume variable to its compliment form. If they do not agree, the CD software causes the external communication device to be reset.

Before performing conversions, the CD software compares the insulin concentration variable to its compliment form. If they do not agree, the CD software causes the external communication device to reset.

The CD software causes the external communication device to display insulin quantities to the user based on one more selected predefined units of resolution (e.g. 0.2 units for bolus quantities and 0.1 units for basal quantities). However, most computations performed by both the implantable device and the external communication device involve pump stroke volumes. In the present embodiment, the pump stroke volume is nominally 0.5 $\mu$L actually pump stroke volume may vary from this amount. When using U 400 insulin with a nominal stroke volume of 0.5 $\mu$L a dispensing resolution of nominally 0.2 units of insulin results. However, since the stroke volume may vary, the actual dispensing resolution may also vary. As such programming and interfacing between the user and device occur in increments that are not necessarily integer values of the pump stroke volume.

The CD software converts units to pump strokes based on the insulin concentration and the stroke volume:

$$PumpStrokes = \frac{Units(U) * 1000\left(\frac{uL}{mL}\right)}{Concentration\left(\frac{U}{L}\right) \cdot StrokeVolume \text{ (uL)}}$$

The CD software converts pump strokes to units based on the insulin concentration and the stroke volume:

$$Units = \frac{Concentration\left(\frac{U}{mL}\right) \cdot StrokeVolume \text{ (uL)}}{1000\left(\frac{uL}{mL}\right)} \times Pump\ Strokes$$

For display, the CD software rounds to units to the nearest 0.2 unit boundary for each Bolus and to 0.1 units for basal rates. All logs however, are maintained in pump stroke units and then converted to appropriate insulin units when displayed.

Suspend mode is a mode where the implantable device is programmed to deliver at a rate of one pump stroke an hour. The rate is clinically insignificant and serves to prevent catheter blockage. Suspend mode is enabled by the CD software from the 'suspend pump' screen. When suspend mode is entered, the CD software prepares a telemetry message for transmission to the implantable device to set its delivery mode to "suspend". When the implantable device is in suspend mode, the CD software causes the display the alarm screen to display the "pump suspended" alarm as active. When the "pump suspended" alarm condition is cleared, the CD software prepares a message for transmission to the implantable device to set the implantable device delivery mode to "normal". When the "pump_suspended" alarm condition is cleared, the CD software determines if a bolus was interrupted when suspend mode was entered. If so, it updates the bolus history log to indicate the amount of the bolus that was delivered. The CD software only provides access to the Supervisor Menu Screens while the pump is in suspend mode. A block diagram of the supervisor menu screens and options is provided in FIG. 10.

An audio bolus option is provided that enables the user to safely and reliably deliver a bolus without looking at the display. The CD software enables and disables this option from the Audio Bolus Screen in the setup menu. A block diagram of the set up menu screens and options is provided in FIG. 8. When audio bolus status is ON, the CD software enables the user to initiate delivery of a bolus by pressing the up arrow key from the 'time and message' screen as well as the 'time' screen. The CD software causes the external communication device to beep and the bolus increment to be displayed as when the up key is first depressed. The CD software provides no scrolling effect when a key is held down. The CD software increases the amount displayed by the bolus increment amount and beeps with each subsequent press of the up key.

In order to audibly distinguish bolus increments, when using the audio bolus feature, the CD software provides a single tone beep when the increment amount is set to 0.4 U, and a double tone beep when the increment value is set to 0.8 U. Of course, in alternative embodiments other incremental amounts may be used and different audio signals used to indicate which is active and what increments have been made. In one such alternative, the CD software could control an appropriately configured external communication device to speak to the user. In another such alternative, the CD software could provide voice recognition features to an appropriately configured the external communication device so that commands could be spoken instead of keyed in.

In the present embodiment, the CD software facilitates counting the audio bolus increments by varying the audio tones for the beeps that accompany the Up arrow key presses. The CD software provides four frequencies that are used in a repeating sequence as the UP arrow key is repeatedly pressed until the desired bolus amount is selected. During the programming of the audio bolus amount, the CD software interprets a pressing of the down key and sel keys to cancel the bolus. When the desired bolus amount has been programmed (and is displayed), the user may activate it by pressing the act key. When the act key is pressed and the amount is not zero, the CD software causes the external communication device to play back the beep sequence generated during bolus amount selection. The CD software interprets a subsequent pressing of the ACT key, as confirmation that the user wants to have the programmed amount delivered and as such displays the 'immediate bolus confirmation' screen. The CD software prepares a bolus delivery message for transmission to the implantable device after the user confirms the bolus amount selection by pressing the ACT key again. To cancel the delivery of the bolus after an amount has been set or while the confirmation screen is being displayed, the user may either allow the CD software to time-out and return to the 'time and message' screen or the user may press any key other than the act key.

When the delivery of an audio bolus is canceled, the CD software causes the 'time and message' screen to be displayed and causes a no action tone to be emitted. The CD software stores the audio bolus status and audio bolus increment parameters in the external communication device data block.

The CD software enables the external communication device to request delivery of three types of boluses. These are the normal bolus, the square wave bolus and the dual-phase bolus.

The normal bolus (immediate bolus or phase 1 bolus) gives the user the option to program a bolus amount in units of insulin. The insulin units requested for delivery are translated by the external communication device to an integer number of pump strokes, a telemetry message is prepared and transmitted to the implantable device which then delivers the amount.

The square wave bolus (phase 2 bolus) is programmed as an amount in units and a duration. The CD software translates the amount into a rate, a telemetry message is prepared and transmitted to the Implantable Device which then delivers insulin the computed rate for the given duration.

The dual phase bolus (two-phase bolus) is a combination of the normal bolus and the square wave bolus. The user programs a phase-one amount, a phase-two amount, and a phase-two duration into the CD software. The phase one amount is treated like a normal bolus. The phase-two amount and duration are treated like a square wave. A telemetry message is prepared and transmitted to the implantable device which is then programmed to deliver the two components of the bolus.

When a parameter called variable bolus status is set to OFF, the only type of bolus delivery that can be programmed is the normal bolus. The CD software presents the user with a 'set bolus amount' screen that the user may interact with to program a normal bolus. The CD software allows the user to increment up and down through allowable bolus amounts by using the up and down keys. The maximum amount that can be scrolled to is equal to programmable maximum bolus quantity. The CD software displays the 'immediate bolus confirmation' screen when the user depresses the act key (so long as the bolus amount indicated is not zero). When the act key is pressed again, the CD software prepares a bolus delivery request message for transmission to the implantable device.

The CD software allows a Square Wave bolus to be programmed when the variable bolus status is set ON. From the set bolus display, the CD software enables the user to select, intra alia, a square wave bolus. Once selected, the CD software shows the user a 'set bolus amount' screen with portion of the display blinking indicating that an amount may be entered. A desired bolus amount may be entered by the user using the up and down keys. The CD software limits the amount that may be entered to the predefined maximum bolus amount. After entering the amount and pressing the act key, the CD software displays a blinking region for setting bolus duration. After entering the desired duration and depressing the act key, the CD software displays a blinking screen that shows the details of the extended bolus that has been programmed (i.e. 'Extended Bolus Confirmation' screen). If the user agrees that a delivery having the indicated details should be made, the CD software initiates a telemetry delivery request message when the act key is pressed again.

The CD software also allows a dual bolus to be programmed when the variable bolus status is set on and the bolus delivery type is set to dual. In programming the bolus, three screens are presented to the user one after the other: (1) the 'set bolus amount' screen is displayed for entry of the immediate portion of the bolus, (2) the 'set phase 2 amount' is displayed for entry of the square wave portion of the bolus, and (3).the 'set phase 2 duration' screen is displayed for entry of the square wave duration. The user progresses through these screens by entering the desired amount as each screen is displayed and then hitting the act key. After the act key is depressed while the 'set phase 2 duration' screen is displayed, a flashing the 'Extended Bolus Confirmation' screen is shown. If the user agrees that a delivery having the indicated details should be made, the CD software initiates a telemetry delivery request message when the act key is pressed again. The CD software limits the total bolus amount programmed for the combination of the Immediate and the phase-2 boluses to be no more than the predefined maximum bolus amount.

For each of the above three cases, bolus delivery is initiated by the CD software preparing and initiating a deliver bolus, read totals telemetry packet. The CD software calculates the number of pumps to be delivered in the immediate bolus based on the amount programmed with the result rounded to the nearest integral number of pump strokes. The CD software also uses the phase-2 amount and duration to calculate a phase-2 delivery rate in pump strokes per minute. The calculated amount, rate and duration are passed to the implantable device for delivery in the above noted delivery request message. When the CD software estimates that a bolus delivery is in progress, the rotating delivery status icon indicates that a delivery is in progress and 'time and message' screen provides a delivering bolus message and an estimate of the amount delivered.

The CD software, estimates the amount delivered in the immediate phase of a bolus to be one pump stroke during each predefined interval of time (e.g. 2–4 seconds). Incrementing starts on the minute following completion of bolus programming.

The CD software disables the 'set maximums' screen during delivery of a bolus. Also when the estimate of the immediate amount delivered is less than the programmed amount, the 'set bolus amount' screen is also disabled. When the estimate of the immediate amount delivered equals the programmed amount, the 'set bolus amount' screen is enabled. When the estimated delivery of the combined amounts (immediate and extended) is complete the CD software causes the external communication device to emit an end of bolus tone. The CD software inhibits entry of an additional extended bolus delivery when an extended bolus is already in progress. The CD software locks out all bolus delivery screens during the delivery of an immediate bolus, diagnostic rate, or primary bolus.

As noted above, a variable bolus rate option in provided. A variable bolus status parameter is also provided that is indicative of whether the user has the capability of entering delivery instructions for all three bolus types or only the immediate type. When the option is on, bolus delivery includes a screen to choose the bolus type. When the option is off, the user can only program normal boluses. In either event, the CD software provides the user with access to those screens and options that are available to him/her and removes access/display of those screens that provide programming capability for the unavailable options.

The CD software provides a 'variable bolus' screen that may be used to set the variable bolus status parameter to on and off for enabling the programming of square wave boluses and dual wave boluses. The CD software causes the variable bolus status parameter to be stored in the external communication device data block.

The CD software provides the user with the capability of displaying the time of delivery and the amount for each of the most recent 512 boluses. Priming boluses are displayed along with variable and audio boluses. The CD software provides a 'bolus history' screen that display the most recently delivered or programmed bolus. The older entries in the bolus history log are displayed when the down arrow is pressed. Newer entries in the bolus history log are displayed when the up arrow is pressed. The up arrow is ignored when the external communication device is displaying the most recent bolus. The CD software ignores any down key presses when the external communication device is displaying the oldest log entry. When a bolus is programmed, the CD software sets the bolus status parameter to 'programmed'. The CD software updates the bolus history log when the response to the deliver bolus read totals telemetry packet is received. The CD software blanks a bolus status parameter when a response to a deliver bolus read totals telemetry packet indicates that the amount displayed for the most recently programmed bolus was delivered.

The CD software provides the user with the ability to display the total amount of insulin delivered during each of the most recent 120 days on a 'daily totals' screen. The amount for the current day is only accurate up through the delivery of the previous bolus, not the current bolus, or the last bolus. The CD software retains the total basal delivery and the total bolus delivery as separate amounts for each day in the daily totals log. The CD software displays older entries in the daily total log when the down arrow is pressed. The CD software displays newer entries in the daily total log when the up arrow is pressed. The CD software ignores Up key presses when the most recent entry in the daily total log is displayed and ignores the down key presses when the oldest daily total log entry is displayed. The CD software updates the Daily Totals log using the current day's total and yesterday's total from the TM message, when a response to the Deliver Bolus, Read Totals telemetry packet is received. The CD software maintains a pointer that indicates "today" in the daily total log. The CD software increments this pointer at midnight. When the CD software increments the pointer indicating "today", the daily total for the new day is set to dashes.

The CD software provides the user with the ability to display the contents of the external communication device event log on a external communication device 'clinical history' screen. The most recent event code for the most recently logged external communication device event is displayed on the screen. The CD software displays older entries in the external communication device event log when the down arrow is pressed and newer entries in the external communication device event log when the up arrow is pressed. The CD software ignores up arrow key presses when the external communication device is displaying the most recent entry in the external communication device event log and ignores down key presses when the external communication device is displaying the oldest entry in the external communication device event log. The CD software maintains a pointer to the most recent entry in the external communication device event log.

The CD software provides memory space for storing the contents of the implantable device event log and the ability to display those events on an 'implantable device clinical history' screen. The event code for the most recently logged implantable device event is initially displayed on the screen. The CD software displays older entries in the implantable device event log when the down arrow is pressed and newer entries in the implantable device event log when the up arrow is pressed. The CD software ignores up key presses when the external communication device is displaying the most recent entry in the implantable device event log and down key presses when the external communication device is displaying the oldest entry in the implantable device event log. The CD software maintains a pointer to the most recent entry in the implantable device Event Log. The CD software updates its implantable device event log to match the event log in the implantable device during a link and when executing the read implantable device data functionality.

The CD software provides memory space for storing entries to the implantable device battery voltage log and the ability to display those entries on an implantable device voltage history screen. The CD software initially displays the most recently logged loaded and unloaded implantable device battery voltages on this screen. The CD software displays the older entries in this log when the down arrow is pressed and newer entries in this log when the up arrow is pressed. The CD software ignores the pressing of the up key when the most recent entry in the log is being displayed and the down key when the oldest entry in the log is displayed.

The external communication device maintains a pointer to the most recent entry in the implantable device battery voltage log. The CD software updates this log to match the battery voltage log in the implantable device during a link and when executing the read implantable device data feature.

The CD software provides for a predefined number (e.g. 3 in the present embodiment) of separately programmable sets of basal rates. Each set, or profile, consists of a predefined number (e.g. up to 48 in the present embodiment) of basal rates, one for each of a predefined set of time slots (e.g. each half-hour of the day in the present embodiment). The profile rates are programmed by setting a start time and a rate. The CD software provides a basal rate screen that allows the user to view the basal rate that is currently being delivered. When there is no temporary basal rate active (the temporary basal duration is zero), the CD software displays the currently active basal profile along with its number. When a temporary basal rate is active, the active profile number is replaced with "OFF".

The CD software displays the set profile rate screen showing profile 1 when act is pressed when the 'basal rate' screen is displayed. when the act key is pressed from the set profile rate screen, the CD software displays the set profile start time screen. The minimum value for scrolling the start time is one half-hour after the start time of the previous profile. When a profile start time is programmed with a start time prior to that of one or more previously defined entries and subsequent start times are cleared (e.g. set to dashes in the present embodiment). Basal profile setting is complete when the rate for a profile starting at 11:30 pm is set. Alternatively, basal profile setting is completed when the user presses the act key for a profile start time that is dashes. When profiles in the active pattern are changed, the CD software prepares and sends a set profile basal rates message to the implantable device.

The CD software allows up to 3 delivery patterns to be separately programmed with up to 48 rates each and the patterns to be stored in the external communication device. Any one of the patterns may be set active at any time. The CD software allows the Selection of the active basal delivery pattern from the set basal delivery pattern screen. When the basal delivery pattern is set (i.e. made active) that pattern becomes accessible on the 'profile basal rate' screen and a set profile basal rates message is prepared and transmitted to the implantable device.

The temporary basal rate is a basal rate that when programmed, will run in lieu of the basal profile rate. The temporary basal rate runs for the amount of time specified by the temporary basal duration. The CD software enables setting of the temporary basal rate using the set temporary basal rate screen. When the temporary basal rate and duration are set, the CD software prepares and sends a set temporary basal rate message to the implantable device. When a temporary basal delivery is in progress, the CD software causes the remaining temporary basal rate duration to be displayed on the temporary basal rate screen. When there is no temporary basal rate delivery in progress, the CD software causes dashes to be displayed as the amount and duration of the temporary basal rate. When a temporary basal rate is set with a duration that is zero, any temporary basal rate in progress is canceled. When programming a temporary basal rate when a temporary basal rate is in progress, the CD software sets the default duration to the time remaining on the rate that is in progress rounded down to the nearest half-hour. The CD software increases the duration by one half-hour when the up key is pressed and decreases the amount by one half-hour when down key is pressed. The CD software locks out the set temporary basal rate screen during a diagnostic rate delivery and priming bolus delivery.

The CD software maintains a log of personal events. The CD software allows personal events to be set from a personal events screen. The CD software updates the log with a time and event type after the user completes the personal event data entry sequence. The personal events screen is not displayed when a personal events enable parameter is set to OFF. When the personal events screen is displayed, the most recent personal event is displayed. When the down key is pressed, the CD software displays the previous personal event in the log and when the Up key is pressed, the CD software displays the next personal event in the log. The CD software ignores presses of the Down key when the oldest personal event is being displayed and ignores the Up key when the newest personal event is being displayed.

Automatic Off is set from the 'set automatic off' screen. When the automatic off duration is set the CD software prepares and sends a set automatic off telemetry message to the implantable device. When the automatic off interval is programmed to dashes, the CD software disables the feature. The CD software maintains a timer that indicates the amount of time remaining in the automatic off interval. When telemetry responses from the implantable device are received, and the response is not the interrogate response, the CD software resets the timer to the automatic off interval. The CD software decrements the time in the automatic off interval timer every minute. When the amount of time in the automatic off interval is five minutes (indicating that the Implantable Device will alarm in 5 minutes), the CD software reports an "automatic off alarm" alarm.

The CD software maintains the time and the date. The CD software enables the time and the date to be set from the 'time and date' screen. When ACT is pressed, the 'set time' screen is displayed. When the 'set time' screen is displayed, the CD software allows the user to change the hours and the minutes. When act is pressed and the minutes are displayed, the CD software displays the set date screen. When the date and the time are set by the user, the CD software prepares and sends out a set current time telemetry message to the implantable device. In the present embodiment, though the external communication device has direct knowledge of date and changes in date that may occur, this direct knowledge is not used in determining, among other thing, how to set daily totals. In alternative embodiments, this direct knowledge may be used for this purpose; however, in the present embodiment the following analysis is performed by the CD software and associated conclusions made: (1) If the new hour is less than the current hour (measured on a 24 hour clock), and the new hour subtracted from the current hour is greater than or equal to 12, new day processing takes place, (2) If the new hour is greater than the current hour and the current hour subtracted from the new hour is greater than or equal to 12, previous day processing takes place, and (3) If the new hour and current hour are not separated by more than 12 hours the day is considered to remain unchanged. When new day processing occurs, the CD software updates the daily totals as is normally carried out at midnight. When previous day processing occurs, the CD software moves the daily total data log pointer to the previous day and adds current daily total values to those of the previous day.

An hourly maximum amount is provided for by the CD software. The hourly maximum is the amount of insulin that may be delivered with boluses in one hour. If a higher amount is programmed, the CD software reports an error. In the present embodiment, the hourly maximum amount is not a hard limit but one that may be bypassed if desired by the patient. In effect, the hourly maximum amount provides a warning to the patient so that the patient will not unintentionally deliver a large amount of insulin within a single 60-minute period. In the present embodiment, after clearing the warning, a window of predefined length (e.g. 10 minutes) is opened so that an additional bolus of up to the single bolus maximum amount (i.e. bolus maximum) may be delivered without triggering the hourly maximum amount error. In the present embodiment the hourly maximum amount is set to a predetermined multiple of the single bolus maximum amount (e.g. 2.5 times). In alternative embodiments, the time period of the maximum may be specified to a larger or shorter amount and/or the amount of the maximum may be set in a different way.

Each time a bolus is programmed, the CD software computes the amount of bolus delivery that occurred during the previous 60 minutes. If the amount delivered summed with the programmed amount is greater than 2½ times the bolus maximum, the CD software reports an "hourly maximum exceeded" alarm and the CD software does not transmit a telemetry message to the implantable device to initiate the bolus. When the "hourly maximum exceeded" alarm is cleared the CD software sets a ten-minute time period in which CD software will not test for the "hourly maximum exceeded" alarm. The CD software resumes testing for the "hourly maximum exceeded" alarm after the ten-minute time period elapses.

In other alternative embodiments, instead of basing the Hourly Maximum testing on amounts actually delivered in the last 60 minutes, the testing may be based on amounts programmed during the last 60 minutes. Also in alternative embodiments, an estimated timing of delivery for the amount(s) programmed may be factored into the calculations before concluding that the hourly maximum will actually be exceeded, especially when the amount programmed for delivery includes an extended bolus.

The CD software allows a basal rate maximum to be defined and then uses this maximum value in limiting the basal rates that can be programmed for delivery during any one period of time. In the present embodiment, the CD software inhibits the user from programming basal profiles or temporary basal rates that are greater than the value of the basal rate maximum. When the basal rate maximum is changed, the CD software prepares and sends the implantable device a set maximums Message. The CD software inhibits a maximum basal rate from being programmed that is set to a value lower than a programmed basal rate, including profile basal rates, both active and inactive, and the temporary basal rate.

The CD software sets the medication remaining parameter to the refill amount when a response to a "set refill amount and alarm thresholds" message is received. The CD software subtracts the daily total values (not taken from the amounts displayed but instead derived from the number of pump strokes executed) from the "remaining medication" parameter once per day at midnight.

The CD software performs a self-test and initiates the implantable device self-test through telemetry. The external communication device self-test is initiated from the external communication device self-test screen. When the external communication device self-test is initiated, the CD software sends an Initiate Self-Test telemetry message to the implantable device so that it may be tested as well. When the CD software receives a valid response to the initiate self-test telemetry message, the CD software indicates to the user that the Implantable Device has passed the self-test. If the external communication device does not receive a response to the initiate self-test telemetry message, the CD software indicates that the implantable device has failed the self-test. The external communication device sends the implantable device a read self-test status message when the external communication device wants to know the results of the test.

When the external communication device self-test is initiated, the CD software displays the 'screen operation verification' screen, an alert tone is emitted, the vibrator is enabled for a predefined period of time (e.g. 3 seconds), the CD software computes a CRC of the code area in internal RAM and compares the computed value to the CRC stored in the SEEPROM, the CD software computes a CRC of the code area in external RAM and compares the computed value to the CRC stored in the SEEPROM, and the CD software illuminates the Backlight for a predefined period of time (e.g. four seconds). If either of these CRC comparisons do not produce a match, the CD software causes the external communication device to reset. When the CD software has completed the self-test sequence, the CD software indicates that the external communication device has passed the self-test (assuming it has). It is up to the user to confirm whether the vibrator operated and whether the display was illuminated. In other embodiments, appropriate transducers and circuitry may be used to automatically ascertain the functionality of various components such as those noted above.

The external communication device alarm type is set from the alarms screen, in conjunction with the audio feedback mode. audio and vibration alarms are set by the 'alarms' screen. When the 'alarms' screen is displayed and the act key is pressed, the CD software displays the external communication device alarm type screen. When the alarm type screen is displayed and the act key is pressed, the CD software displays the 'audio feedback mode' screen.

The CD software stores the alarm type parameter in the external communication device memory but when the parameter is changed, it also transmits a set external communication device data block message (containing the updated alarm type parameter) to the implantable device for storage in the external communication device data block.

The CD software allows the audio feedback mode to be set from the alarms screen, in conjunction with the external communication device alarm type. audio feedback mode is enabled and disabled from the set audio feedback mode screen. When the audio feedback status parameter is set to ON the CD software sends the implantable device the set audio feedback mode message enabling audio feedback mode. When the audio feedback status parameter is set to OFF the CD software sends the implantable device the set audio feedback mode telemetry message disabling audio feedback mode.

The CD software causes the external communication device to storage mode if there is no keyboard activity and there have been no telemetry packets received for seven days. The external communication device exits storage mode if a key is pressed or the batteries are removed and replaced. When the external communication device is in storage mode, the screen is disabled and the telemetry hardware is disabled, time is maintained (but not displayed) and memory is retained but all other functions become unavailable.

The pump refill process is initiated from the 'pump refill' screen. pressing act on the pump refill screen causes the 'set extracted amount' screen to be displayed. Pressing ACT on the 'set extracted amount' screen causes the 'set refill amount' screen to be displayed. Pressing act on the 'set refill amount' screen causes the 'Set Concentration' screen to be displayed. Pressing ACT on the 'set concentration' screen initiates the CD software to calculate the delivery accuracy. When the CD software computes the delivery accuracy to be a negative number, it displays the value as positive number along with the words "Under-Delivery". When the cd software computes the delivery accuracy to be a positive number, the value is displayed along with the words "over-delivery". When the extracted amount is dashes, the extracted amount is logged as zero and this event is logged in the system event log. The accuracy is displayed as dashes. When the CD software determines that the extracted amount is more than the previous refill amount, the CD software logs a system event and displays the accuracy as dashes. When the CD software determines that the extracted amount equals the previous refill amount, the CD software logs a system event and displays the accuracy as dashes.

Changing the insulin concentration is part of the refill screen sequence. When insulin concentration is changed on the 'set concentration' screen, the CD software resets all profile basal rates and the temporary basal rate to factory default values. When the basal profiles are cleared, the CD software sends the implantable device a set basal rates message and a set insulin concentration message. When the insulin concentration is changed, the CD software recomputes the current basal rate maximum and bolus maximum and sends the implantable device a set maximums message.

The priming bolus screen is found on the supervisor menu. The CD software locks out the priming bolus screen unless the pump is in stop mode. Priming the pump is initiated from the priming bolus screen. When the user presses the act key on the 'priming bolus' screen, the CD software displays the confirm priming bolus screen. When the user selects 'yes' and presses the act key on the 'confirm priming bolus' screen, the CD software displays the reconfirm priming bolus screen. When the user presses the ACT key on the 'reconfirm priming bolus' screen, the cd software sends a set delivery mode message to the implantable device with the mode set to indicate priming bolus, and the priming bolus amount set to a predefined value (such as 650 pump strokes).

The diagnostic rate screen is on the supervisor menu. It is used to perform diagnostic procedures on the pumping mechanism by setting very high rates. Normally, the reservoir is not filled with insulin when this feature is used. The diagnostic rate screen is locked out unless the pump is in stop mode. diagnostic rate is initiated on the 'diagnostic rate' screen. When the user presses the act key on the 'diagnostic rate' screen, the CD software displays the set diagnostic rate Screen. When the user presses the act key on the set diagnostic rate screen, the cd software displays the confirm diagnostic rate screen. When the user selects 'yes' and presses the act key on the confirm diagnostic rate screen, the CD software displays the reconfirm diagnostic rate screen. When the user presses the act key on the reconfirm diagnostic rate screen, the CD software prepares and sends a set delivery mode message to the implantable device with the mode set to indicate diagnostic rate, and the diagnostic rate amount equal to the amount set on the 'set diagnostic rate' screen. While the diagnostic rate is in progress, the CD software displays a message on the 'time and message' screen to indicate that the diagnostic rate is in progress.

The maximum lock feature is a safety feature accessible from the supervisor menu. This feature enables and disables the patient's ability to change the delivery maximums. The maximum lock feature is accessible on the 'lock bolus and basal maximums' screen. When the user presses act from this screen, the set lock screen is displayed. When the user presses act on the set lock screen, the CD software sends a set maximums message to the implantable device. When the locked maximum status parameter is on, the CD software ignores the act key when it is pressed while the max bolus screen is displayed. When the locked maximum status parameter is on, the CD software ignores the act key when it is pressed while the max basal rate screen is displayed.

The read implantable device data feature synchronizes the external communication device and the implantable device. The read implantable device data feature is accessible from the read implantable device data screen. When the user presses act on this screen, the CD software initiates the read implantable device data process. The read implantable device data process includes reading the Implantable device data log pointers and reading all of the data necessary to make the data logs in the external communication device mirror the data logs in the implantable device.

Setting the personal ID is initiated on the personal ID screen. When act is pressed on the personal ID screen, the CD software displays the "set personal id character 1" screen. As there are 32 characters available for use as the personal ID in this embodiment, 32 screens are supplied for entry of the personal ID. When ACT is pressed on the final character of the personal ID, the CD software sends a "set personal id message" to the implantable device.

The external communication device contains an image of the implantable device software in one of its SEEPROMs. The image includes instructions to perform all of the telemetry transactions necessary to download the software, including for example, an interrogate message, a link message, a reset message, an interrogate message, a link message, download start message & data, one or more download continue messages and data, and a bootstrap message. The SEEPROM includes code and data for both the main and the monitor processors on the implantable device. Downloading implantable device software is initiated on the "download implantable device software" screen. When the user presses the act key on the "download implantable device software" screen, the CD software displays the "confirm download implantable device software" screen. When the user selects 'yes' and presses the act key on this screen, the CD software displays the re-confirm download implantable device software screen. When the user presses the ACT key on this screen, the CD software initiates the software download. The CD software reads the SEEPROM and uses the size and the data, in formulating telemetry packets to send to the implantable device. If appropriate message responses are received by the CD software, it continues sending packets until the data read from the SEEPROM indicates that there is no more data. If errors are detected during the download process, the CD software displays the download error screen.

Stop mode is a mode where the implantable device is programmed to stop all insulin delivery. The CD software limits accessibility to only supervisor menu screens when the pump is in stop mode. stop mode is enabled from the "stop pump" screen. When stop mode is entered, the CD software prepares and transmits a telemetry message to the implantable device to set the delivery mode to stop mode. When stop mode is entered, the CD software displays the alarm screen with "pump stopped" alarm active. When the "pump stopped" alarm condition is cleared, the CD software sets prepares and sends a telemetry message to the implantable device to set the delivery mode to normal mode and also updates the bolus history log to indicate the amount of the latest bolus that was delivered.

The CD software provides single command ability to set parameter values in the implantable device to their factory default values. This capability is produced from the "initialize to factory defaults" screen. Several telemetry commands are used to initialize the implantable device to factory defaults successfully. When the choice is confirmed to reset the parameters, the CD software sends the telemetry messages indicated in the following table to the implantable device to set the parameters to their factory default values:

| Telemetry Messages to Initialize to Factory Defaults |
| --- |
| Set Current Time |
| Set Automatic Off |
| Set External Communication Device Data Block |
| Set Maximums |
| Set Audio Feedback Mode |
| Set Personal ID |
| Set Temp Basal Rate |
| Set Basal Profile Rates |
| Set Delivery Mode |

The CD software provides a one command process for initializing the external communication device to implantable device. After completing this sequence, the external communication device is configured to match the implantable device settings with the exception of the basal profiles which are set to factory defaults in the implantable device and the external communication device. The Initialize external communication device to implantable device process is initiated from the initialize external communication device to implantable device screen. When the ACT key is pressed and the 'initialize external communication device to implantable device' screen is being displayed, the CD software sends the implantable device an interrogate message. When the response to the interrogate telemetry message is received, the CD software displays the 'confirm implantable device serial number' Screen. This screen contains a message that gives the user the choice to confirm or reject the displayed personal ID. The user may choose "yes" or "no" to confirm or reject and abort the initialization process. The CD software sets the "no" choice as the default. When the 'no' choice is confirmed, the external communication device attempts to add the telemetry ID from the interrogate response message to the exclusion list. If the exclusion list is full, the CD software reports an "exclusion list full" alarm. If the exclusion list is not full, the CD software sends out another interrogate message, in hopes of getting the correct implantable device to respond. The rejection process may be repeated multiple times if a large number of implantable devices are in the vicinity. When the 'yes' choice is confirmed, the CD software sends the telemetry messages to the implantable device as indicated in the table below.

| Telemetry Messages to Initialize the External Communication Device to Implantable Device |
| --- |
| Interrogate |
| Link External Communication Device to Implantable Device |
| Read Stroke Volume |
| Read Lifetime Total Delivered |
| Read Audio Feedback Mode |
| Read Insulin Concentration |
| Read Automatic Off |
| Read Implantable Device Data Log Pointers |
| Read Refill Counter |
| Read Maximums |
| Read External Communication Device Data Block |
| Read Memory |
| Set Temp Basal Rate |
| Set Basal Profile Rates |
| Set Delivery Mode |

The stroke volume received in the read stroke volume response is range-checked by the CD software to ensure that it is a valid value. If the stroke volume is not within range, and "invalid stroke volume" alarm is reported, and the CD software will not initialize the external communication device to the implantable device. If valid, the CD software stores the stroke volume as received and once more in its complimented form.

The insulin concentration received in the read concentration response is also range checked by the CD software to ensure that it is a valid value. If the insulin concentration is not within the range, the CD software reports an "invalid stroke volume" alarm and the CD software will not initialize the external communication device to the implantable device. If valid, the CD software stores the insulin concentration as received and once more in its complimented form.

With the set delivery mode message, the CD software sets the delivery mode to suspend. With the set temporary basal rate and the set basal profile rates messages, the CD software sets the implantable device basal rates, including the profiles and temp basal rates to the factory default values.

During programming of the external communication device, if there is no active alarm and no buttons are pressed, the external communication device will return to the 'time and message' screen after a predefined period of inactivity.

When an alarm is in the process of being cleared, the CD software returns the external communication device to the "time and alarm" screen. The time-out (i.e. predefined period of inactivity) is dependent upon the last key that was pressed, if telemetry occurred, and if an alarm was beeping. In the present embodiment, several different time out periods are used: (1) The time-out is 4 seconds after telemetry occurs; (2) 15 seconds after an interrogate; (3) 15 seconds after audio bolus beeping; (4) 7 seconds after a sel key is pressed; (5) 15 seconds after all other keys are pressed, except for when the down key is pressed to activate the backlight; and (6) 4 seconds after the activation of the backlight.

The CD software provides a set of functions that are only accessible with a supervisor password. In order for the user to access the supervisor menu, the user must enter a supervisor password on the password screen. When a predefined group of keys are pressed simultaneously (e.g. the two arrow keys), for a predefined number of seconds (e.g. 3–5 seconds), from one or more selected screens (e.g. the time alarm & sel screen, or the pump setup screen) the password screen is displayed. When the user is presented with the password screen, the user enters a selected number of parameters (e.g. four parameters defined as password entry 1, password entry 2, password entry 3, and password entry 4). The CD software presents one parameter at a time for entry. When the act key is pressed, subsequent password entry parameters may be entered. when "act" is pressed after specifying password entry 4, the CD software compares password entry 1–4 parameters to password 1–4 parameters. If the four values match, the CD software displays the 'supervisor menu' screen. If the values do not match, the CD software compares password entry 1–4 parameters to the factory password parameters 1–4. If the four values are within a predefined amount of each other (e.g. less than or equal to 24 apart), the CD software displays the supervisor menu screen. If the values do not match, the CD software displays the time and message screen. The following tables present a listing of the various screen names along with a brief description of them.

| Screen | Description |
| --- | --- |
| The Main Menu contains the following screens | |
| Main Menu Screens | |
| Time | This is the screen that displays the current time and the icons. |
| Time and Message | This screen will be displayed when there are messages such as bolus delivery in progress and temporary basal rate in progress. |
| Bolus History | This is the screen that shows the boluses that have been delivered. A new bolus may be started from this screen. |
| Suspend Pump | This is the screen where the user can stop (clinically speaking) insulin delivery. |
| Basal Rate | This is the screen where the basal profiles may be reviewed and programmed. |
| Temporary Basal Rate | This is the screen where a temporary basal rate may be programmed or canceled. |
| Personal Events (when enabled) | This screen is where the user can record the incidence of events such as exercise and meals for later review. Note that this screen will not be in the Main Menu unless it is enabled in the Setup II menu. |
| History Menu | This is a menu (described below) that shows historical insulin delivery information. |
| Pump Setup | This is the menu where the pump setup options are located. |
| The History Menu contains the following screens: | |

| Screen | Description |
| --- | --- |
| History Menu Screens | |
| Read Implantable Device Data | This screen is where the user can Synchronize the Implantable Device data and the external communication device data. |
| Medication Remaining | This screen shows how much medication is remaining in the pump reservoir. |
| Daily Totals | This screen shows the total amount of insulin delivered for the most recent 90 days. |
| Exit History | This screen exits the History Menu and returns to the Main Menu. |
| External Communication Device Clinical History | This screen shows the external communication device Event Log entries. |
| Implantable Device Clinical History | This screen shows the Implantable Device Event Log entries. |
| Implantable Device Voltage History | This screen shows the Implantable Device Battery Voltage Log entries. |
| The Pump Setup Menu contains the following screens: | |
| Pump Setup Menu Screens | |
| Time and Date | This is the screen where the user sets the time and the date. |
| Automatic Off | This is the screen where the user sets and clears the automatic off duration. |
| Alarms | This is the screen where the user sets the alarm type (audio high, audio low, or vibrator) and where the user sets audio feed back mode. |
| Self-Test | This is the screen where the user initiates a self-test for the external communication device and the Implantable Device. |
| Basal Delivery Pattern | This is the screen where one of the three basal profile delivery patterns is selected. |
| Initialize External Communication Device to Implant | This is where the external communication device and the Implantable Device are "married". This must be carried out before an external communication device and an Implantable Device can communicate. |
| Pump Setup II | This is where the Pump II menu can be entered. |
| Exit Setup | This screen exits the Pump Setup Menu and returns to the Main Menu. |
| The Pump Setup II Menu contains the following screens: | |
| Pump Setup II Menu Screens | |
| Audio Bolus | This is where the audio bolus feature is enabled and disabled. |
| Variable Bolus | This is where the ability to choose a bolus type on the bolus setting screen is enabled and disabled. |
| Maximum Bolus | This is where the maximum bolus amount is set. |
| Maximum Basal Rate | This is where the maximum basal rate is set. |
| Time display format | This is where the time display can be set to either 12-hour or 24-hour clock. |
| Personal Events | This is where the personal events feature is enabled and disabled. |
| Exit to Pump Setup | This screen exits Pump Setup II and enters Pump Setup I menu. |
| Exit Setup | This screen exits the Pump Setup II menu and returns to the Main Menu. |
| The Supervisor Menu contains the following screens: | |
| Supervisor Menu Screens | |
| Refill | This is where the user enters the amount of medication put into the pump. This is used for the low and empty reservoir alarms. |
| Priming Bolus | This is where a priming bolus that is designed to remove air from the catheter is programmed. |
| Diagnostic Rate | This where the diagnostic rate is programmed. |

-continued

| Screen | Description |
|---|---|
| Bolus and Basal Maximum Lock | This is where the ability for the user to change maximums in the Pump Setup II Menu is enabled and disabled. |
| Personal ID | This is where the 32 character personal ID is set. |
| Initialize to Factory Defaults | This feature programs pump parameters to the factory defaults. |
| Download Pump Software. | This is where the pump software can be downloaded. |
| Stop Pump | This feature stops and resumes all pumping. |
| Set Supervisor Password | This is where the password for the Supervisor Menu is set. |
| Exit Supervisor Menu | This screen exits the Supervisor Menu and returns to the Main Menu. |

Any field that is displayed and that may be changed over the product lifetime is identified as a parameter field. To clarify parameter definition, parameters can be thought of as being subdivided into numeric parameters and option parameters. The numeric parameter will generally be a number. The definition for numeric parameters includes a minimum value and a maximum value and a unit of how the parameter is measured. For all parameters, the defaults values are shown. Numeric parameters also include a step value that indicates how scrolling will increment and decrement when the parameter can be changed by the user. Numeric parameters may show dashes when they are disabled. This is indicated by the term 'dashes'. Option parameters will generally be a set of options that the user scrolls through when the parameter is set. Option Parameters are shown with all the available choices and the default.

The factory default is the value or option that the parameter will be set to when the external communication device is shipped from the factory as a new product. The operating default is the value or option that the parameter will be set to when the external communication device has been initialized properly to an Implantable Device, and the user has interacted with the parameter.

PART 1 - External Communication Device Parameter Summary

| Parameter | Factory Default | Operating Default | Units | Delta Value |
|---|---|---|---|---|
| Accuracy Status | | "%" will be displayed. "Under Delivery" will be displayed if Delivery Accuracy is negative; otherwise "Over Delivery" will be displayed. | | |
| Audio Bolus Increment | 0.4 | Previously programmed value. | Units | 0.4 |
| Audio Bolus Status | OFF | Previously programmed value. | | |
| Audio Feedback Status | OFF | Previously programmed value. | | |
| Auto-Off | DISABLED | Previously programmed value. | Hours | 1 |
| Basal Rate Total | | programmed value. | Units | |
| Bolus Amount | Dashes | Last Bolus Amount | Units | |
| Bolus Delivery Type | NORMAL | NORMAL | | |
| Bolus Status | Blank. | Dependent upon pump status. The text PROGRAMMED will be displayed at any time the bolus on the screen has not been confirmed as being delivered. If the bolus has been delivered this section of screen will be blank. | | |
| Bolus Time & Date | Dashes | Time & Date of last bolus | dependent on Time Format and Date Format parameter settings. | |
| Daily Total Basal Amount | Dashes | Previously programmed value. | Units | |
| Daily Total Bolus Amount | Dashes | Previously programmed value. | Units | |
| Daily Total Date | Dashes | Previously programmed value. | Month and Day | |
| Day | 1 | Previously programmed value. | | 1 day |
| Delivery Accuracy | | [100 × (Estimated Delivery − Amount Delivered)/Amount Delivered], where Amount Delivered is [Previous Refill Amount − Extracted Amount] and Estimated Delivery is ((1.04 g/mL) × Units Delivered/Insulin Concentration) | Percent | |
| Delivery Pattern | A | Previously programmed value. | | |
| Diagnostic Rate | 10 | 10 | Units/hour | 5 |
| Event Time & Date | Current Time & Date | Current Time & Date | Dependent on Time Format | |
| Event Type | MEAL | MEAL | | |
| Extended Bolus Amount | Dashes | Dashes | Units | 0.2 |
| Extended Bolus Duration | 30 minutes | 30 minutes | Hours:minutes | 30 minutes |
| Extracted Amount | 0.1 | 0.1 | Grams | 0.1 |
| Factory Password 1–4 | Operating Default | (24 * Month * 32 + 24 * Day + Hour) (Note that January is 0, February is 1, etc) | | |

-continued

PART 1 - External Communication Device Parameter Summary

| Parameter | Factory Default | Operating Default | Units | Delta Value |
|---|---|---|---|---|
| Hour | 0 | Previously programmed value. | Dependent on Time Format parameter setting. | 1 hour |
| Immediate Bolus Amount | Dashes | Dashes | Units | 0.2 |
| Insulin Concentration | U-400 | Previously programmed value. | | |
| Implantable Device SW version | 2-byte from Telemetry | 2-byte from Telemetry | | |
| Locked Maximums Status | OFF | Previously programmed value. | | |
| Maximum Basal Rate | 0.2 | Previously programmed value. | Units/hour | 0.1 |
| Maximum Bolus | 10 | Previously programmed value. | Units | 0.2 |
| Medication Remaining | 0 | Previously programmed value. | Units | |
| Minutes | 0 minutes | Previously programmed value. | Dependent on Time Format parameter setting. | 1 minute |
| Month | JAN | Previously programmed value. | | |
| Password Character 1 | Y | Previously programmed value. | | |
| Password Character 2 | I | Previously programmed value. | | |
| Password Character 3 | Q | Previously programmed value. | | |
| Password Character 4 | 8 | Previously programmed value. | | |
| Character Password Entry Character 1-4 | 0 | 0 | | |
| Personal Event Status | OFF | Previously programmed value | | |
| Personal ID Character | 0 | Previously programmed value. | | |

-continued

PART 1 - External Communication Device Parameter Summary

| Parameter | Factory Default | Operating Default | Units | Delta Value |
|---|---|---|---|---|
| 1–32 ECD Alarm Type | HIGH | Previously programmed value. | | |
| CD software Version | 2-byte stored value. | 2-byte stored value. | | |
| Priming Bolus | [((Pump Volume) + (Catheter Volume)) × (Insulin Concentration)] | [((Pump Volume) + (Catheter Volume)) × (Insulin Concentration)] | Units | |
| Profile Basal Rate Amount | Dashes | Previously programmed value. | u/h | 0.1 |
| Profile Basal Rate Start Time | Previous start time plus 30 minutes | Previously programmed value. | Dependent on Time Format parameter setting. | 30 minutes |
| Refill Amount | 0.1 | 0.1 | Grams | 0.1 |
| Temporary Basal Rate Amount | Dashes | Dashes | units/hour | 0.1 |
| Temporary Basal Rate Duration | Dashes | Dashes | Hours:minutes | 30 minutes |
| Time Format | 12 HOUR | Previously programmed value. | | |
| Variable Bolus Status | OFF | Previously programmed value. | | |
| Year | 2000 | Previously programmed value. | | 1 year |

PART 2 - External Communication Device Parameter Summary

| Parameter | Interface Minimum | Interface Maximum | Options | Number of Records |
|---|---|---|---|---|
| Accuracy Status | | | | |
| Audio Bolus Increment | 0.4 | 0.8 | | |
| Audio Bolus Status | | | ON or OFF | |
| Audio Feedback Status | | | ON or OFF | |
| Auto-Off Duration | DISABLED and then 1 | 16 | | |
| Basal Rate Total | | | | |
| Bolus Amount | | | | 512 |

-continued

| PART 2 - External Communication Device Parameter Summary | | | | |
|---|---|---|---|---|
| Parameter | Interface Minimum | Interface Maximum | Options | Number of Records |
| Bolus Delivery Type | | | NORMAL, DUAL, OR SQUARE | |
| Bolus Status | | | | |
| Bolus Time & Date | | | | 512 |
| Daily Total Basal Amount | | | | 120 |
| Daily Total Bolus Amount | | | | 120 |
| Daily Total Date | | | | 120 |
| Day | 1 | 31 | | |
| Delivery Accuracy | 0 | 100 | | |
| Delivery Pattern | | | A, B, or C | |
| Diagnostic Rate | 10 | 240 for U-400, 300 for U-500 | | |
| Event Time & Date | | | | 512 |
| Event Type | | | MEAL, SNACK, SICK, EXERCISE, A, B, C. | 512 |
| Extended Bolus Amount | Dashes and then 0.2 U | Dependent on Maximum Bolus parameter | | |
| Extended Bolus Duration | 30 minutes | 4 hours | | |
| Extracted Amount | Dashes and then 0.1 U | 25 | | |
| Factory Password 1-4 | | | | |
| Hour | 0 | 11:00 PM | | |
| Immediate Bolus Amount | Dashes and then 0.2 U | Dependent on Maximum Bolus parameter | | |
| Insulin Concentration | | | U-400, or U-500 | |
| Implantable Device SW version | | | | |
| Locked Maximums Status | | | ON or OFF | |
| Maximum Basal Rate | 0.2 | 35 | | |
| Maximum Bolus | 0 | 25 | | |
| Medication Remaining | | | | |
| Minutes | 0 minutes | 59 minutes | | |
| Month | | | JAN, FEB, MAR, APR, MAY, JUN, JUL, AUG, SEP, OCT, NOV, DEC | |
| Password Character 1 | number 0 | letter Z | | |
| Password Character 2 | number 0 | letter Z | | |
| Password Character 3 | number 0 | letter Z | | |
| Password Character 4 | number 0 | letter Z | | |
| Password Entry Character 1-4 | number 0 | letter Z | | |
| Personal Event Status | | | ON or OFF | |
| Personal ID Character 1-32 | number 0 | letter Z | | |
| External Communication Device Alarm Type | | | HIGH, LOW, or VIBRATE | |
| CD software Version | | | | |
| Priming Bolus | | | | |
| Profile Basal Rate Amount | Dashes and then 0.1 | dependent on Maximum Basal Rate parameter | | 48 per Delivery Pattern |
| Profile Basal Rate Start Time | previous start time plus 30 minutes (except if it is Profile 1, which always starts at 12:00 am) | 11:30 PM | | 48 per Delivery Pattern |
| Refill Amount | 0.1 | 25 | | |
| Temporary Basal Rate Amount | Dashes and then 0.1 | Dependent on Maximum Basal Rate parameter | | |
| Temporary Basal Rate Duration | Dashes and then 30 minutes | 24 hours | | |
| Time Format | | | 12 HOUR or 24 HOUR | |

-continued

PART 2 - External Communication Device Parameter Summary

| Parameter | Interface Minimum | Interface Maximum | Options | Number of Records |
|---|---|---|---|---|
| Variable Bolus Status | | | ON or OFF | |
| Year | 1999 | 2050 | | |

The external communication device may use its IrDA port to communicate with other secondary external devices, such as a desktop personal computers. The external communication device may communicate with two classes of secondary devices: (1) devices for extracting information from the communication device for providing primarily health care related analysis for use by the patient or physician, i.e. a clinician station, and (2) devices for extracting information from and writing information to the communication device for system related diagnostics and problem solving, i.e. diagnostic station.

The clinician station may be a desktop computer running a program designed to monitor and display diagnostic information provided by the external communication device and an implantable device for a health care professional. The clinician station type external device cannot write data to the external communication device or the implantable device.

The diagnostic station may be a desktop computer running a program designed to aid in the diagnosis of system problems through communication with the implantable device and the external communication device. The diagnostic station has the capability to write data to the implantable device and to the external communication device.

A full-duplex link between, the external communication device and an second external device such as the clinician station is provided through the serial communication port. This port provides transmit and receive lines that support infrared LEDs for establishing functional connections to external devices. The transmit and receive lines also support RS232 connections to external devices.

Messages are initiated by the second external device. The receiving device allows a predefined time before concluding the transmission has ended. If this time is exceeded before a complete message is received, the receiving device responds with a "no acknowledge" message. The receiver expects the next byte to be the first byte of a message.

The external communication device maintains a low power state by disabling some of the UART circuitry. The second external device transmits a "wake-up" message in order to enable the external communication device receiver. When the external communication device is in the UART low power state and a byte is received, the external communication device enables all UART capabilities appropriate for communication with an external device. When the external communication device UART is idle for 10 seconds it enters the low-power state. All messages except for a wake-up and listen message follow a format similar to that noted above for an RF telemetry message.

For safety reasons the external communication device recognizes two distinct communication channels using the IR port: the clinician channel and the diagnostic channel. The clinician station software uses a clinician channel to communicate to the external communication device. The messages that are available for each channel type are different. The clinician channel messages do not modify external communication device or implantable device memory but diagnostic channel messages can. A specific channel closes when the "channel close" message is received or when the interval between messages exceeds a predefined channel time out interval. Each channel is closed upon system start-up and remains closed a "channel open" message is received for that specific channel.

While the above description has provided various teachings concerning how the communication device may handle various RF telemetry operations, IR communication operations, alarm notifications, and other functional activities, many other such operations are definable. These other operations may be defined in manners that are analogous to the teachings presented above or in ways that are consistent with those teachings and do not lead to communication ambiguity or other potential mishandling of medical device operation.

The above embodiment and its alternatives provide numerous enhancements in the electronic control of the medical device. These improvements provide more functional, reliable, safe, user friendly, convenience operation of an implantable medical device and more generically of an ambulatory medical device.

While the above embodiment has primarily been concerned with an implantable infusion pump that dispenses insulin using a piston type (i.e. pulsatile) pump mechanism, the electronic control features disclosed herein may be used in other ambulatory devices such as implantable pacemakers, defibrillators, other implantable tissue stimulators, implantable physiologic sensors such as electrochemical oxygen sensors, peroxide sensors, or enzymatic sensors such as glucose sensors, externally carried infusion pumps, implantable infusion pumps that use other pumping mechanisms or simply used excess pressure and controlled flow elements to infuse various medications and drugs such as analgesics, drugs for treating AIDS, drugs for treating psychological disorders and the like. For example, the features presented above may be used with an external infusion pump that may or may not have a built in display and keypad but is equipped with a telemetry system that can communicate with a physically separated communication device so that the pump need not be accessed in order to provide commands to it and receive data from it.

In these various alternatives, the physical, electronic, and programmed features of the communication device and implantable device may have different components and features than presented above for the implantable pump system so that their desired medical functionality and safety requirements are achieved and such that appropriate control and feedback is provided between the medical device and its communication device.

In other alternative embodiments the medical device may include two medical devices such as an implantable pump and an implantable sensor. The pump may dispense a drug whose physiological impact on the body (e.g. analgesic impact) is ascertained by the sensor or alternatively the sensor may supply a physiological reading that indicates a need for infusion of the drug. The pump may operate in a closed loop manner with the sensor or it may operate in an open loop manner where the patient is required to interpret sensor output information and is required to issue appropriate infusion commands to the pump. For example, in the case of a diabetic patient, the drug may be insulin and the sensor may detect glucose level.

In other alternative embodiments two medical devices may be implanted adjacent one another or at an extended distance from one another. If not placed in physical contact with one another, a lead may be used to provide power conduction from one device to the other and also be used to conduct communication signals between the devices. Alternatively, each device may include at least one telemetry system that allows direct communication between each or allows indirect communication to occur via the external communication device or other external device. Each device may be supplied with its own power supply. Depending on the communication requirements each device may use two way communication (i.e. both outbound and inbound communication) or allow only one way communication (i.e. outbound communication or possibly inbound communication).

In other alternatives, both the medical device and the communication device may be external devices (e.g. an external pump and an external RF telemetry based communication device). In still further alternatives, a first type of medical device may be implanted (e.g. an infusion pump or a sensor) while a second medical device may be external (e.g. the opposite of a sensor or an infusion pump). Where at least one of the medical devices is external, it may also function as the communication device for the other medical device in which case it may possess a display for providing information to the patient and a keypad for allowing entry of commands for issuance to the implantable device as well as for direct use by itself. Even if at least one of the medical devices is external, it may be inconvenient to access that device when information is needed or commands must be given, as such an external, non-medical communication device may be supplied that has information output (e.g. display) capabilities and input (e.g. keypad) capabilities. If a separate communication device is provided, the external medical device may or may not have display and input capabilities.

The telemetry features presented above may be used with various forms of distant communication (e.g. between the implantable device and other external devices or between the external communication device and other external devices). For example communication may occur via various electromagnetic links like IR, optical links, longer or shorter wavelength RF, audio links, ultrasonic links, acoustic links, inductive links, and the like. Various telemetry systems may be used. Telemetry systems may be of the analog type, digital type, or mixed.

In other embodiments two independent processors may be used that operate from a single timing chain. In these alternatives, it is preferable that at least one of the timing signals (e.g. one of the lower frequency timers) be monitored by an independently timed watchdog circuit to reduce the risk of timing problems going undetected.

In still additional embodiments, an implantable glucose sensor may be used in conjunction with an implantable insulin pump to provide feedback to the patient or physician on the effectiveness of the insulin delivery system. The patient could use the feedback to assist in making insulin delivery decisions in an open loop manner. Alternatively, the operation of the pump could be tied to the sensor output in a more or less closed loop manner to give a more automated character to system operation. Insulin may be infused without any user intervention, without pre-delivery information, and even without direct post delivery feedback. In a less automated closed loop system, drug infusion recommendations could be derived by the system and presented to the user before delivery or the system could require user acknowledgment prior to proceeding with delivery for amounts or rates exceed a predefined limit. The implantable sensor may have its own power supply or may receive power from the control circuitry provided within the pump housing through a physical lead that connects them. Power may be supplied through one or more independent leads or alternatively may be transferred over one or more data lines through the communication signals themselves. Communication may be exchanged in various ways including, for example, via galvanic leads, RF telemetry, fiber optics, and the like, and may be of digital, analog, or combined form. The sensor system may include a plurality of sensor elements which might allow continued glucose data to be supplied even though some portion of the sensors stop operating, lose calibration or produce questionable readings. The most preferred sensors would include electronic processing capability in the form of an integrated circuit mounted in or forming a part of a housing for the sensor. This configuration has the advantage of allowing digital communications between the physical sensor and any separated electronic control module.

Further teachings concerning implantable sensors and implantable sensor systems are found in a number of patents issued to D. A. Gough, including (1) U.S. Pat. No. 4,484,987, entitled "Method And Membrane Applicable To Implantable Sensor"; (2) U.S. Pat. No. 4,627,906, entitled "Electrochemical Sensor Having Improved Stability"; (3) U.S. Pat. No. 4,671,288, entitled "Electrochemical Cell Sensor For Continuous Short-Term Use In Tissues And Blood"; (4) U.S. Pat. No. 4,703,756, entitled "Complete Glucose Monitoring System With An Implantable Telemetered Sensor Module"; and (5) U.S. Pat. No. 4,781,798, entitled "Transparent Multi-Oxygen Sensor Array And Method Of Using Same". Each of these patents is incorporated herein by reference as if set forth in full.

Still further teachings concerning implantable sensors and sensor systems are found in a number of patents issued to J. H. Schulman, et al., including (1) U.S. Pat. No. 5,497,772, entitled "Glucose Monitoring System"; (2) U.S. Pat. No. 5,651,767, entitled "Replaceable Catheter System for Physiological Sensors, Stimulating Electrodes and/or Implantable Fluid Delivery Systems"; (3) U.S. Pat. No. 5,750,926, entitled "Hermetically Sealed Electrical Feedthrough For Use With Implantable Electronic Devices"; (4) U.S. Pat. No. 6,043,437, entitled "Alumina Insulation for Coating Implantable Components and Other Microminiature Devices"; (5) U.S. Pat. No. 6,088,608, entitled "Implantable Sensor and Integrity Test Therefor"; and (6) U.S. Pat. No. 6,119,028, entitled "Implantable Enzyme-Based Monitoring Systems Having Improved Longevity Due to Improved Exterior Surfaces". Each of these patents is incorporated herein by reference as if set forth in full.

Additional further teachings concerning implantable sensors and sensor systems are found in (1) U.S. Pat. No. 5,917,346, issued to J. C. Gord, et al., and entitled "Low powercurrent-to-frequency converter"; (2) U.S. Pat. No. 5,999,848, issued to J. C. Gord, and entitled "Daisy Chainable Sensors for Implantation in Living Tissue"; (3) U.S. Pat. No. 5,999,849, issued to L. D. Canfield, et al., and entitled "Low Power Rectifier Circuit for Implantable Medical Devices"; and (4) U.S. Pat. No. 6,081,736, issued to M. S. Colvin, et al., and entitled "Implantable Enzyme-Based Monitoring Systems Adapted for Long Term Use". Each of these patents is incorporated herein by reference as if set forth in full.

Further teachings concerning implantable infusion pumps are found in a number of patents by R. E. Fischell, including (1) U.S. Pat. No. 4,373,527, entitled "Implantable, Programmable Medication Infusion System"; (2) U.S. Pat. No. 4,494,950, entitled "Infusion Device Intended for Implantation in a Living Body"; (3) U.S. Pat. No. 4,525,165, entitled "Fluid Handling System for Medication Infusion System"; (4) U.S. Pat. No. 4,573,994, entitled "Refillable Medication Infusion Apparatus"; (5) U.S. Pat. No. 4,594,058, entitled "Single Valve Diaphragm Pump with Decreased Sensitivity to Ambient Conditions"; (6) U.S. Pat. No. 4,619,653, entitled "Apparatus For Detecting At Least One Predetermined Condition And Providing An Informational Signal In Response Thereto In A Medication Infusion System"; (7) U.S. Pat. No. 4,661,097, entitled "Method for Clearing a Gas Bubble From a Positive Displacement Pump Contained Within a Fluid Dispensing System"; (8) U.S. Pat. No. 4,731,051, entitled "Programmable Control Means for Providing Safe and Controlled Medication Infusion"; and (9) U.S. Pat. No. 4,784,645, entitled, "Apparatus For Detecting A Condition Of A Medication Infusion System And Providing An Informational Signal In Response Thereto". Each of these patents is incorporated herein by reference as if set forth in full.

Still further teachings concerning infusion pumps are found in a number of patents by Franetzki, including (1) U.S. Pat. No. 4,191,181, entitled "Apparatus For Infusion of Liquids", (2) U.S. Pat. No. 4,217,894, entitled "Apparatus for Supplying Medication to the Human or Animal Body"; (3) U.S. Pat. No. 4,270,532, entitled "Device for the Pre-programmable Infusion of Liquids"; (4) U.S. Pat. No. 4,282,872, entitled "Device for the Pre-programmable Infusion of Liquids", U.S. Pat. No. 4,373,527, entitled "Implantable, Programmable Medication Infusion System"; (5) U.S. Pat. No. 4,511,355, entitled "Plural Module Medication Delivery System", (6) U.S. Pat. No. 4,559,037, entitled "Device for the Pre-programmable Infusion of Liquids"; (7) U.S. Pat. No. 4,776,842, entitled "Device for the Administration of Medications". Each of these patents is incorporated herein by reference as if set forth in full.

Teachings concerning tissue stimulators are found in a number of patents by J. H. Schulman, including (1) U.S. Pat. No. 5,193,539, entitled "Implantable microstimulator"; (2) U.S. Pat. No. 5,193,540; entitled "Structure and Method of Manufacture of an Implantable Microstimulator"; and (3) U.S. Pat. No. 5,358,514, entitled "Implantable Microdevices with Self Attaching Electrodes". Further teachings are also found in (1) U.S. Pat. No. 5,957,958, by Loeb et al., entitled "Implantable nerve or muscle stimulator e.g. a cochlear prosthesis", in (2) U.S. Pat. No. 5,571,148, by G. E. Loeb, et al., entitled "Implantable Multichannel Stimulator"; and in (3) PCT Publication No. WO 00/74751, by A. E. Mann, and entitled "Method and Apparatus for Infusing Liquids Using a Chemical Reaction in an Implanted Infusion Device". Each of these publications is incorporated herein by reference as if set forth in full.

The control of an implantable sensor could be provided through the functionality of one or both Processor ICs. One Processor IC could supply power and/or control signals to the sensor(s) and receive data back from the sensor, while the other processor could monitor the activity to ensure that sensor activity meets certain predefined guidelines.

In other embodiments, the External Communication Device of the first embodiment could be functionally linked to an external glucose sensor system such as the continuous glucose monitoring system (CGMS) offered by Minimed Inc. of Northridge, Calif. The link may be established, for example, through a physical lead or by RF telemetry.

In other embodiments other implantable, or external, sensor systems that measure something other than glucose could also be functionally coupled to the implantable device either to receive power and/or to provide data. Other such sensors might include oxygen sensors, peroxide sensors, pulse rate sensors, temperature sensors, accelerometers, and the like.

In still other alternative embodiments, the electronic control system of the first embodiment could be configured to control one or more implantable sensors or electrical stimulators with or without infusion functionality incorporated into the implantable device.

Further embodiments will be apparent to those of skill in the art upon review of the disclosure provided herein. Still further embodiments may be derived from the teachings set forth explicitly herein in combination with the teachings found in the various patent applications.

While the description herein sets forth particular embodiments, it is believed that those of skill in the art will recognize many variations to the presented embodiments based on the teachings herein, as such it is believed that many additional modifications may be made without departing from the spirit of the teachings herein. The accompanying claims are intended to cover such modifications as would fall within the true scope and spirit of the present invention. The disclosed embodiments are therefore to be considered as illustrative and not necessarily restrictive, the scope of the invention being indicated by the appended claims, rather than the foregoing description, and all changes which come within the meaning and range of equivalency of the claims are therefore intended to be embraced therein.

We claim:

1. A medical system, comprising:

a) an ambulatory medical device (MD) comprising MD electronic control circuitry that further comprises at least one MD telemetry system and at least one MD processor that controls, at least in part, operation of the MD telemetry system and operation of the medical device, wherein the medical device is configured to provide a treatment to a body of a patient or to monitor a selected state of the body; and b) a communication device (CD) comprising CD electronic control circuitry that further comprises at least one CD telemetry system and at least one CD processor that controls, at least in part, operation of the CD telemetry system and operation of the communication device, wherein the CD telemetry system sends messages to or receives messages from the MD telemetry system, wherein the medical device is configured to deliver a substance to the body of the patient; and wherein the communication device is configured to program the medical device to deliver the substance to the body of the patient according to a programmed delivery profile that includes multiple basal rates, each basal rate defining a rate of delivery of the substance and a time interval for delivery at the defined rate of delivery; and wherein the communication device is further configured to program the medical device to deliver the substance to the body of the patient according to a temporary basal rate for a defined period of time and thereafter according to the programmed delivery profile.

2. The system of claim 1 wherein a first portion of the MD telemetry system is incorporated into the MD processor and a second portion of the MD telemetry system is external to the MD processor, or wherein a first portion of the CD telemetry system is incorporated into the CD processor and a second portion of the CD telemetry system is external to the CD processor.

3. The system of claim 2 wherein (1) the MD electronic control circuitry comprises at least one external MD functional module, other than the second portion of the MD telemetry system, that is external to the MD processor, (2) the CD electronic control circuitry comprises at least one external CD functional module, other than the second portion of the CD telemetry system, that is external to the CD processor, (3) the MD processor comprises an internal MD CPU and at least one other internal MD functional module, or (4) the CD processor comprises an internal CD CPU and at least one other internal CD functional module.

4. The system of claim 1 wherein communication device further comprises:
a) a CD housing;
b) a user readable CD display supported by the CD housing; and
c) a touch sensitive CD input device supported by the CD housing.

5. The system of claim 4 wherein the communication device has dimensions no greater than 1.2 inch by 4 inch by 5 inch.

6. The system of claim 5 wherein the communication device has dimensions no greater than 0.8 inch by 3 inch by 4 inch.

7. The system of claim 1 wherein the communication device weighs no more than 6 oz.

8. The system of claim 1 wherein the communication device comprises a CD auditory alarm or a CD vibration alarm that is controlled by the CD processor.

9. The system of claim 1 further comprising a second device and wherein the communication device and the second device include infrared communication systems that are capable of passing communication signals therebetween.

10. The system of claim 4 wherein the medical device is programmable and wherein the communication device stores at least one program that is executable by the medical device and that can be downloaded to the medical device via the CD and MD telemetry systems.

11. The system of claim 4 wherein the medical device comprises an MD memory that holds MD operation data, and wherein the communication device is capable of requesting and receiving selected portions of the MD operation data via telemetry.

12. The system of claim 11 wherein the data is clinical diagnostic data.

13. The system of claim 11 wherein the data is system diagnostic data.

14. The system of claim 4 wherein the CD display comprises a graphics LCD.

15. The system of claim 4 wherein the CD display comprises a multiple icon display.

16. The system of claim 4 wherein the communication device operates from a single 1.5 volt battery.

17. The system of claim 1 wherein the medical device comprises at least one of (1) an implantable infusion pump for selectively dispensing a selected drug, (2) an implantable infusion pump for selectively dispensing insulin, (3) an implantable sensor for sensing a selected state of the body, (4) an implantable sensor for sensing glucose level, or (5) an implantable electrode for selectively stimulating a portion of the body of the patient.

18. The medical system of claim 1,
wherein the medical device is further configured to provide a drug to the body of a patient in amounts that are integer multiples of a quantized amount,
wherein the communication device is programmed to allow entry of delivery quantities that are not integral multiples of the quantized amount,
wherein the communication device is further programmed to convert the delivery quantities that are not integral multiples of the quantized amount into amounts that are integral multiples of the quantized amount, and
wherein the communication device communicates the delivery quantities to the medical device as integral multiples of the quantized amount.

19. The system of claim 18 wherein a first portion of the MD telemetry system is incorporated into the MD processor and a second portion of the MD telemetry system is external to the MD processor, or wherein a first portion of the CD telemetry system is incorporated into the CD processor and a second portion of the CD telemetry system is external to the CD processor.

20. The system of claim 19 wherein (1) the MD electronic control circuitry comprises at least one external MD functional module, other than the second portion of the MD telemetry system, that is external to the MD processor, (2) the CD electronic control circuitry comprises at least one external CD functional module, other than the second portion of the CD telemetry system, that is external to the CD processor, (3) the MD processor comprises an internal MD CPU and at least one other internal MD functional module, or (4) the CD processor comprises an internal CD CPU and at least one other internal CD functional module.

21. The system of claim 18 wherein the medical device is a pulsatile pumping device.

22. The system of claim 18 wherein the medical device is an electromagnetically activated piston pump.

23. The system of claim 18 wherein the medical device comprises at least one of (1) an implantable infusion pump for selectively dispensing a selected drug, (2) an implantable infusion pump for selectively dispensing insulin, (3) an implantable sensor for sensing a selected state of the body, (4) an implantable sensor for sensing glucose level, or (5) an implantable electrode for selectively stimulating a portion of the body of the patient.

24. The system of claim 1 wherein the communication device weighs no more than about 10 oz and comprises a CD housing having a volumetric size smaller than 20 cubic inches.

25. The system of claim 1 wherein the communication device is further configured to receive status information about a backup CD power source.

26. The system of claim 25 wherein the status information is received when the backup CD power source is depleted.

* * * * *